US009388465B2

(12) United States Patent
Hindson et al.

(10) Patent No.: US 9,388,465 B2
(45) Date of Patent: Jul. 12, 2016

(54) POLYNUCLEOTIDE BARCODE GENERATION

(71) Applicant: 10X Genomics, Inc., Pleasanton, CA (US)

(72) Inventors: Benjamin Hindson, Pleasanton, CA (US); Mirna Jarosz, Palo Alto, CA (US); Paul Hardenbol, San Francisco, CA (US); Michael Schnall-Levin, Palo Alto, CA (US); Kevin Ness, Pleasanton, CA (US); Serge Saxonov, Oakland, CA (US)

(73) Assignee: 10X GENOMICS, INC., Pleasanton, CA (US)

( * ) Notice: Subject to any disclaimer, the term of this patent is extended or adjusted under 35 U.S.C. 154(b) by 0 days.

(21) Appl. No.: 14/175,973

(22) Filed: Feb. 7, 2014

(65) Prior Publication Data
US 2014/0228255 A1 Aug. 14, 2014

Related U.S. Application Data

(60) Provisional application No. 61/762,435, filed on Feb. 8, 2013, provisional application No. 61/800,223, filed on Mar. 15, 2013, provisional application No. 61/840,403, filed on Jun. 27, 2013, provisional application No. 61/844,804, filed on Jul. 10, 2013.

(51) Int. Cl.
C12N 15/10 (2006.01)
C12Q 1/68 (2006.01)
C12N 15/11 (2006.01)
G01N 33/543 (2006.01)

(52) U.S. Cl.
CPC .......... *C12Q 1/6876* (2013.01); *C12N 15/1065* (2013.01); *C12N 15/11* (2013.01); *C12Q 1/6806* (2013.01); *G01N 33/5436* (2013.01); *C12Q 2600/112* (2013.01)

(58) Field of Classification Search
None
See application file for complete search history.

(56) References Cited

U.S. PATENT DOCUMENTS

| | | | |
|---|---|---|---|
| 5,149,625 A | 9/1992 | Church et al. |
| 5,202,231 A | 4/1993 | Drmanac et al. |
| 5,413,924 A | 5/1995 | Kozak et al. |
| 5,436,130 A | 7/1995 | Mathies et al. |
| 5,512,131 A | 4/1996 | Kumar et al. |
| 5,587,128 A | 12/1996 | Wilding et al. |
| 5,618,711 A | 4/1997 | Gelfand et al. |
| 5,695,940 A | 12/1997 | Drmanac et al. |
| 5,736,330 A | 4/1998 | Fulton |
| 5,834,197 A | 11/1998 | Parton |
| 5,851,769 A | 12/1998 | Gray et al. |
| 5,856,174 A | 1/1999 | Lipshutz et al. |
| 5,958,703 A | 9/1999 | Dower et al. |
| 5,994,056 A | 11/1999 | Higuchi et al. |
| 6,046,003 A | 4/2000 | Mandecki |
| 6,051,377 A | 4/2000 | Mandecki |
| 6,057,107 A | 5/2000 | Fulton |
| 6,103,537 A | 8/2000 | Ullman et al. |
| 6,143,496 A | 11/2000 | Brown et al. |
| 6,172,218 B1 | 1/2001 | Brenner |
| 6,297,006 B1 | 10/2001 | Drmanac et al. |
| 6,297,017 B1 | 10/2001 | Schmidt et al. |
| 6,327,410 B1 | 12/2001 | Walt et al. |
| 6,355,198 B1 | 3/2002 | Kim et al. |
| 6,361,950 B1 | 3/2002 | Mandecki |
| 6,372,813 B1 | 4/2002 | Johnson et al. |
| 6,406,848 B1 | 6/2002 | Bridgham et al. |
| 6,432,360 B1 | 8/2002 | Church |
| 6,485,944 B1 | 11/2002 | Church et al. |
| 6,511,803 B1 | 1/2003 | Church et al. |
| 6,524,456 B1 | 2/2003 | Ramsey et al. |
| 6,586,176 B1 | 7/2003 | Trnovsky et al. |
| 6,632,606 B1 | 10/2003 | Ullman et al. |
| 6,632,655 B1 | 10/2003 | Mehta et al. |
| 6,670,133 B2 | 12/2003 | Knapp et al. |
| 6,767,731 B2 | 7/2004 | Hannah |
| 6,800,298 B1 | 10/2004 | Burdick et al. |
| 6,806,052 B2 | 10/2004 | Bridgham et al. |
| 6,806,058 B2 | 10/2004 | Jesperson et al. |
| 6,859,570 B2 | 2/2005 | Walt et al. |
| 6,913,935 B1 | 7/2005 | Thomas |
| 6,929,859 B2 | 8/2005 | Chandler et al. |
| 6,969,488 B2 | 11/2005 | Bridgham et al. |
| 6,974,669 B2 | 12/2005 | Mirkin et al. |

(Continued)

FOREIGN PATENT DOCUMENTS

EP 0249007 A2 12/1987
EP 0637996 B1 7/1997

(Continued)

OTHER PUBLICATIONS

Chou, et al. Disposable Microdevices for DNA Analysis and Cell Sorting. Proc. Solid-State Sensor and Actuator Workshop, Hilton Head, SC. Jun. 8-11, 1998; 11-14.
Tawfik, et al. Man-made cell-like compartments for molecular evolution. Nat Biotechnol. Jul. 1998;16(7):652-6.
Mazutis, et al. Selective droplet coalescence using microfluidic systems. Lab Chip. Apr. 24, 2012;12(10):1800-6. doi: 10.1039/c2lc40121e. Epub Mar. 27, 2012.
U.S. Appl. No. 14/624,468, filed Feb. 17, 2015, Hindson et al.
U.S. Appl. No. 14/624,473, filed Feb. 17, 2015, Hindson et al.
U.S. Appl. No. 14/624,484, filed Feb. 17, 2015, Hindson et al.
Office action dated Jan. 15, 2015 for U.S. Appl. No. 14/250,701.
U.S. Appl. No. 14/680,808, filed Apr. 7, 2015, Hindson et al.

(Continued)

*Primary Examiner* — Karen S Weiler
(74) *Attorney, Agent, or Firm* — Wilson Sonsini Goodrich & Rosati

(57) ABSTRACT

The present disclosure provides compositions, methods, systems, and devices for polynucleotide processing. Such polynucleotide processing may be useful for a variety of applications, including polynucleotide sequencing. In some cases, this disclosure provides methods for the generation of polynucleotide barcode libraries, and for the attachment of such polynucleotides to target polynucleotides.

40 Claims, 39 Drawing Sheets

(56) References Cited

U.S. PATENT DOCUMENTS

| | | |
|---|---|---|
| 7,041,481 B2 | 5/2006 | Anderson et al. |
| 7,129,091 B2 | 10/2006 | Ismagilov et al. |
| 7,268,167 B2 | 9/2007 | Higuchi et al. |
| 7,282,370 B2 | 10/2007 | Bridgham et al. |
| 7,323,305 B2 | 1/2008 | Leamon et al. |
| 7,425,431 B2 | 9/2008 | Church et al. |
| 7,536,928 B2 | 5/2009 | Kazuno |
| 7,604,938 B2 | 10/2009 | Takahashi et al. |
| 7,622,280 B2 | 11/2009 | Holliger et al. |
| 7,638,276 B2 | 12/2009 | Griffiths et al. |
| 7,645,596 B2 | 1/2010 | Williams et al. |
| 7,666,664 B2 | 2/2010 | Sarofim et al. |
| 7,708,949 B2 | 5/2010 | Stone et al. |
| 7,709,197 B2 | 5/2010 | Drmanac |
| 7,745,178 B2 | 6/2010 | Dong et al. |
| 7,776,927 B2 | 8/2010 | Chu et al. |
| RE41,780 E | 9/2010 | Anderson et al. |
| 7,799,553 B2 | 9/2010 | Mathies et al. |
| 7,842,457 B2 | 11/2010 | Berka et al. |
| 7,901,891 B2 | 3/2011 | Drmanac et al. |
| 7,910,354 B2 | 3/2011 | Drmanac et al. |
| 7,960,104 B2 | 6/2011 | Drmanac et al. |
| 7,968,287 B2 | 6/2011 | Griffiths et al. |
| 7,972,778 B2 | 7/2011 | Brown et al. |
| 8,003,312 B2 | 8/2011 | Krutzik et al. |
| 8,067,159 B2 | 11/2011 | Brown et al. |
| 8,133,719 B2 | 3/2012 | Drmanac et al. |
| 8,252,539 B2 | 8/2012 | Quake et al. |
| 8,268,564 B2 | 9/2012 | Roth et al. |
| 8,273,573 B2 | 9/2012 | Ismagilov et al. |
| 8,278,071 B2 | 10/2012 | Brown et al. |
| 8,304,193 B2 | 11/2012 | Ismagilov et al. |
| 8,329,407 B2 | 12/2012 | Ismagilov et al. |
| 8,337,778 B2 | 12/2012 | Stone et al. |
| 8,603,749 B2 | 12/2013 | Gillevet |
| 8,748,094 B2 | 6/2014 | Weitz et al. |
| 8,748,102 B2 | 6/2014 | Berka et al. |
| 8,765,380 B2 | 7/2014 | Berka et al. |
| 8,822,148 B2 | 9/2014 | Ismagliov et al. |
| 8,871,444 B2 | 10/2014 | Griffiths et al. |
| 8,889,083 B2 | 11/2014 | Ismagilov et al. |
| 9,017,948 B2 | 4/2015 | Agresti et al. |
| 9,029,083 B2 | 5/2015 | Griffiths et al. |
| 2001/0020588 A1 | 9/2001 | Adourian et al. |
| 2001/0044109 A1 | 11/2001 | Mandecki |
| 2002/0034737 A1 | 3/2002 | Drmanac |
| 2002/0051992 A1 | 5/2002 | Bridgham et al. |
| 2002/0089100 A1 | 7/2002 | Kawasaki |
| 2002/0092767 A1 | 7/2002 | Bjornson et al. |
| 2002/0179849 A1 | 12/2002 | Maher et al. |
| 2003/0008285 A1 | 1/2003 | Fischer |
| 2003/0008323 A1 | 1/2003 | Ravkin et al. |
| 2003/0028981 A1 | 2/2003 | Chandler et al. |
| 2003/0039978 A1 | 2/2003 | Hannah |
| 2003/0044777 A1 | 3/2003 | Beattie |
| 2003/0044836 A1 | 3/2003 | Levine et al. |
| 2003/0104466 A1 | 6/2003 | Knapp et al. |
| 2003/0108897 A1 | 6/2003 | Drmanac |
| 2003/0170698 A1 | 9/2003 | Gascoyne et al. |
| 2003/0182068 A1 | 9/2003 | Battersby et al. |
| 2003/0207260 A1 | 11/2003 | Trnovsky et al. |
| 2003/0215862 A1 | 11/2003 | Parce et al. |
| 2004/0063138 A1 | 4/2004 | McGinnis et al. |
| 2004/0132122 A1 | 7/2004 | Banerjee et al. |
| 2004/0258701 A1 | 12/2004 | Dominowski et al. |
| 2005/0019839 A1 | 1/2005 | Jesperson et al. |
| 2005/0042625 A1 | 2/2005 | Schmidt et al. |
| 2005/0079510 A1 | 4/2005 | Berka et al. |
| 2005/0130188 A1 | 6/2005 | Walt et al. |
| 2005/0172476 A1 | 8/2005 | Stone et al. |
| 2005/0181379 A1 | 8/2005 | Su et al. |
| 2005/0221339 A1 | 10/2005 | Griffiths et al. |
| 2005/0244850 A1 | 11/2005 | Huang et al. |
| 2005/0287572 A1 | 12/2005 | Mathies et al. |
| 2006/0020371 A1 | 1/2006 | Ham et al. |
| 2006/0073487 A1 | 4/2006 | Oliver et al. |
| 2006/0078888 A1 | 4/2006 | Griffiths et al. |
| 2006/0153924 A1 | 7/2006 | Griffiths et al. |
| 2006/0163385 A1 | 7/2006 | Link et al. |
| 2006/0199193 A1 | 9/2006 | Koo et al. |
| 2006/0240506 A1 | 10/2006 | Kushmaro et al. |
| 2006/0257893 A1 | 11/2006 | Takahashi et al. |
| 2006/0263888 A1 | 11/2006 | Fritz et al. |
| 2006/0292583 A1 | 12/2006 | Schneider et al. |
| 2007/0003442 A1 | 1/2007 | Link et al. |
| 2007/0020617 A1 | 1/2007 | Trnovsky et al. |
| 2007/0054119 A1 | 3/2007 | Garstecki et al. |
| 2007/0077572 A1 | 4/2007 | Tawfik et al. |
| 2007/0092914 A1 | 4/2007 | Griffiths et al. |
| 2007/0099208 A1 | 5/2007 | Drmanac et al. |
| 2007/0154903 A1 | 7/2007 | Marla et al. |
| 2007/0172873 A1 | 7/2007 | Brenner et al. |
| 2007/0195127 A1 | 8/2007 | Ahn et al. |
| 2007/0207060 A1 | 9/2007 | Zou et al. |
| 2007/0228588 A1 | 10/2007 | Noritomi et al. |
| 2007/0264320 A1 | 11/2007 | Lee et al. |
| 2008/0003142 A1 | 1/2008 | Link et al. |
| 2008/0004436 A1 | 1/2008 | Tawfik et al. |
| 2008/0014589 A1 | 1/2008 | Link et al. |
| 2008/0213766 A1 | 9/2008 | Brown et al. |
| 2008/0241820 A1 | 10/2008 | Krutzik et al. |
| 2009/0005252 A1 | 1/2009 | Drmanac et al. |
| 2009/0011943 A1 | 1/2009 | Drmanac et al. |
| 2009/0012187 A1 | 1/2009 | Chu et al. |
| 2009/0025277 A1 | 1/2009 | Takanashi |
| 2009/0035770 A1 | 2/2009 | Mathies et al. |
| 2009/0048124 A1 | 2/2009 | Leamon et al. |
| 2009/0053169 A1 | 2/2009 | Castillo et al. |
| 2009/0068170 A1 | 3/2009 | Weitz et al. |
| 2009/0098555 A1 | 4/2009 | Roth et al. |
| 2009/0118488 A1 | 5/2009 | Drmanac et al. |
| 2009/0137404 A1 | 5/2009 | Drmanac et al. |
| 2009/0137414 A1 | 5/2009 | Drmanac et al. |
| 2009/0143244 A1 | 6/2009 | Bridgham et al. |
| 2009/0155781 A1 | 6/2009 | Drmanac et al. |
| 2009/0197248 A1 | 8/2009 | Griffiths et al. |
| 2009/0197772 A1 | 8/2009 | Griffiths et al. |
| 2009/0202984 A1 | 8/2009 | Cantor |
| 2009/0264299 A1 | 10/2009 | Drmanac et al. |
| 2009/0286687 A1 | 11/2009 | Dressman et al. |
| 2010/0021973 A1* | 1/2010 | Makarov ............... C12P 19/34 435/91.21 |
| 2010/0021984 A1 | 1/2010 | Edd et al. |
| 2010/0022414 A1 | 1/2010 | Link et al. |
| 2010/0069263 A1 | 3/2010 | Shendure et al. |
| 2010/0105112 A1 | 4/2010 | Holtz et al. |
| 2010/0130369 A1 | 5/2010 | Shenderov et al. |
| 2010/0136544 A1 | 6/2010 | Agresti et al. |
| 2010/0137163 A1 | 6/2010 | Link et al. |
| 2010/0173394 A1 | 7/2010 | Colston, Jr. et al. |
| 2010/0210479 A1 | 8/2010 | Griffiths et al. |
| 2011/0033854 A1 | 2/2011 | Drmanac et al. |
| 2011/0071053 A1 | 3/2011 | Drmanac et al. |
| 2011/0086780 A1 | 4/2011 | Colston, Jr. et al. |
| 2011/0092376 A1 | 4/2011 | Colston, Jr. et al. |
| 2011/0092392 A1 | 4/2011 | Colston, Jr. et al. |
| 2011/0160078 A1 | 6/2011 | Fodor et al. |
| 2011/0195496 A1 | 8/2011 | Muraguchi et al. |
| 2011/0201526 A1 | 8/2011 | Berka et al. |
| 2011/0217736 A1 | 9/2011 | Hindson |
| 2011/0218123 A1 | 9/2011 | Weitz et al. |
| 2011/0263457 A1 | 10/2011 | Krutzik et al. |
| 2011/0267457 A1 | 11/2011 | Weitz et al. |
| 2011/0281738 A1 | 11/2011 | Drmanac et al. |
| 2011/0305761 A1 | 12/2011 | Shum et al. |
| 2011/0319281 A1 | 12/2011 | Drmanac |
| 2012/0000777 A1 | 1/2012 | Garrell et al. |
| 2012/0010098 A1 | 1/2012 | Griffiths et al. |
| 2012/0010107 A1 | 1/2012 | Griffiths et al. |
| 2012/0015382 A1 | 1/2012 | Weitz et al. |
| 2012/0015822 A1 | 1/2012 | Weitz et al. |
| 2012/0071331 A1 | 3/2012 | Casbon et al. |
| 2012/0121481 A1 | 5/2012 | Romanowsky et al. |
| 2012/0132288 A1 | 5/2012 | Weitz et al. |

(56) References Cited

U.S. PATENT DOCUMENTS

| | | | |
|---|---|---|---|
| 2012/0135893 A1 | 5/2012 | Drmanac et al. | |
| 2012/0172259 A1 | 7/2012 | Rigatti et al. | |
| 2012/0190032 A1 | 7/2012 | Ness et al. | |
| 2012/0196288 A1* | 8/2012 | Beer ............... | B01L 3/502761 435/6.12 |
| 2012/0211084 A1 | 8/2012 | Weitz et al. | |
| 2012/0220494 A1 | 8/2012 | Samuels et al. | |
| 2012/0220497 A1 | 8/2012 | Jacobson et al. | |
| 2012/0222748 A1 | 9/2012 | Weitz et al. | |
| 2012/0309002 A1 | 12/2012 | Link | |
| 2012/0316074 A1 | 12/2012 | Saxonov | |
| 2013/0028812 A1 | 1/2013 | Prieto et al. | |
| 2013/0046030 A1 | 2/2013 | Rotem et al. | |
| 2013/0078638 A1 | 3/2013 | Berka et al. | |
| 2013/0079231 A1 | 3/2013 | Pushkarev et al. | |
| 2013/0109575 A1 | 5/2013 | Kleinschmidt et al. | |
| 2013/0157899 A1 | 6/2013 | Adler, Jr. et al. | |
| 2013/0178368 A1 | 7/2013 | Griffiths et al. | |
| 2013/0189700 A1 | 7/2013 | So et al. | |
| 2013/0210639 A1 | 8/2013 | Link et al. | |
| 2013/0225418 A1 | 8/2013 | Watson | |
| 2013/0274117 A1* | 10/2013 | Church ............... | C12Q 1/6869 506/4 |
| 2014/0037514 A1 | 1/2014 | Stone et al. | |
| 2014/0057799 A1 | 2/2014 | Johnson et al. | |
| 2014/0065234 A1 | 3/2014 | Shum et al. | |
| 2014/0155295 A1 | 6/2014 | Hindson et al. | |
| 2014/0194323 A1 | 7/2014 | Gillevet | |
| 2014/0199730 A1 | 7/2014 | Agresti et al. | |
| 2014/0199731 A1 | 7/2014 | Agresti et al. | |
| 2014/0206554 A1 | 7/2014 | Hindson et al. | |
| 2014/0227684 A1 | 8/2014 | Hindson et al. | |
| 2014/0227706 A1 | 8/2014 | Kato et al. | |
| 2014/0235506 A1 | 8/2014 | Hindson et al. | |
| 2014/0378322 A1 | 12/2014 | Hindson et al. | |
| 2014/0378345 A1 | 12/2014 | Hindson et al. | |
| 2014/0378349 A1 | 12/2014 | Hindson et al. | |
| 2014/0378350 A1 | 12/2014 | Hindson et al. | |
| 2015/0005199 A1 | 1/2015 | Hindson et al. | |
| 2015/0005200 A1 | 1/2015 | Hindson et al. | |
| 2015/0011430 A1 | 1/2015 | Saxonov | |
| 2015/0011432 A1 | 1/2015 | Saxonov | |
| 2015/0111256 A1 | 4/2015 | Church et al. | |
| 2015/0218633 A1 | 8/2015 | Hindson et al. | |
| 2015/0224466 A1 | 8/2015 | Hindson et al. | |
| 2015/0225777 A1 | 8/2015 | Hindson et al. | |
| 2015/0225778 A1 | 8/2015 | Hindson et al. | |
| 2015/0292988 A1 | 10/2015 | Bharadwaj et al. | |

FOREIGN PATENT DOCUMENTS

| | | | |
|---|---|---|---|
| EP | 1019496 B1 | 9/2004 | |
| EP | 1482036 B1 | 10/2007 | |
| EP | 1594980 B1 | 11/2009 | |
| EP | 1967592 B1 | 4/2010 | |
| EP | 2258846 A2 | 12/2010 | |
| EP | 2145955 B1 | 2/2012 | |
| EP | 1905828 B1 | 8/2012 | |
| EP | 2136786 B1 | 10/2012 | |
| EP | 1908832 B1 | 12/2012 | |
| EP | 2540389 A1 | 1/2013 | |
| GB | 2485850 A | 5/2012 | |
| JP | 5949832 A | 3/1984 | |
| JP | 2006-507921 A | 3/2006 | |
| JP | 2006-289250 A | 10/2006 | |
| JP | 2007-268350 A | 10/2007 | |
| JP | 2009-208074 A | 9/2009 | |
| WO | WO 96/29629 A2 | 3/1996 | |
| WO | WO 96/41011 A1 | 12/1996 | |
| WO | WO 99/09217 A1 | 2/1999 | |
| WO | WO 99/52708 A1 | 10/1999 | |
| WO | WO 00/08212 A1 | 2/2000 | |
| WO | WO 00/26412 A1 | 5/2000 | |
| WO | WO 01/14589 A2 | 3/2001 | |
| WO | WO 01/89787 A2 | 11/2001 | |
| WO | WO 02/31203 A2 | 4/2002 | |
| WO | WO 02/086148 A1 | 10/2002 | |
| WO | WO 2004/002627 A2 | 1/2004 | |
| WO | WO 2004/010106 A2 | 1/2004 | |
| WO | WO 2004/091763 A2 | 10/2004 | |
| WO | WO 2004/102204 A1 | 11/2004 | |
| WO | WO 2004/103565 A2 | 12/2004 | |
| WO | WO 2004/105734 A1 | 12/2004 | |
| WO | WO 2005/082098 A2 | 2/2005 | |
| WO | WO 2005/021151 A1 | 3/2005 | |
| WO | WO 2005/023331 A2 | 3/2005 | |
| WO | WO 2005/040406 A1 | 5/2005 | |
| WO | WO 2005/049787 A2 | 6/2005 | |
| WO | WO 2006/030993 A1 | 3/2006 | |
| WO | WO 2006/078841 A1 | 7/2006 | |
| WO | WO 2006/096571 A2 | 9/2006 | |
| WO | WO 2007/001448 A2 | 1/2007 | |
| WO | WO 2007/002490 A2 | 1/2007 | |
| WO | WO 2007/024840 A2 | 3/2007 | |
| WO | WO 2007/081385 A2 | 7/2007 | |
| WO | WO 2007/081387 A1 | 7/2007 | |
| WO | WO 2007/089541 A2 | 8/2007 | |
| WO | WO 2007/114794 A1 | 10/2007 | |
| WO | WO 2007/121489 A2 | 10/2007 | |
| WO | WO 2007/133710 A2 | 11/2007 | |
| WO | WO 2007/138178 A2 | 12/2007 | |
| WO | WO 2007/139766 A2 | 12/2007 | |
| WO | WO 2007/140015 A2 | 12/2007 | |
| WO | WO 2007/149432 A2 | 12/2007 | |
| WO | WO 2008/091792 A2 | 1/2008 | |
| WO | WO 2008/021123 A1 | 2/2008 | |
| WO | WO 2008/102057 A1 | 8/2008 | |
| WO | WO 2008/109176 A2 | 9/2008 | |
| WO | WO 2008/121342 A2 | 10/2008 | |
| WO | WO 2008/134153 A1 | 11/2008 | |
| WO | WO 2009/005680 A1 | 1/2009 | |
| WO | WO 2009/011808 A1 | 1/2009 | |
| WO | WO 2009/061372 A1 | 5/2009 | |
| WO | WO 2009/085215 A1 | 7/2009 | |
| WO | WO 2010/004018 A2 | 1/2010 | |
| WO | WO 2010/033200 A2 | 3/2010 | |
| WO | WO 2010/148039 A2 | 12/2010 | |
| WO | WO 2010/151776 A2 | 12/2010 | |
| WO | WO 2011/047870 A1 | 4/2011 | |
| WO | WO 2011/056546 A1 | 5/2011 | |
| WO | WO 2011/066476 A1 | 6/2011 | |
| WO | WO 2012012037 A1 * | 1/2012 | ........... C12Q 1/6813 |
| WO | WO 2012/048341 A1 | 4/2012 | |
| WO | WO 2012/083225 A2 | 6/2012 | |
| WO | WO 2012/149042 A2 | 11/2012 | |
| WO | WO 2012/166425 A2 | 12/2012 | |
| WO | WO 2013/177220 A1 | 11/2013 | |
| WO | WO 2014/028537 A1 | 2/2014 | |

OTHER PUBLICATIONS

Gyarmati, et al. Reversible disulphide formation in polymer networks: a versatile functional group from synthesis to applications. European Polymer Journal. 2013;49:1268-1286.
Office action dated Apr. 20, 2015 for U.S. Appl. No. 13/966,150.
International search report and written opinion dated May 14, 2015 for PCT/US2014/044398.
U.S. Appl. No. 14/682,952, filed Apr. 8, 2015, Bharadwaj et al.
International search report and written opinion dated Aug. 19, 2015 for PCT/US2015/025197.
Hug, et al. Measurement of the number of molecules of a single mRNA species in a complex mRNA preparation. J Theor Biol. Apr. 21, 2003;221(4):615-24.
Office action dated Sep. 10, 2014 for U.S. Appl. No. 14/250,701.
International search report and written opinion dated Aug. 20, 2014 for PCT/US2014/015424.
U.S. Appl. No. 14/316,383, filed Jun. 26, 2014, Hindson et al.
U.S. Appl. No. 14/316,398, filed Jun. 26, 2014, Hindson et al.
U.S. Appl. No. 14/316,416, filed Jun. 26, 2014, Hindson et al.
U.S. Appl. No. 14/316,431, filed Jun. 26, 2014, Hindson et al.
U.S. Appl. No. 14/316,447, filed Jun. 26, 2014, Hindson et al.

(56) References Cited

OTHER PUBLICATIONS

U.S. Appl. No. 14/316,463, filed Jun. 26, 2014, Hindson et al.
Advisory Action dated Mar. 21, 2014 for U.S. Appl. No. 13/119,470.
Advisory Action dated May 16, 2014 for U.S. Appl. No. 13/503,588.
Australian Office Action issued Dec. 17, 2013 for Application No. AU 2010315580.
Boone, et al. Plastic advances microfluidic devices. The devices debuted in silicon and glass, but plastic fabrication may make them hugely successful in biotechnology application. Analytical Chemistry. Feb. 2002; 78A-86A.
Fisher, et al. A scalable, fully automated process for construction of sequence-ready human exome targeted capture libraries. Genome Biol. 2011;12(1):R1. doi: 10.1186/gb-2011-12-1-rl. Epub Jan. 4, 2011.
Gartner, et al. The Microfluidic Toolbox—examples for fluidic interfaces and standardization concepts. Proc. SPIE 4982, Microfluidics, BioMEMS, and Medical Microsystems, (Jan. 17, 2003); doi: 10.1117/12.479566.
Ghadessy, et al. Directed evolution of polymerase function by compartmentalized self-replication. Proc Natl Acad Sci U S A. Apr. 10, 2001;98(8):4552-7. Epub Mar. 27, 2001.
International search report and written opinion dated May 14, 2014 for PCT/US2014/015427.
International search report and written opinion dated May 16, 2014 for PCT/US2013/074764.
Japanese Final Rejection dated Aug. 5, 2014 for Application No. JP 2012-536941.
Microfluidic ChipShop. Microfluidic product catalogue. Mar. 2005.
Microfluidic ChipShop. Microfluidic product catalogue. Oct. 2009.
Notice of Allowance dated Jan. 27, 2014 for U.S Appl. No. 13/139,326.
Office action dated Feb. 10, 2014 for U.S. Appl. No. 13/503,588.
Office action dated May 20, 2014 for U.S. Appl. No. 14/172,266.
Office action dated May 20, 2014 for U.S. Appl. No. 14/172,326.
Office action dated May 28, 2013 for U.S. Appl. No. 12/529,926.
Office action dated Jul. 30, 2014 for U.S. Appl. No. 12/809,120.
Office action dated Aug. 6, 2014 for U.S. Appl. No. 12/529,926.
Office action dated Oct. 1, 2012 for U.S. Appl. No. 12/529,926.
Office action dated Dec. 5, 2013 for U.S. Appl. No. 13/119,470.
Office Action mailed Apr. 29, 2014 for EP Application No. 08865992.5.
Office Action mailed Dec. 16, 2013 for CN Application No. 201080055990.9.
Office Action mailed May 23, 2013 for CN Application No. 200880127116.4.
U.S. Appl. No. 13/966,150, filed Aug. 13, 2013, Hindson et al.
U.S. Appl. No. 14/104,650, filed Dec. 12, 2013, Hindson et al.
U.S. Appl. No. 14/175,935, filed Feb. 7, 2014, Hindson et al.
Abate et al., Valve-based flow focusing for drog formation. Appl Phys Lett. 2009;94. 3 pages.
Abate, et al. High-throughput injection with microfluidics using picoinjectors. Proc Natl Acad Sci U S A. Nov. 9, 2010;107(45):19163-6. doi: 10.1073/pNas.1006888107. Epub Oct. 20, 2010.
Advisory Action mailed Nov. 20, 2013 for U.S. Appl. No. 13/139,326.
Agresti, et al. Selection of ribozymes that catalyse multiple-turnover Diels-Alder cycloadditions by using in vitro compartmentalization. Proc Natl Acad Sci U S A. Nov. 8, 2005;102(45):16170-5. Epub Oct. 31, 2005.
Akselband, "Enrichment of slow-growing marine microorganisms from mixed cultures using gel microdrop (GMD) growth assay and fluorescence-activated cell sorting", J. Exp. Marine Bioi., 329: 196-205 (2006).
Akselband, "Rapid mycobacteria drug susceptibility testing using gel microdrop (GMD) growth assay and flow cytometry", J. Microbiol. Methods, 62:181-197 (2005).
Anna et al., "Formation of dispersions using 'flow focusing' in microchannels", Appln. Phys. Letts. 82:3 364 (2003).

Braeckmans et al., Scanning the Code. Modern Drug Discovery. 2003:28-32.
Bransky, et al. A microfluidic droplet generator based on a piezoelectric actuator. Lab Chip. Feb. 21, 2009;9(4):516-20. doi: 10.1039/b814810d. Epub Nov. 20, 2008.
Carroll, "The selection of high-producing cell lines using flow cytometry and cell sorting", Exp. Op. Bioi. Therp., 4:11 1821-1829 (2004).
Chaudhary "A rapid method of cloning functioNal variable-region antibody genese in Escherichia coli as single-chain immunotoxins" Proc. Nat!. Acad. Sci USA 87: 1066-1070 (Feb. 1990).
Chechetkin et al., Sequencing by hybridization with the generic 6-mer oligonucleotide microarray: an advanced scheme for data processing. J Biomol Struct Dyn. Aug. 2000;18(1):83-101.
Chinese Office Action and search report mailed May 23, 2013 for Application No. CN 200880127116.4.
Chinese office action dated Jun. 18, 2012 for CN Application No. 200880127116.4.
Clausell-Tormos et al., "Droplet-based microfluidic platforms for the encapsulation and screening of mammalian cells and multicellular organisms", Chem. Biol. 15:427-437 (2008).
De Bruin et al., UBS Investment Research. Q-Series®: DNa Sequencing. UBS Securities LLC. Jul. 12, 2007. 15 pages.
Demirci, et al. Single cell epitaxy by acoustic picolitre droplets. Lab Chip. Sep. 2007;7(9):1139-45. Epub Jul. 10, 2007.
Doerr, "The smallest bioreactor", Nature Methods, 2:5 326 (2005).
Dowding, et al. Oil core/polymer shell microcapsules by interNal phase separation from emulsion droplets. II: controlling the release profile of active molecules. Langmuir. Jun. 7, 2005;21(12):5278-84.
Drmanac et al., Sequencing by hybridization (SBH): advantages, achievements, and opportunities. Adv Biochem Eng Biotechnol. 2002;77 :75-101.
Droplet Based Sequencing (slides) dated (Mar. 12, 2008).
Esser-Kahn, et al. Triggered release from polymer capsules. Macromolecules. 2011; 44:5539-5553.
European office action dated Jan. 23, 2012 for Application No. EP 08865992.5.
European office action dated Apr. 5, 2013 for Application No. EP 08865992.5.
European office action dated Aug. 29, 2013 for Application No. EP 08865992.5.
European office action dated Dec. 15, 2010 for EP Application No. 08865992.5.
Freiberg, et al. Polymer microspheres for controlled drug release. Int J Pharm. Sep. 10, 2004;282(1-2):1-18.
Fu, "A micro fabricated fluorescence-activated cell sorter", Nature Biotech., 17:1109-1111 (1997).
Fulton et al., Advanced multiplexed analysis with the FlowMetrix system. Clin Chern. Sep. 1997;43(9): 1749-56.
Garstecki, et al. Formation of monodisperse bubbles in a microfluidic flow-focusing device. Applied Physics Letters. 2004; 85(13):2649-2651. DOI: 10.1063/1.1796526.
Hashimshony, et al. CEL-Seq: Single-Cell RNa-Seq by Multiplexed Linear Amplification. Cell Rep. Sep. 27, 2012;2(3):666-73. doi: 10.1016/j.celrep.2012.08.003. Epub Aug. 30, 2012.
He "Selective Encapsulation of Single Cells and Subcellular Organelles into Picoliter- and Femtoliter-Volume Droplets" ANal. Chern 77: 1539-1544 (2005).
Holtze, et al. Biocompatible surfactants for water-in-fluorocarbon emulsions. Lab Chip. Oct. 2008;8(10):1632-9. doi: 10.1039/b806706f. Epub Sep. 2, 2008.
Huebner, "Quantitative detection of protein expression in single cells using droplet microfluidics", Chern. Commun 1218-1220 (2007).
International Preliminary Report on Patentability dated Mar. 31, 2011 for PCT/US09/005184.
International Preliminary Report on Patentability dated May 10, 2012 for PCT/US2010/054050.
International Preliminary Report on Patentability dated Jun. 30, 2011 for PCT/US2009/006649.
International Preliminary Report on Patentability dated Jul. 1, 2010 for PCT/US2008/013912.
International Preliminary Report on Patentability dated Sep. 17, 2009 for PCT/US2008/003185 mailed Sep. 17, 2009.

(56) References Cited

OTHER PUBLICATIONS

International search report and written opinion dated Jan. 12, 2009 for PCT/US2008/003185.
International search report and written opinion dated Jan. 31, 2011 for PCT/US2010/054050.
International search report and written opinion dated Apr. 3, 2009 for PCT/US2008/013912.
International search report and written opinion dated Aug. 16, 2010 for PCT/US2009/005184.
International search report and written opinion dated Oct. 2, 2009 for PCT/US2009/004037.
International search report and written opinion dated Oct. 21, 2009 for PCT/US2009/003389.
International search report and written opinion dated Oct. 29, 2008 for PCT/US2008/008563.
International search report and written opinion dated Dec. 16, 2013 for PCT/US2013/054797.
International search report dated Apr. 22, 2009 for PCT/US2009/000664.
Japanese Office Action and mailed Jul. 17, 2013 for Application No. JP 2010-539498.
Japanese Office Action mailed Nov. 19, 2013 for Application No. JP 2012-536941.
Khomiakov A et al., [Analysis of perfect and mismatched DNA duplexes by a generic hexanucleotide microchip]. Mol Bioi (Mosk). Jul.-Aug. 2003;37(4):726-41. Russian. Abstract only.
Kim, et al. Albumin loaded microsphere of amphiphilic poly(ethylene glycol)/ poly(alpha-ester) multiblock copolymer. Eur J Pharm Sci. Nov. 2004;23(3):245-51.
Kim, et al. Fabrication of monodisperse gel shells and functioNal microgels in microfluidic devices. Angew Chem Int Ed Engl. 2007;46(11):1819-22.
Koster et al., "Drop-based microfluidic devices for encapsulation of single cells", Lab on a Chip The Royal Soc. of Chern. 8: 1110-1115 (2008).
Kutyavin, et al. Oligonucleotides containing 2-aminoadenine and 2-thiothymine act as selectively binding complementary agents. Biochemistry. Aug. 27, 1996;35(34):11170-6.
Li, Y., et al., "PEGylated PLGA Nanoparticles as protein carriers: synthesis, preparation and biodistribution in rats," JourNal of Controlled Release, vol. 71, pp. 203-211 (2001).
Liu, et al. Preparation of uniform-sized PLA microcapsules by combining Shirasu porous glass membrane emulsification technique and multiple emulsion-solvent evaporation method. J Control Release. Mar. 2, 2005;103(1):31-43. Epub Dec. 21, 2004.
Liu, et al. Smart thermo-triggered squirting capsules for Nanoparticle delivery. Soft Matter. 2010; 6(16):3759-3763.
Loscertales, I.G., et al., "Micro/Nano Encapsulation via Electrified Coaxial Liquid Jets," Science, vol. 295, pp. 1695-1698 (2002).
Love, "A microengraving method for rapid selection of single cells producing antigen-specific antibodies", Nature Biotech, 24:6 703 (Jun. 2006).
Marcus. Gene method offers diagnostic hope. The Wall Street JourNal. Jul. 11, 2012.
Merriman, et al. Progress in ion torrent semiconductor chip based sequencing. Electrophoresis. Dec. 2012;33(23):3397-417. doi: 10.1002/elps.201200424.
Mirzabekov, "DNA Sequencing by Hybridization—a Megasequencing Method and a Diagnostic Tool?" Trends in Biotechnology 12(1): 27-32 (1994).
Mouritzen et al., Single nucleotide polymorphism genotyping using locked nucleic acid (LNa). Expert Rev Mol Diagn. Jan. 2003;3(1):27-38.
Nguyen, et al. In situ hybridization to chromosomes stabilized in gel microdrops. Cytometry. 1995; 21:111-119.
Oberholzer, et al. Polymerase chain reaction in liposomes. Chem Biol. Oct. 1995;2(10):677-82.
Office action dated Jan. 4, 2010 for U.S. Appl. No. 12/172,186.
Office action dated Feb. 28, 2013 for U.S. Appl. No. 13/139,326.
Office action dated Apr. 24, 2013 for U.S. Appl. No. 13/119,470.
Office action dated Aug. 6, 2013 for U.S. Appl. No. 13/139,326.
Office action dated Sep. 17, 2013 for U.S. Appl. No. 13/503,588.
Ogawa, et al. Production and characterization of O/W emulsions containing cationic droplets stabilized by lecithin-chitosan membranes. J Agric Food Chem. Apr. 23, 2003;51(9):2806-12.
Okushima, "Controlled production of monodisperse double emulsions by two-step droplet breakup in microfluidic devices", Langmuir, 20:9905-9908 (2004).
Perez, C., et al., "Poly(lactic acid)-poly(ethylene glycol) Nanoparticles as new carriers for the delivery ofplasmid DNa," JourNal of Controlled Release, vol. 75, pp. 211-224 (2001).
Peters, et al. Accurate whole-genome sequencing and haplotyping from 10 to 20 human cells. Nature. Jul. 11, 2012;487(7406):190-5. doi: 10.1038/Nature11236.
Plunkett, et al. Chymotrypsin responsive hydrogel: application of a disulfide exchange protocol for the preparation of methacrylamide containing peptides. Biomacromolecules. Mar.-Apr. 2005;6(2):632-7.
Ryan, et al. Rapid assay for mycobacterial growth and antibiotic susceptibility using gel microdrop encapsulation. J Clin Microbiol. Jul. 1995;33(7):1720-6.
Schirinzi et al., Combinatorial sequencing-by-hybridization: aNalysis of the NFl gene. Genet Test. 2006 Spring;10(1):8-17.
Schmitt, "Bead-based multiplex genotyping of human papillomaviruses", J. Clinical Microbial., 44:2 504-512 (2006).
Shah, "Fabrication of mono disperse thermosensitive microgels and gel capsules in micro fluidic devices", Soft Matter, 4:2303-2309 (2008).
Simeonov et al., Single nucleotide polymorphism genotyping using short, fluorescently labeled locked nucleic acid (LNa) probes and fluorescence polarization detection. Nucleic Acids Res. Sep. 1, 2002;30(17):e91.
Sorokin et al., DiscrimiNation between perfect and mismatched duplexes with oligonucleotide gel microchips: role of thermodyNamic and kinetic effects during hybridization. J Biomol Struct Dyn. Jun. 2005;22(6):725-34.
Su, et al., Microfluidics-Based Biochips: Technology Issues, Implementation Platforms, and Design-Automation Challenges. IEEE Transactions on Computer-Aided Design of Integrated Circuits and Systems. 2006;25(2):211-23. (Feb. 2006).
Sun et al., Progress in research and application of liquid-phase chip technology. Chinese JourNal Experimental Surgery. May 2005;22(5):639-40.
Theberge, et al. Microdropelts in microfluidics: an evolving platform for discoveries in chemsitry and biology. Angew Chem Int Ed Engl. Aug. 9, 2010;49(34):5846-68. doi: 10.1002/anie.200906653.
Tubeleviciute, et al. Compartmentalized self-replication (CSR) selection of Thermococcus litoralis Sh1B DNa polymerase for diminished uracil binding. Protein Eng Des Sel. Aug. 2010;23(8):589-97. doi: 10.1093/protein/gzq032. Epub May 31, 2010.
Wang et al., Single nucleotide polymorphism discrimiNation assisted by improved base stacking hybridization using oligonucleotide microarrays. Biotechniques. 2003;35:300-08.
Wang, et al. A novel thermo-induced self-bursting microcapsule with magnetic-targeting property. Chemphyschem. Oct. 5, 2009;10(14):2405-9.
Weaver, "Rapid clonal growth measurements at the single-cell level: gel microdroplets and flow cytometry", Biotechnology, 9:873-877 (1991).
Whitesides, "Soft lithography in biology and biochemistry", Annual Review of Biomedical Engineering, 3:335-373 (2001).
Williams, et al. Amplification of complex gene libraries by emulsion PCR. Nat Methods. Jul. 2006;3(7):545-50.
Woo, et al. G/C-modified oligodeoxynucleotides with selective complementarity: synthesis and hybridization properties. Nucleic Acids Res. Jul. 1, 1996;24(13):2470-5.
Xia, "Soft lithography", Annual Review of Material Science, 28: 153-184 (1998).
Yamamoto, et al. Chemical modification of Ce(IV)/EDTA-base artificial restriction DNa cutter for versatile manipulation of doulbestranded DNa. Nucleic Acids Research. 2007; 35(7):e53.

(56) References Cited

OTHER PUBLICATIONS

Zhang, "Combinatorial marking of cells and organelles with reconstituted fluorescent proteins", Cell, 119:137-144 (Oct. 1, 2004).

Zhang, et al. Degradable disulfide core-cross-linked micelles as a drug delivery system prepared from vinyl functioNalized nucleosides via the RAFT process. Biomacromolecules. Nov. 2008;9(11):3321-31. doi: 10.1021/bm800867n. Epub Oct. 9, 2008.

Zhao, J., et al., "Preparation of hemoglobin-loaded Nano-sized particles with porous structure as oxygen carriers," Biomaterials, vol. 28, pp. 1414-1422 (2007).

Zimmermann et at., Microscale production of hybridomas by hypo-osmolar electrofusion. Hum. Antibodies Hybridomas. Jan. 1992;3(1): 14-8.

Zong, et al. Genome-wide detection of single-nucleotide and copy-number variations of a single human cell. Science. Dec. 21, 2012;338(6114):1622-6. doi: 10.1126/science.1229164.

European search report and opinion dated Feb. 2, 2016 for EP Application No. 13829413.

Office action dated Jan. 29, 2016 for U.S. Appl. No. 14/175,935.
Office action dated Nov. 6, 2015 for U.S. Appl. No. 13/966,150.
Office action dated Oct. 9, 2015 for U.S. Appl. No. 14/680,808.
Office action dated Sep. 25, 2015 for U.S. Appl. No. 14/250,701.
Office action dated Feb. 23, 2016 for U.S. Appl. No. 14/104,650.
Office action dated Mar. 1, 2016 for U.S. Appl. No. 14/250,701.
Office action dated Mar. 14, 2016 for U.S. Appl. No. 14/680,808.

Shimkus, et al. A chemically cleavable biotinylated nucleotide: usefulness in the recovery of protein-DNA complexes from avidin affinity columns Proc Natl Acad Sci U S A. May 1985;82(9):2593-7.

* cited by examiner

Fig. 3

5'-
AATGATACGG CGACCACCGA GATCTACACT     30
AGATCGCACA CTCTTTCCCT ACACGACGCT     60
CTTCCGATCT GATCTAA   SEQ ID NO: 1    77

-NNN-                                    80

TTAGATCAGA TCGGAAGAGC  ACACGTCTGA   110
ACTCCAGTCA CTAAGGCGAA  TCTCGTATGC   140
CGTCTTCTGC TTG                          153
-3'                 SEQ ID NO: 22

SEQ ID NO: 2

Fig. 8a

SEQ ID NO: 3

5'-ACACTCTTTCCCTACACGAC

**GCTCTTCCGATCT
CGAGAAGGCTAG**

3'-CACTGACCTCAAGTCTGCACA

SEQ ID NO: 4

Fig. 8b

SEQ ID NO: 5

5'-ACACTCTTTCCCTACACGAC                                    ACACGTCTGAACTCCAGTCAC
                    GCTCTTCCGATCT<u>111</u>AGATCGGAAGAGC
                    CGAGAAGGCTAG<u>A111</u>TCTAGCCTTCTCG
3'-CACTGACCTCAAGTCTGCACA                                    CAGCACATCCCTTTCTCACA

SEQ ID NO: 6

Fig. 8c

5'-<u>AATGATACGGCGACCACCGAGATCT</u>ACACTCTTTCCCTACACGACGCTCTTCCGATCT<u>111</u>AGATCGGAAGAGCA
CACGTCTGAACTCCAGTCACATCACG<u>ATCTCGTATGCCGTCTTCTGCTTG</u>   (SEQ ID NO: 7)

3' —
<u>TTACTATGCCGCTGGTGGCTCTAGAT</u>GTGAGAAAGGGATGTGCTGCGAGAAGGCTAGA<u>111</u>TCTAGCCTTCTC
GTGTGCAGACTTGAGGTCAGTGTAGTGC<u>TAGAGCATACGGCAGAAGACGAAC</u>   (SEQ ID NO: 8)

Fig. 9a

SEQ ID NO: 9

5'-ACACTCTTTCCCTACACGAC
                                GCTCTTCCGATCTNNNNNNNT
                                CGAGAAGGCTAGANNNNNNNN

3'-CACTGACCTCAAGTCTGCACA

SEQ ID NO: 10

Fig. 9b

5'-
NNNNNNNNAGATCGGAAGAGCACACGTCTGAACTCCAGTCAC*ACA
CTCTTTCCCTACACGACGCTCTTCCGATCTNNNNNNNT
(SEQ ID NO: 11)

Fig. 9c

5'-
RRRRRRRRRRRANNNNNNNAGATCGGAAGAGCGTCGTGTAGGG
AAAGAGTGTGTGACTGGAGTTCAGACGTGTGCTCTTCCGATCT
(SEQ ID NO: 12)

Fig. 9d

SEQ ID NO: 12

```
  GTGACTGGAGTTCAGACGTGT
                      GCTCTTCCGATCT — 3'
                      CGAGAAGGCTAGANNNNNNNNARRRRRRRRRRR
  TGTGAGAAAGGGATGTGCTG
```

Fig. 9e

SEQ ID NO: 13

```
  GTGACTGGAGTTCAGACGTGT
                      GCTCTTCCGATCTNNNNNNNNNTNNNNNNNNNNNN — 3'
                      CGAGAAGGCTAGANNNNNNNNARRRRRRRRRRR
  TGTGAGAAAGGGATGTGCTG
```

Fig. 9f

SEQ ID NO: 14

```
  GTGACTGGAGTTCAGACGTGT
                      GCTCTTCCGATCTNNNNNNNNNTNNNNNNNNNNNN — 3'
                      CGAGAAGGCTAGANNNNNNNNA
  TGTGAGAAAGGGATGTGCTG
```

Fig. 9g

5'ANNNNNNNNGATCGGAAGAGCACACGTCTGAACTCCAGTCACACACTCTTTCCCTACACGACGCTCTTCCG
3'TNNNNNNNNCTAGCCTTCTCGTGTGCAGACTTGAGGTCAGTGTGTGAGAAAGGGATGTGCTGCGAGAAGGC

ATCTNNNNNNNNNTNNNNNNNNNNNNN-3' (SEQ ID NO: 15)
TAGANNNNNNNNNRRRRRRRRRRRRR-5' (SEQ ID NO: 16)

Fig. 9h

3'TNNNNNNNNNCTAGCCTTCTCGTGTGCAGACTTGAGGTCAGTGTGTGAGAAAGGGATGTGCTGCGAGAAGGC
TAGANNNNNNNN-5' (SEQ ID NO: 17)

Fig. 9i

5'NNNNNNNNNAGATCGGAAGAGCGTCGTGTAGGGAAAGAGTGTGTGACTGGAGTTCAGACGTGTGCTCTTCCG
ATCNNNNNNNNT-3' (SEQ ID NO: 17)

Fig. 9j

SEQ ID NO: 17

```
 ACACTCTTTCCCTACACGAC
                      GCTCTTCCGATCTNNNNNNNNT — 3'
                      CGAGAAGGCTAGANNNNNNNN
 CACTGACCTCAAGTCTGCACA
```

Fig. 10a

SEQ ID NO: 3
5'-ACACTCTTTCCCTACACGAC
                             GCTCTTCCGATCT
                             CGAGAAGGCTAG
3'-CACTGACCTCAAGTCTGCACA
SEQ ID NO: 4

Fig. 10b

SEQ ID NO: 18

5'-<u>AATGATACGGCGACCACCGAGATCT</u>ACACNNNNNNNNACACTCTTTCCCTACACGAC
                                                                      GCTCTTCCGATCTT
                                                                      CGAGAAGGCTAG
                                                           3'-CACTGACCTCAAGTCTGCACA
                                                                 SEQ ID NO: 4

Fig. 10c

SEQ ID NO: 18

5'- AATGATACGGCGACCACCGAGATCTACACNNNNNNNNACACTCTTTCCCTACACGACGCTCTTCCGATCTT - 3'
3'- TTACTATGCCGCTGGTGGCTCTAGATGTGNNNNNNNNTGTGAGAAAGGGATGTGCTG<u>CGAGAAGGCTAGAA</u> - 5'

SEQ ID NO: 19

Fig. 10d

SEQ ID NO: 18
5'AATGATACGGCGACCACCGAGATCTACACNNNNNNNACACTCTTTCCCTACACGACGCTCTTCCGATCTT-3'
3'TTACTATGCCGCTGGTGGCTCTAGATGTGNNNNNNNTGTGAGAAAGGGATGTGCTG-5'

SEQ ID NO: 20

Fig. 10e

SEQ ID NO: 18
5'AATGATACGGCGACCACCGAGATCTACACNNNNNNNACACTCTTTCCCTACACGAC GCTCTTCCGATCTT-3'
3'TTACTATGCCGCTGGTGGCTCTAGATGTGNNNNNNNTGTGAGAAAGGGATGTGCTG CGAGAAGGCTAGA

SEQ ID NO: 20

3'-CACTGACCTCAAGTCTGCACA

SEQ ID NO: 21

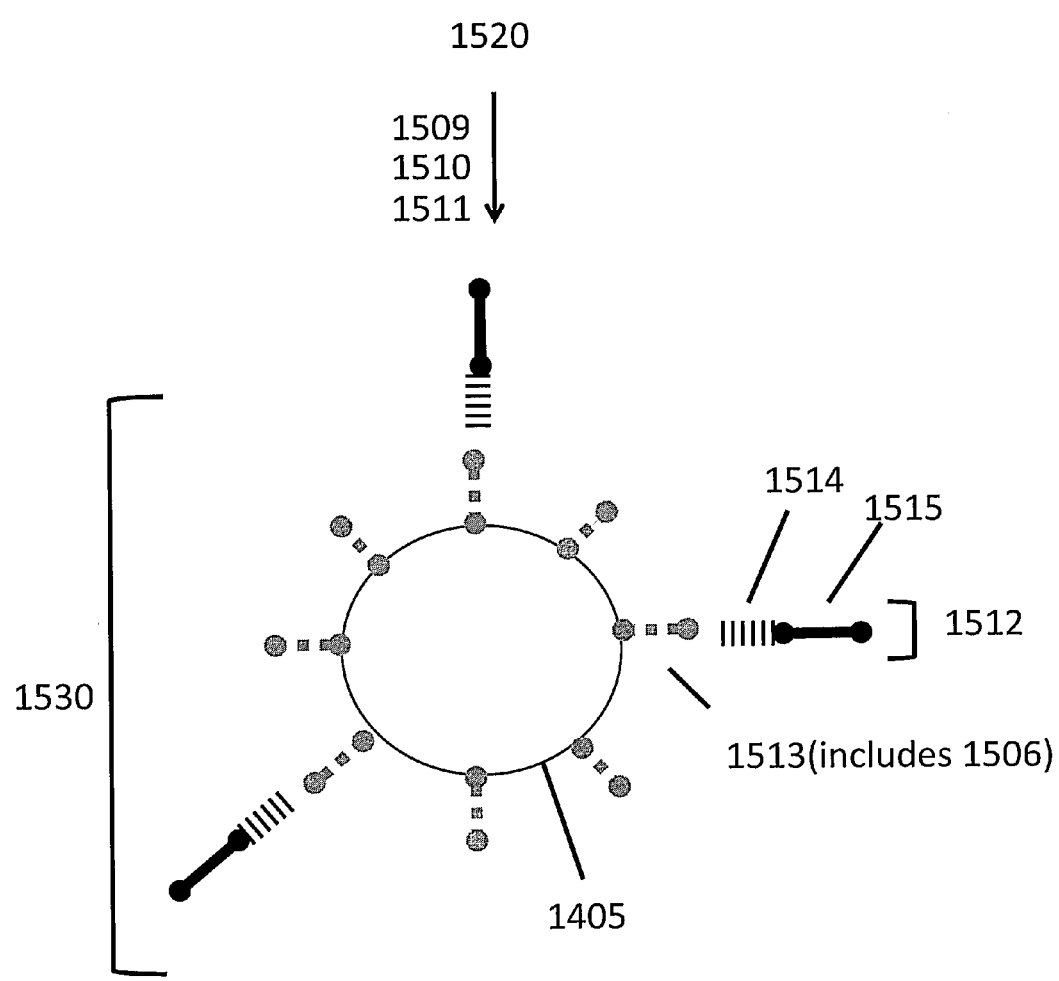

Fig. 19a

5'ACGACGCTCTTCCGATCT[Barcode][PrimingSeq]NNNNNNNN-3'
SEQ ID NO: 36

Fig. 19b

5'ACGACGCTCTTCCGATCT[Barcode][PrimingSeq] ⎞
3'TGCTGCGAGAAGGCTAGA[Barcode][PrimingSeq] ⎠

SEQ ID NO: 23

Fig. 19c

5'*GATCT*[Barcode][PrimingSeq] ⎞
3'       A[Barcode][PrimingSeq] ⎠

SEQ ID NO: 24

Fig. 19d

SEQ ID NO: 37
5'-ACACTCTTTCCCTACACGAC
                    GCTCTTCC
                    CGAGAAGGCTAG
3'-CACTGACCTCAAGTCTGCACA
SEQ ID NO: 25

Fig. 19e

5'-ACACTCTTTCCCTACACGAC
                    GCTCTTCC*GATCT*[Barcode][PrimingSeq] ⎞
                    CGAGAAGGCTAGA[Barcode][PrimingSeq] ⎠
3'-CACTGACCTCAAGTCTGCACA
SEQ ID NO: 26

SEQUENCE LISTING

```
<160> NUMBER OF SEQ ID NOS: 37

<210> SEQ ID NO 1
<211> LENGTH: 77
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
```

-continued

```
aatgatacgg cgaccaccga gatctacact agatcgcaca ctctttccct acacgacgct    60
cttccgatct gatctaa                                                   77

<210> SEQ ID NO 2
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
gatcggaaga gcacacgtct gaactccagt cacacactct ttccctacac gacgctcttc    60
cgatct                                                               66

<210> SEQ ID NO 3
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
acactctttc cctacacgac gctcttccga tct                                 33

<210> SEQ ID NO 4
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
gatcggaaga gcacacgtct gaactccagt cac                                 33

<210> SEQ ID NO 5
<211> LENGTH: 67
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (33)..(34)
<223> OTHER INFORMATION: The nucleotides at these positions are
      separated by an undisclosed barcoded target polynucleotide
      sequence

<400> SEQUENCE: 5
acactctttc cctacacgac gctcttccga tctagatcgg aagagcacac gtctgaactc    60
cagtcac                                                              67

<210> SEQ ID NO 6
<211> LENGTH: 67
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (33)..(34)
<223> OTHER INFORMATION: The nucleotides at these positions are
```

-continued separated by an undisclosed barcoded target polynucleotide
    sequence

<400> SEQUENCE: 6
acactctttc cctacacgac gctcttccga tctagatcgg aagagcacac gtctgaactc    60
cagtcac                                                               67

<210> SEQ ID NO 7
<211> LENGTH: 122
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (58)..(59)
<223> OTHER INFORMATION: The nucleotides at these positions are
      separated by an undisclosed barcoded target polynucleotide
      sequence

<400> SEQUENCE: 7
aatgatacgg cgaccaccga gatctacact ctttccctac acgacgctct tccgatctag    60
atcggaagag cacacgtctg aactccagtc acatcacgat ctcgtatgcc gtcttctgct   120
tg                                                                   122

<210> SEQ ID NO 8
<211> LENGTH: 122
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (64)..(65)
<223> OTHER INFORMATION: The nucleotides at these positions are
      separated by an undisclosed barcoded target polynucleotide
      sequence

<400> SEQUENCE: 8
caagcagaag acggcatacg agatcgtgat gtgactggag ttcagacgtg tgctcttccg    60
atctagatcg gaagagcgtc gtgtagggaa agagtgtaga tctcggtggt cgccgtatca   120
tt                                                                   122

<210> SEQ ID NO 9
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (34)..(41)
<223> OTHER INFORMATION: a, c, t or g

<400> SEQUENCE: 9
acactctttc cctacacgac gctcttccga tctnnnnnnnn nt                      42

<210> SEQ ID NO 10
<211> LENGTH: 42
<212> TYPE: DNA
<213> ORGANISM: Artificial Sequence
<220> FEATURE:
<223> OTHER INFORMATION: Description of Artificial Sequence: Synthetic -continued

```
      oligonucleotide
<220> FEATURE:
<221> NAME/KEY: modified_base
<222> LOCATION: (1)..(8)
<223> OTHER INFORMATION: a, c, t or g

<400> SEQUENCE: 10
nnnnnnnnag atcggaagag cacacgtctg aactccagtc ac                    42

<210> SEQ ID NO 11
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(8)
<223> OTHER INFORMATION: a, c, t or g
<220> FEATURE:
<221> NAME/KEY: modified_base
<222> LOCATION: (76)..(83)
<223> OTHER INFORMATION: a, c, t or g

<400> SEQUENCE: 11
nnnnnnnnag atcggaagag cacacgtctg aactccagtc acacactctt tccctacacg    60 acgtcttcc gatctnnnnn nnnt                                         84

<210> SEQ ID NO 12
<211> LENGTH: 88
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(12)
<223> OTHER INFORMATION: a, c, u or g
<220> FEATURE:
<221> NAME/KEY: modified_base
<222> LOCATION: (14)..(21)
<223> OTHER INFORMATION: a, c, t or g

<400> SEQUENCE: 12
nnnnnnnnnn nnannnnnnn nagatcggaa gagcgtcgtg tagggaaaga gtgtgtgact    60
ggagttcaga cgtgtgctct tccgatct                                    88

<210> SEQ ID NO 13
<211> LENGTH: 109
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(12)
<223> OTHER INFORMATION: a, c, u or g
<220> FEATURE:
<221> NAME/KEY: modified_base
<222> LOCATION: (14)..(21)
<223> OTHER INFORMATION: a, c, t or g
<220> FEATURE:
```

<221> NAME/KEY: modified_base
<222> LOCATION: (89)..(96)
<223> OTHER INFORMATION: a, c, t or g
<220> FEATURE:
<221> NAME/KEY: modified_base
<222> LOCATION: (98)..(109)
<223> OTHER INFORMATION: a, c, t or g

<400> SEQUENCE: 13
nnnnnnnnnn nnannnnnnn nagatcggaa gagcgtcgtg tagggaaaga gtgtgtgact    60
ggagttcaga cgtgtgctct tccgatctnn nnnnntnnn nnnnnnnn                 109

<210> SEQ ID NO 14
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(9)
<223> OTHER INFORMATION: a, c, t or g
<220> FEATURE:
<221> NAME/KEY: modified_base
<222> LOCATION: (77)..(84)
<223> OTHER INFORMATION: a, c, t or g
<220> FEATURE:
<221> NAME/KEY: modified_base
<222> LOCATION: (86)..(97)
<223> OTHER INFORMATION: a, c, t or g

<400> SEQUENCE: 14
annnnnnnna gatcggaaga gcgtcgtgta gggaaagagt gtgtgactgg agttcagacg    60
tgtgctcttc cgatctnnnn nnnntnnnnn nnnnnn                             97

<210> SEQ ID NO 15
<211> LENGTH: 96
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(9)
<223> OTHER INFORMATION: a, c, t or g
<220> FEATURE:
<221> NAME/KEY: modified_base
<222> LOCATION: (76)..(83)
<223> OTHER INFORMATION: a, c, t or g
<220> FEATURE:
<221> NAME/KEY: modified_base
<222> LOCATION: (85)..(96)
<223> OTHER INFORMATION: a, c, t or g

<400> SEQUENCE: 15
annnnnnnng atcggaagag cacacgtctg aactccagtc acacactctt tccctacacg    60
acgctcttcc gatctnnnnn nnntnnnnnn nnnnn                              96

<210> SEQ ID NO 16
<211> LENGTH: 96
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide -continued

```
<220> FEATURE:
<221> NAME/KEY: modified_base
<222> LOCATION: (1)..(13)
<223> OTHER INFORMATION: a, c, u or g
<220> FEATURE:
<221> NAME/KEY: modified_base
<222> LOCATION: (14)..(21)
<223> OTHER INFORMATION: a, c, t or g
<220> FEATURE:
<221> NAME/KEY: modified_base
<222> LOCATION: (88)..(95)
<223> OTHER INFORMATION: a, c, t or g

<400> SEQUENCE: 16
nnnnnnnnnn nnnnnnnnnn nagatcggaa gagcgtcgtg tagggaaaga gtgtgtgact    60
ggagttcaga cgtgtgctct tccgatcnnn nnnnt                              96

<210> SEQ ID NO 17
<211> LENGTH: 83
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(8)
<223> OTHER INFORMATION: a, c, t or g
<220> FEATURE:
<221> NAME/KEY: modified_base
<222> LOCATION: (75)..(82)
<223> OTHER INFORMATION: a, c, t or g

<400> SEQUENCE: 17
nnnnnnnnag atcggaagag cgtcgtgtag ggaaagagtg tgtgactgga gttcagacgt    60
gtgctcttcc gatcnnnnnn nnt                                           83

<210> SEQ ID NO 18
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (30)..(36)
<223> OTHER INFORMATION: a, c, t or g

<400> SEQUENCE: 18
aatgatacgg cgaccaccga gatctacacn nnnnnnacac tctttcccta cacgacgctc    60
ttccgatctt                                                          70

<210> SEQ ID NO 19
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (35)..(41)
<223> OTHER INFORMATION: a, c, t or g

<400> SEQUENCE: 19
aagatcggaa gagcgtcgtg tagggaaaga gtgtnnnnnn ngtgtagatc tcggtggtcg    60
ccgtatcatt                                                          70
```

<210> SEQ ID NO 20
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(27)
<223> OTHER INFORMATION: a, c, t or g

<400> SEQUENCE: 20
gtcgtgtagg gaaagagtgt nnnnnnngtg tagatctcgg tggtcgccgt atcatt            56

<210> SEQ ID NO 21
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
agatcggaag agcacacgtc tgaactccag tcac                                   34

<210> SEQ ID NO 22
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
ttagatcaga tcggaagagc acacgtctga actccagtca ctaaggcgaa tctcgtatgc       60
cgtcttctgc ttg                                                          73

<210> SEQ ID NO 23
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (18)..(19)
<223> OTHER INFORMATION: The nucleotides at these positions are
      separated by undisclosed barcode and primer sequencing regions

<400> SEQUENCE: 23
acgacgctct tccgatctag atcggaagag cgtcgt                                 36

<210> SEQ ID NO 24
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (5)..(6)
<223> OTHER INFORMATION: The nucleotides at these positions are
      separated by undisclosed barcode and primer sequencing regions

<400> SEQUENCE: 24 gatcta                                                              6

<210> SEQ ID NO 25
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
gatcggaaga gcacacgtct gaactccagt cac                                33

<210> SEQ ID NO 26
<211> LENGTH: 67
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (33)..(34)
<223> OTHER INFORMATION: The nucleotides at these positions are
      separated by undisclosed barcode and primer sequencing regions

<400> SEQUENCE: 26
acactctttc cctacacgac gctcttccga tctagatcgg aagagcacac gtctgaactc   60
cagtcac                                                             67

<210> SEQ ID NO 27
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(9)
<223> OTHER INFORMATION: a, c, t, g, unknown or other

<400> SEQUENCE: 27
ggccnnnnng gcc                                                      13

<210> SEQ ID NO 28
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(8)
<223> OTHER INFORMATION: a, c, t, g, unknown or other

<400> SEQUENCE: 28
caannnnngt gg                                                       12

<210> SEQ ID NO 29
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:

```
<221> NAME/KEY: modified_base
<222> LOCATION: (4)..(10)
<223> OTHER INFORMATION: a, c, t, g, unknown or other

<400> SEQUENCE: 29
gaannnnnnn ttgg                                              14

<210> SEQ ID NO 30
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(10)
<223> OTHER INFORMATION: a, c, t, g, unknown or other

<400> SEQUENCE: 30
gaacnnnnnn tcc                                               13

<210> SEQ ID NO 31
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(10)
<223> OTHER INFORMATION: a, c, t, g, unknown or other

<400> SEQUENCE: 31
gaagnnnnnn tac                                               13

<210> SEQ ID NO 32
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(9)
<223> OTHER INFORMATION: a, c, t, g, unknown or other

<400> SEQUENCE: 32
gaacnnnnnc tc                                                12

<210> SEQ ID NO 33
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(10)
<223> OTHER INFORMATION: a, c, t, g, unknown or other

<400> SEQUENCE: 33
gaacnnnnnn tac                                               13

<210> SEQ ID NO 34
<211> LENGTH: 5
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Gly Phe Leu Gly Lys
1               5

<210> SEQ ID NO 35
<211> LENGTH: 153
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (78)..(80)
<223> OTHER INFORMATION: a, c, t, g, unknown or other

<400> SEQUENCE: 35
aatgatacgg cgaccaccga gatctacact agatcgcaca ctctttccct acacgacgct    60
cttccgatct gatctaannn ttagatcaga tcggaagagc acacgtctga actccagtca   120
ctaaggcgaa tctcgtatgc cgtcttctgc ttg                                153

<210> SEQ ID NO 36
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (18)..(19)
<223> OTHER INFORMATION: The nucleotides at these positions are
      separated by undisclosed barcode and primer sequencing regions
<220> FEATURE:
<221> NAME/KEY: modified_base
<222> LOCATION: (19)..(26)
<223> OTHER INFORMATION: a, c, t or g

<400> SEQUENCE: 36
acgacgctct tccgatctnn nnnnnn                                         26

<210> SEQ ID NO 37
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
acactctttc cctacacgac gctcttcc                                       28
```

POLYNUCLEOTIDE BARCODE GENERATION

CROSS-REFERENCE

This application claims the benefit of U.S. Provisional Patent Application No. 61/762,435, filed Feb. 8, 2013, U.S. Provisional Patent Application No. 61/800,223, filed Mar. 15, 2013, U.S. Provisional Patent Application No. 61/840,403, filed Jun. 27, 2013, and U.S. Provisional Patent Application No. 61/844,804, filed Jul. 10, 2013, said applications are incorporated herein by reference in their entireties for all purposes.

The instant application contains a Sequence Listing which has been submitted electronically in ASCII format and is hereby incorporated by reference in its entirety. Said ASCII copy, created on Mar. 7, 2014, is named 43487706201SL.txt and is 14,795 bytes in size.

BACKGROUND

Polynucleotide barcodes have utility in numerous applications, including next generation sequencing techniques. Such barcodes generally contain unique identifier sequences, which can be extremely expensive to manufacture at sufficient diversity and scale. The cost of synthesizing a single polynucleotide barcode is a function of the cost per base during synthesis and the length of the polynucleotide. The cost of synthesizing a plurality of barcodes, each with a different sequence, is therefore equivalent to the cost per base, multiplied by the number of bases per molecule, multiplied by the number of molecules within the plurality of barcodes. Currently, it costs approximately $0.10 per base to synthesize a DNA sequence. For a barcode library of tens of thousands to millions of barcodes, this cost is prohibitive. Thus, there is a significant need for improved methods of generating libraries of barcodes.

SUMMARY

This disclosure provides methods, compositions, systems, and kits for the generation of polynucleotide barcodes and the use of such polynucleotide barcodes. Such polynucleotide barcodes may be used for any suitable application.

An aspect of the disclosure provides a library comprising one or more polynucleotides, each of the polynucleotides comprising a barcode sequence, wherein the polynucleotides are disposed within one or more partitions, and wherein the library comprises at least about 1,000 different barcode sequences.

In some cases, the barcode sequences are at least about 5 nucleotides in length. Also, the barcode sequences may be random polynucleotide sequences.

Moreover, the partitions may comprise, on average, about 1 polynucleotide, about 0.5 polynucleotides, or about 0.1 polynucleotides. The partitions may be droplets, capsules, wells or beads.

Furthermore, the library may comprise at least about 10,000 different barcode sequences, at least about 100,000 different barcode sequences, at least about 500,000 different barcode sequences, at least about 1,000,000 different barcode sequences, at least about 2,500,00 different barcode sequences, at least about 5,000,000 different barcode sequences, at least about 10,000,000, at least about 25,000,000, at least about 50,000,000, or at least about 100,000,000 different barcode sequences.

In some cases, the partitions may comprise multiple copies of the same polynucleotide.

Additionally, each of the polynucleotides may comprise a sequence selected from the group consisting of an immobilization sequence, an annealing sequence for a sequencing primer, and a sequence compatible for ligation with a target polynucleotide.

In some cases, each of the polynucleotides is a MALBAC primer.

Another aspect of the disclosure provides a method of synthesizing a library of polynucleotides comprising barcode sequences, the method comprising: a.) synthesizing a plurality of polynucleotides comprising barcode sequences; b.) separating the polynucleotides into a plurality of partitions, thereby generating partitioned polynucleotides; c.) amplifying the partitioned polynucleotides, thereby generating amplified polynucleotides; and d.) isolating partitions comprising amplified polynucleotides. In some cases, the synthesizing comprises including a mixture of adenine, thymine, guanine, and cytosine in a coupling reaction.

Moreover, the separating may comprise performing a limiting dilution, thereby generating diluted polynucleotides. In some cases, the separating further comprises partitioning said diluted polynucleotides.

Additionally, the amplifying may be performed by a method selected from the group consisting of polymerase chain reaction, asymmetric polymerase chain reaction, emulsion PCR (ePCR), ePCR including the use of a bead, ePCR including the use of a hydrogel, multiple annealing and looping-based amplification cycles (MALBAC), single primer isothermal amplification, and combinations thereof. In some cases, the amplifying is performed using an RNA primer and may include exposing the amplified polynucleotides to an RNAase H.

In some cases, each of said polynucleotides comprising barcode sequences is a MALBAC primer.

In some cases, the isolating may be performed by flow-assisted sorting.

Also, a hairpin structure may be formed from a polynucleotide selected from the group consisting of the polynucleotides comprising barcode sequences and the amplified polynucleotides. In some cases, a method may further comprise cutting the hairpin structure within an unannealed region.

Moreover, a polynucleotide selected from the group consisting of said polynucleotides comprising barcode sequences, said partitioned polynucleotides, and said amplified polynucleotides may be attached to a bead.

The method may further comprise annealing the amplified polynucleotides with a partially complementary sequence. The partially complementary sequence may comprise a barcode sequence.

The method may further comprise attaching at least one of the amplified polynucleotides to a target sequence. The target sequence may be fragmented. In some cases, the target sequence is fragmented by a method selected from the group consisting of mechanical shear and treatment with an enzyme. The mechanical shear may be induced by ultrasound. In some cases, the enzyme is selected from the group consisting of a restriction enzyme, a fragmentase, and a transposase. Additionally, the attaching may be performed by a method selected from the group consisting of ligation and amplification.

In some cases, the amplification is a MALBAC amplification performed with MALBAC primers, thereby generating a MALBAC amplification product. In some cases, the MALBAC primers comprise the amplified polynucleotides. In some cases, the MALBAC primers comprise polynucleotides that are not said amplified polynucleotides. In such cases, the method may further comprise attaching the MALBAC amplification product to the amplified polynucleotide.

Additionally, each of the partitions may comprise, on average, about 1 polynucleotide comprising a barcode sequence, 0.5 polynucleotides comprising barcode sequences, or 0.1 polynucleotides comprising barcode sequences. Moreover, the partitions may be selected from the group consisting of droplets, capsules, and wells.

In some cases, the library comprises at least about 1,000 different barcode sequences, at least about 10,000 different barcode sequences, at least about 100,000 different barcode sequences, at least about 500,000 different barcode sequences, at least about 1,000,000 different barcode sequences, at least about 2,500,00 different barcode sequences, at least about 5,000,000 different barcode sequences, at least about 10,000,000, at least about 25,000,000, at least about 50,000,000, or at least about 100,000,000 different barcode sequences.

In some cases, the partitions comprise multiple copies of the same polynucleotide comprising a barcode sequence.

Moreover, the polynucleotides comprising barcode sequences may comprise a sequence selected from the group consisting of an immobilization sequence, an annealing sequence for a sequencing primer, and a sequence compatible for ligation with a target polynucleotide.

An additional aspect of the disclosure provides a library comprising at least about 1,000 beads, wherein each bead of the at least about 1,000 beads comprises a different barcode sequence. In some cases, the different barcode sequence can be included in a polynucleotide comprising an immobilization sequence and/or an annealing sequence for a sequencing primer. In some cases, the different barcode sequence can be at least about 5 nucleotides or at least about 10 nucleotides in length. In some cases, the different barcode sequence can be a random polynucleotide sequence or can be generated combinatorially.

Moreover, each of the 1,000 beads can comprise multiple copies of the different barcode sequence. For example, each of the 1,000 beads may comprise at least about 100,000, at least about 1,000,000, or at least about 10,000,000 copies of the different barcode sequence. In some cases, the library can further comprise two or more beads comprising the same barcode sequence. In some cases, at least two beads of the 1,000 beads can comprise the same barcode sequence. Furthermore, the at least about 1,000 beads may comprise at least about 10,000 beads, or at least about 100,000 beads.

Also, the library can comprise at least about 1,000, at least about 10,000, at least about 100,000, at least about 1,000,000, at least about 2,500,000, at least about 5,000,000, at least about 10,000,000, at least about 25,000,000, at least about 50,000,000, or at least about 100,000,000 different barcode sequences.

In some cases, the at least about 1,000 beads can be distributed across a plurality of partitions. In some cases, the partitions can be droplets of an emulsion. In some cases, each bead of the 1,000 beads can be included in a different partition. In some cases, the different partition can be a droplet of an emulsion. In some cases, two or more beads of the 1,000 beads can be included in a different partition. In some cases, the different partition can be a droplet of an emulsion. In some cases, the 1,000 beads can be hydrogel beads.

An additional aspect of the disclosure provides for use of a library, composition, method, device, or kit described herein in partitioning species, in partitioning oligonucleotides, in stimulus-selective release of species from partitions, in performing reactions (e.g., ligation and amplification reactions) in partitions, in performing nucleic acid synthesis reactions, in barcoding nucleic acid, in preparing polynucleotides for sequencing, in sequencing polynucleotides, in mutation detection, in neurologic disorder diagnostics, in diabetes diagnostics, in fetal aneuploidy diagnostics, in cancer mutation detection and forenscics, in disease detection, in medical diagnostics, in low input nucleic acid applications, in circulating tumor cell (CTC) sequencing, in polynucleotide phasing, in sequencing polynucleotides from small numbers of cells, in analyzing gene expression, in partitioning polynucleotides from cells, or in a combination thereof.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of methods, compositions, systems, and devices of this disclosure are set forth with particularity in the appended claims. A better understanding of the features and advantages of this disclosure will be obtained by reference to the following detailed description that sets forth illustrative embodiments, in which the principles of the methods, compositions, systems, and devices of this disclosure are utilized, and the accompanying drawings of which:

FIG. 3 depicts example sequences of two forked adapters ligated to opposite ends of a target polynucleotide. Full-length sequence disclosed as SEQ ID NO: 35.

FIGS. 8a-c depict example sequences described in Example 4.

FIGS. 9a-j depict example sequences described in Example 5.

FIGS. 10a-e depict example sequences described in Example 6.

FIGS. 15a-e schematically depict methods and structures described in Example 9.

FIGS. 19a-e depict example sequences described in Example 13.

DETAILED DESCRIPTION

Figure 1:
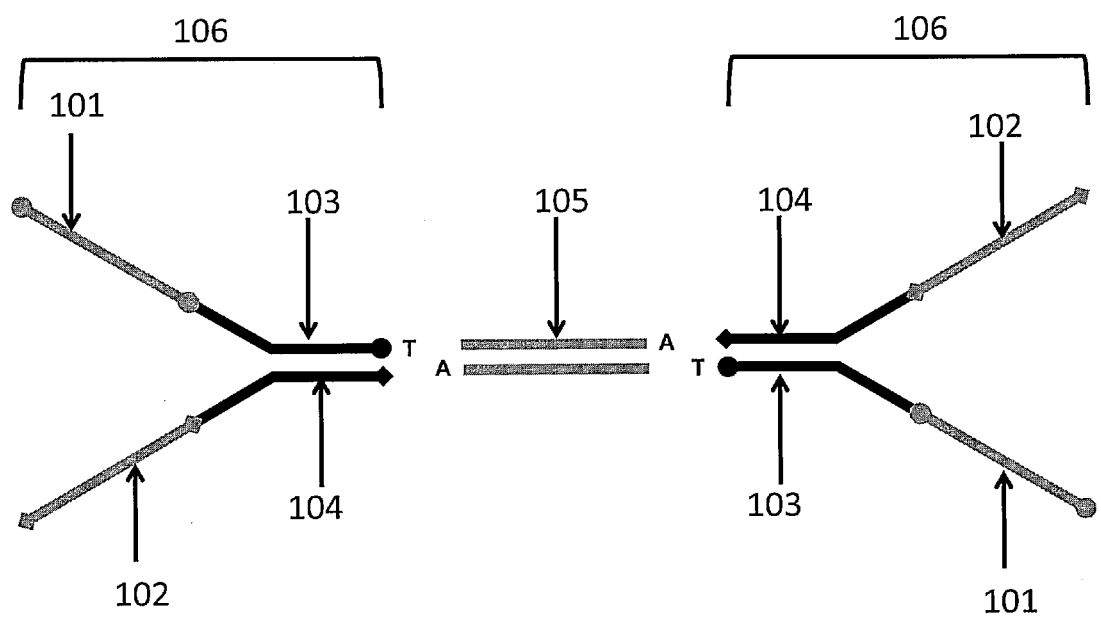
FIG. 1 is schematically depicts an example forked adapter.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

This disclosure provides methods, compositions, systems, and kits for the generation of polynucleotide barcodes and the use of such polynucleotide barcodes. Such polynucleotide barcodes may be used for any suitable application. In some cases, the polynucleotide barcodes provided in this disclosure may be used in next generation sequencing reactions. Next generation sequencing reactions include the sequencing of whole genomes, detection of specific sequences such as single nucleotide polymorphisms (SNPs) and other mutations, detection of nucleic acid (e.g., deoxyribonucleic acid) insertions, and detection of nucleic acid deletions.

Utilization of the methods, compositions, systems, and kits described herein may incorporate, unless otherwise indicated, any conventional techniques of organic chemistry, polymer technology, microfluidics, molecular biology, recombinant techniques, cell biology, biochemistry, and immunology. Such conventional techniques include well and microwell construction, capsule generation, generation of emulsions, spotting, microfluidic device construction, polymer chemistry, restriction digestion, ligation, cloning, polynucleotide sequencing, and polynucleotide sequence assembly. Specific, non-limiting, illustrations of suitable techniques are described throughout this disclosure. However, equivalent procedures may also be utilized. Descriptions of certain techniques may be found in standard laboratory manuals, such as *Genome Analysis: A Laboratory Manual Series* (Vols. I-IV), *Using Antibodies: A Laboratory Manual*, *Cells: A Laboratory Manual*, *PCR Primer: A Laboratory Manual*, and *Molecular Cloning: A Laboratory Manual* (all from Cold Spring Harbor Laboratory Press), and "Oligonucleotide Synthesis: A Practical Approach" 1984, IRL Press London, all of which are herein incorporated in their entirety by reference for all purposes.

I. DEFINITIONS

The terminology used herein is for the purpose of describing particular embodiments only and is not intended to be limiting.

As used herein, the singular forms "a," "an," and "the" are intended to include the plural forms as well, unless the context clearly indicates otherwise. Furthermore, to the extent that the terms "including," "includes," "having," "has," "with," "such as," or variants thereof, are used in either the specification and/or the claims, such terms are not limiting and are intended to be inclusive in a manner similar to the term "comprising".

The term "about," as used herein, generally refers to a range that is 15% greater than or less than a stated numerical value within the context of the particular usage. For example, "about 10" would include a range from 8.5 to 11.5.

The term "barcode," as used herein, generally refers to a label that may be attached to an analyte to convey information about the analyte. For example, a barcode may be a polynucleotide sequence attached to fragments of a target polynucleotide contained within a particular partition. This barcode may then be sequenced with the fragments of the target polynucleotide. The presence of the same barcode on multiple sequences may provide information about the origin of the sequence. For example, a barcode may indicate that the sequence came from a particular partition and/or a proximal region of a genome. This may be particularly useful for sequence assembly when several partitions are pooled before sequencing.

The term "bp," as used herein, generally refers to an abbreviation for "base pairs".

The term "microwell," as used herein, generally refers to a well with a volume of less than 1 mL. Microwells may be made in various volumes, depending on the application. For example, microwells may be made in a size appropriate to accommodate any of the partition volumes described herein.

The term "partition," as used herein, may be a verb or a noun. When used as a verb (e.g., "to partition," or "partitioning"), the term generally refers to the fractionation (e.g., subdivision) of a species or sample (e.g., a polynucleotide) between vessels that can be used to sequester one fraction (or subdivision) from another. Such vessels are referred to using the noun "partition." Partitioning may be performed, for example, using microfluidics, dilution, dispensing, and the like. A partition may be, for example, a well, a microwell, a hole, a droplet (e.g., a droplet in an emulsion), a continuous phase of an emulsion, a test tube, a spot, a capsule, a bead, a surface of a bead in dilute solution, or any other suitable container for sequestering one fraction of a sample from another. A partition may also comprise another partition.

The terms "polynucleotide" or "nucleic acid," as used herein, generally refer to molecules comprising a plurality of nucleotides. Exemplary polynucleotides include deoxyribonucleic acids, ribonucleic acids, and synthetic analogues thereof, including peptide nucleic acids.

The term "species," as used herein, generally refers to any substance that can be used with the methods, compositions, systems, devices, and kits of this disclosure. Examples of species include reagents, analytes, cells, chromosomes, tagging molecules or groups of molecules, barcodes, and any sample comprising any of these species. Any suitable species may be used, as more fully discussed elsewhere in this disclosure.

II. POLYNUCLEOTIDE BARCODING

Certain applications, for example polynucleotide sequencing, may rely on unique identifiers ("barcodes") to identify the origin of a sequence and, for example, to assemble a larger sequence from sequenced fragments. Therefore, it may be desirable to add barcodes to polynucleotide fragments before sequencing. Barcodes may be of a variety of different formats, including polynucleotide barcodes. Depending upon the specific application, barcodes may be attached to polynucleotide fragments in a reversible or irreversible manner.

Additionally, barcodes may allow for identification and/or quantification of individual polynucleotide fragments during sequencing.

Barcodes may be loaded into partitions so that one or more barcodes are introduced into a particular partition. In some cases, each partition may contain a different set of barcodes. This may be accomplished by directly dispensing the barcodes into the partitions, or by placing the barcodes within a partition that is contained within another partition.

The barcodes may be loaded into the partitions at an expected or predicted ratio of barcodes per species to be barcoded (e.g., polynucleotide fragment, strand of polynucleotide, cell, etc.). In some cases, the barcodes are loaded into partitions such that about 0.0001, 0.001, 0.1, 1, 2, 3, 4, 5, 6, 7, 8, 9, 10, 20, 50, 100, 500, 1000, 5000, 10000, or 200000 barcodes are loaded per species. In some cases, the barcodes are loaded into partitions such that more than about 0.0001, 0.001, 0.1, 1, 2, 3, 4, 5, 6, 7, 8, 9, 10, 20, 50, 100, 500, 1000, 5000, 10000, or 200000 barcodes are loaded per species. In some cases, the barcodes are loaded in the partitions so that less than about 0.0001, 0.001, 0.1, 1, 2, 3, 4, 5, 6, 7, 8, 9, 10, 20, 50, 100, 500, 1000, 5000, 10000, or 200000 barcodes are loaded per species.

When more than one barcode is present per polynucleotide fragment, such barcodes may be copies of the same barcode, or may be different barcodes. For example, the attachment process may be designed to attach multiple identical barcodes to a single polynucleotide fragment, or multiple different barcodes to the polynucleotide fragment.

The methods provided herein may comprise loading a partition with the reagents necessary for the attachment of barcodes to polynucleotide fragments. In the case of ligation reactions, reagents including restriction enzymes, ligase enzymes, buffers, adapters, barcodes and the like may be loaded into a partition. In the case of barcoding by amplification, reagents including primers, DNA polymerases, dNTPs, buffers, barcodes and the like may be loaded into a partition. In the case of transposon-mediated barcoding (e.g., NEXTERA), reagents including a transposome (i.e., transposase and transposon end complex), buffers, and the like may be loaded into a partition. In the case of MALBAC-mediated barcoding, reagents including a MALBAC primer, buffers, and the like may be loaded into a partition. As described throughout this disclosure, these reagents may be loaded directly into the partition, or via another partition.

Barcodes may be ligated to a polynucleotide fragment using sticky or blunt ends. Barcoded polynucleotide fragments may also be generated by amplifying a polynucleotide fragment with primers comprising barcodes. In some cases, MALBAC amplification of the polynucleotide fragment may be used to generate a barcoded polynucleotide fragment. A primer used for MALBAC may or may not comprise a barcode. In cases where a MALBAC primer does not comprise a barcode, the barcode may be added to MALBAC amplification products by other amplification methods, such as, for example, PCR. Barcoded polynucleotide fragments may also be generated using transposon-mediated methods. As with any other species discussed in this disclosure, these modules may be contained within the same or different partitions, depending on the needs of the assay or process.

In some cases, barcodes may be assembled combinatorially, from smaller components designed to assemble in a modular format. For example, three modules, 1A, 1B, and 1C may be combinatorially assembled to produce barcode 1ABC. Such combinatorial assembly may significantly reduce the cost of synthesizing a plurality of barcodes. For example, a combinatorial system consisting of 3 A modules, 3 B modules, and 3 C modules may generate 3*3*3=27 possible barcode sequences from only 9 modules.

In some cases, as further described elsewhere in this disclosure, barcodes may be combinatorially assembled by mixing two oligonucleotides and hybridizing them to produce annealed or partially annealed oligonucleotides (e.g., forked adapters). These barcodes may comprise an overhang of one or more nucleotides, in order to facilitate ligation with polynucleotide fragments that are to be barcoded. In some cases, the 5' end of the antisense strand may be phosphorylated in order to ensure double-stranded ligation. Using this approach, different modules may be assembled by, for example, mixing oligonucleotides A and B, A and C, A and D, B and C, B, and D, and so on. As described in more detail elsewhere in this disclosure, the annealed oligonucleotides may also be synthesized as a single molecule with a hairpin loop that may be cut after ligation to the polynucleotide to be barcoded.

As described in more detail elsewhere in this disclosure, attachment of polynucleotides to each other may rely on hybridization-compatible overhangs. For example, the hybridization between A and T is often used to ensure ligation compatibility between fragments. In some cases, an A overhang may be created by treatment with an enzyme, such as a Taq polymerase. In some cases, a restriction enzyme may be used to create a cleavage product with a single base 3' overhang which may be, for example, A or T. Examples of restriction enzymes that leave a single base 3' overhang include MnlI, HphI, Hpy188I, HpyAV, HpyCH4III, MboII, BciVI, BmrI, AhdI, and XcmI. In other cases, different overhangs (e.g., 5' overhangs, overhangs of greater than a single base) may be generated by restriction enzymes. Additional restriction enzymes that may be used to generate overhangs include BfuC1, Taq$^\alpha$I, BbVI, Bcc1, BceA1, BcoDI, BsmAI, and BsmFI.

III. GENERATION OF PARTITIONED BARCODE LIBRARIES

In some cases, this disclosure provides methods for the generation of partitioned barcode libraries and libraries produced according to such methods. In some cases, the methods provided herein combine random synthesis of DNA sequences, separation into partitions, amplification of separated sequences, and isolation of amplified separated sequences to provide a library of barcodes contained within partitions.

a. Random Synthesis of Polynucleotide Barcodes

In some cases, the methods described herein utilize random methods of polynucleotide synthesis, including random methods of DNA synthesis. During random DNA synthesis, any combination of A, C, G, and/or T may be added to a coupling step so that each type of base in the coupling step is coupled to a subset of the product. If A, C, G, and T are present at equivalent concentrations, approximately one-quarter of the product will incorporate each base. Successive coupling steps, and the random nature of the coupling reaction, enable the generation of $4^n$ possible sequences, where n is the number of bases in the polynucleotide. For example, a library of random polynucleotides of length 6 could have a diversity of $4^6=4,096$ members, while a library of length 10 would have diversity of 1,048,576 members. Therefore, very large and complex libraries can be generated. These random sequences may serve as barcodes.

Any suitable synthetic bases may also be used with the invention. In some cases, the bases included in each coupling step may be altered in order to synthesize a preferred product.

For example, the number of bases present in each coupling step may be 1, 2, 3, 4, 5, 6, 7, 8, 9, 10, or more. In some cases, the number of bases present in each coupling step may be at least 1, 2, 3, 4, 5, 6, 7, 8, 9, 10, or more. In some cases, the number of bases present in each coupling step may be less than 2, 3, 4, 5, 6, 7, 8, 9, or 10.

The concentration of the individual bases may also be altered in order to synthesize the preferred product. For example, any base may be present at a concentration of about 0.1, 0.5, 1, 5, or 10-fold the concentration of another base. In some cases, any base may be present at a concentration of at least about 0.1, 0.5, 1, 5, or 10-fold the concentration of another base. In some cases, any base may be present at a concentration of less than about 0.1, 0.5, 1, 5, or 10-fold the concentration of another base.

The length of the random polynucleotide sequence may be any suitable length, depending on the application. In some cases, the length of the random polynucleotide sequence may be 4, 5, 6, 7, 8, 9, 10, 11, 12, 13, 14, 15, 16, 17, 18, 19, 20, or more nucleotides. In some cases, the length of the random polynucleotide sequence may be at least 4, 5, 6, 7, 8, 9, 10, 11, 12, 13, 14, 15, 16, 17, 18, 19, 20, or more nucleotides. In some cases, the length of the random polynucleotide sequence may be less than 4, 5, 6, 7, 8, 9, 10, 11, 12, 13, 14, 15, 16, 17, 18, 19, or 20 nucleotides.

In some cases, the library is defined by the number of members. In some cases, a library may comprise about 256, 1024, 4096, 16384, 65536, 262144, 1048576, 4194304, 16777216, 67108864, 268435456, 1073741824, 4294967296, 17179869184, 68719476736, $2.74878*10^{11}$, or $1.09951*10^{12}$ members. In some cases, a library may comprise at least about 256, 1024, 4096, 16384, 65536, 262144, 1048576, 4194304, 16777216, 67108864, 268435456, 1073741824, 4294967296, 17179869184, 68719476736, $2.74878*10$, or $1.09951*10^{12}$ members. In some cases, a library may comprise less than about 256, 1024, 4096, 16384, 65536, 262144, 1048576, 4194304, 16777216, 67108864, 268435456, 1073741824, 4294967296, 17179869184, 68719476736, $2.74878*10$, or $1.09951*10^{12}$ members. In some cases, the library is a barcode library. In some cases, a barcode library may comprise at least about 1000, 10000, 100000, 1000000, 2500000, 5000000, 10000000, 25000000, 50000000, or 100000000 different barcode sequences.

The random barcode libraries may also comprise other polynucleotide sequences. In some cases, these other polynucleotide sequences are non-random in nature and include, for example, primer binding sites, annealing sites for the generation of forked adapters, immobilization sequences, and regions that enable annealing with a target polynucleotide sequence, and thus barcoding of the polynucleotide sequence.

b. Separation of Polynucleotides into Partitions

After synthesis of polynucleotides comprising random barcode sequences, the polynucleotides are partitioned into separate compartments to generate a library of partitioned polynucleotides comprising barcode sequences. Any suitable method of separation and any suitable partition or partitions within partitions may be used.

In some cases, partitioning is performed by diluting the mixture of polynucleotides comprising random barcode sequences such that a particular volume of the dilution contains, on average, less than a single polynucleotide. The particular volume of the dilution may then be transferred to a partition. In any plurality of partitions, each partition is therefore likely to have one or zero polynucleotide molecules.

In some cases a dilution may be performed such that each partition comprises about 0.001, 0.01, 0.1, 0.2, 0.3, 0.4, 0.5, 0.6, 0.7, 0.8, 0.9, 1, 2, or more molecules. In some cases a dilution may be performed such that each partition comprises at least about 0.001, 0.01, 0.1, 0.2, 0.3, 0.4, 0.5, 0.6, 0.7, 0.8, 0.9, 1, 2, or more molecules. In some cases a dilution may be performed such that each partition comprises less than about 0.001, 0.01, 0.1, 0.2, 0.3, 0.4, 0.5, 0.6, 0.7, 0.8, 0.9, 1, or 2 molecules.

In some cases, about 10%, 20%, 30%, 40%, 50%, 60%, 70%, 80%, or 90% of the partitions comprise the specified number of molecules. In some cases, at least about 10%, 20%, 30%, 40%, 50%, 60%, 70%, 80%, or 90% of the partitions comprise the specified number of molecules. In some cases, less than about 10%, 20%, 30%, 40%, 50%, 60%, 70%, 80%, or 90% of the partitions comprise the specified number of molecules.

In some cases, about 10%, 20%, 30%, 40%, 50%, 60%, 70%, 80%, or 90% of the partitions comprise one or fewer polynucleotides. In some cases, at least about 10%, 20%, 30%, 40%, 50%, 60%, 70%, 80%, or 90% of the partitions comprise one or fewer polynucleotides. In some cases, less than about 10%, 20%, 30%, 40%, 50%, 60%, 70%, 80%, or 90% of the partitions comprise one or fewer polynucleotides.

In some cases, a partition is a well, a microwell, a hole, a droplet (e.g., a droplet in an emulsion), a continuous phase of an emulsion, a test tube, a spot, a capsule, a surface of a bead, or any other suitable container for sequestering one fraction of a sample from another. In cases where a partition includes a bead, a primer for amplification may be attached to the bead. Partitions are described in greater detail elsewhere in this disclosure.

c. Amplification of Partitioned Polynucleotides

The polynucleotides partitioned as described above are then amplified in order to generate sufficient material for barcoding of a target polynucleotide sequence. Any suitable method of amplification may be utilized, including polymerase chain reaction (PCR), ligase chain reaction (LCR), helicase-dependent amplification, linear after the exponential PCR (LATE-PCR), asymmetric amplification, digital PCR, degenerate oligonucleotide primer PCR (DOP-PCR), primer extension pre-amplification PCR (PEP-PCR), ligation mediated PCR, rolling circle amplification, multiple displacement amplification (MDA), and single primer isothermal amplification (SPIA), emulsion PCR (ePCR), ePCR including the use of a bead, ePCR including the use of a hydrogel, multiple annealing and looping-based amplification cycles (MALBAC), and combinations thereof. MALBAC methods are described, for example, in Zong et al., *Science,* 338(6114), 1622-1626 (2012), which is incorporated herein by reference, in its entirety.

In some cases, amplification methods that generate single-stranded product (e.g., asymmetric amplification, SPIA, and LATE-PCR) may be preferred, for example. In some cases, amplification methods that generate double-stranded products (e.g., standard PCR) may be preferred. In some cases, an amplification method will exponentially amplify the partitioned polynucleotide. In some cases, an amplification method will linearly amplify the partitioned polynucleotide. In some cases, an amplification method will first exponentially and then linearly amplify a polynucleotide. Moreover, a single type of amplification may be used to amplify polynucleotides or amplification may be completed with sequential steps of different types of amplification. For example, ePCR may be combined with further rounds of ePCR or may be combined with a different type of amplification.

Amplification is performed until a suitable amount of polynucleotide comprising a barcode is produced. In some cases, amplification may be performed for 10, 15, 20, 25, 30, 35, 40, 45, 50, 55, 60, or more cycles. In some cases, amplification may be performed for at least 10, 15, 20, 25, 30, 35, 40, 45, 50, 55, 60, or more cycles. In some cases, amplification may be performed for less than 10, 15, 20, 25, 30, 35, 40, 45, 50, 55, or 60 cycles.

In some cases, amplification may be performed until a certain amount of polynucleotide product is produced in each partition. In some cases, amplification is performed until the amount of polynucleotide product is about 10,000,000,000; 5,000,000,000; 1,000,000,000; 500,000,000; 100,000,000; 50,000,000; 10,000,000; 5,000,000; 1,000,000; 500,000; 400,000; 300,000; 200,000; or 100,000 molecules. In some cases, amplification is performed until the amount of polynucleotide product is at least about 100,000; 200,000; 300,000; 400,000; 500,000; 1,000,000; 5,000,000; 10,000,000; 50,000,000; 100,000,000; 500,000,000; 1,000,000,000; 5,000,000,000; or 10,000,000,000 molecules. In some cases, amplification is performed until the amount of polynucleotide product is less than about 10,000,000,000; 5,000,000,000; 1,000,000,000; 500,000,000; 100,000,000; 50,000,000; 10,000,000; 5,000,000; 1,000,000; 500,000; 400,000; 300,000; 200,000; or 100,000 molecules.

d. Isolation of Partitions Comprising Amplified Sequences

As described above, in some cases polynucleotides comprising barcodes are partitioned such that each partition contains, on average, less than one polynucleotide sequence. Therefore, in some cases, a fraction of the partitions will not contain a polynucleotide and therefore cannot contain an amplified polynucleotide. Thus, it may be desirable to separate partitions comprising polynucleotides from partitions not comprising polynucleotides.

In one case, partitions comprising polynucleotides are separated from partitions not comprising polynucleotides using flow-based sorting methods capable of identifying partitions comprising polynucleotides. In some cases an indicator of the presence of a polynucleotide may be used in order to differentiate partitions comprising polynucleotides from those not comprising polynucleotides.

In some cases, a nucleic acid stain may be used to identify partition comprising polynucleotides. Exemplary stains include intercalating dyes, minor-groove binders, major groove binders, external binders, and bis-intercalators. Specific examples of such dyes include SYBR green, SYBR blue, DAPI, propidium iodide, SYBR gold, ethidium bromide, acridines, proflavine, acridine orange, acriflavine, fluorcoumanin, ellipticine, daunomycin, chloroquine, distamycin D, chromomycin, homidium, mithramycin, ruthenium polypyridyls, anthramycin, phenanthridines and acridines, ethidium bromide, propidium iodide, hexidium iodide, dihydroethidium, ethidium homodimer-1 and -2, ethidium monoazide, ACMA, indoles, imidazoles (e.g., Hoechst 33258, Hoechst 33342, Hoechst 34580 and DAPI), acridine orange (also capable of intercalating), 7-AAD, actinomycin D, LDS751, hydroxystilbamidine, SYTOX Blue, SYTOX Green, SYTOX Orange, POPO-1, POPO-3, YOYO-1, YOYO-3, TOTO-1, TOTO-3, JOJO-1, LOLO-1, BOBO-1, BOBO-3, PO-PRO-1, PO-PRO-3, BO-PRO-1, BO-PRO-3, TO-PRO-1, TO-PRO-3, TO-PRO-5, JO-PRO-1, LO-PRO-1, YO-PRO-1, YO-PRO-3, PicoGreen, OliGreen, RiboGreen, SYBR Gold, SYBR Green I, SYBR Green II, SYBR DX, SYTO-40, -41, -42, -43, -44, -45 (blue), SYTO-13, -16, -24, -21, -23, -12, -11, -20, -22, -15, -14, -25 (green), SYTO-81, -80, -82, -83, -84, -85 (orange), SYTO-64, -17, -59, -61, -62, -60, and -63 (red).

In some cases, isolation methods such as magnetic separation or sedimentation of particles may be used. Such methods may include, for example, a step of attaching a polynucleotide to be amplified, a primer corresponding to said polynucleotide to be amplified, and/or a polynucleotide product of amplification to a bead. In some cases, attachment of a polynucleotide to be amplified, primer corresponding to said polynucleotide to be amplified, and/or a polynucleotide product to a bead may be via a photolabile linker, such as, for example, PC Amino C6. In cases where a photolabile linker is used, light may be used to release a linked polynucleotide from the bead. The bead may be, for example, a magnetic bead or a latex bead. The bead may then enable separation by, for example, magnetic sorting or sedimentation. Sedimentation of latex particles may be performed, for example, by centrifugation in a liquid that is more dense than latex, such as glycerol. In some cases, density gradient centrifugation may be used.

Beads may be of uniform size or heterogeneous size. In some cases, the diameter of a bead may be about 0.001 µm, 0.01 µm, 0.05 µm, 0.1 µm, 0.5 µm, 1 µm, 5 µm, 10 µm, 50 µm, 100 µm, 150 µm, 200 µm, 300 µm, 400 µm, 500 µm, 600 µm, 700 µm, 800 µm, 900 µm, or 1 mm. A bead may have a diameter of at least about 0.001 µm, 0.01 µm, 0.05 µm, 0.1 µm, 0.5 µm, 1 µm, 5 µm, 10 µm, 50 µm, 100 µm, 150 µm, 200 µm, 300 µm, 400 µm, 500 µm, 600 µm, 700 µm, 800 µm, 900 µm, or 1 mm. In some cases, a bead may have a diameter of less than about 0.001 µm, 0.01 µm, 0.05 µm, 0.1 µm, 0.5 µm, 1 µm, 5 µm, 10 µm, 50 µm, 100 µm, 150 µm, 200 µm, 300 µm, 400 µm, 500 µm, 600 µm, 700 µm, 800 µm, 900 µm, or 1 mm. In some cases, a bead may have a diameter of about 0.001 µm to 1 mm, 0.01 µm to 900 µm, 0.1 µm to 600 µm, 100 µm to 200 µm, 100 µm to 300 µm, 100 µm to 400 µm, 100 µm to 500 µm, 100 µm to 600 µm, 20 µm to 50 µm, 150 µm to 200 µm, 150 µm to 300 µm, or 150 µm to 400 µm.

In some cases, a differential charge between the partitions comprising polynucleotides and partitions not comprising polynucleotides may be used to isolate partitions comprising polynucleotides, for example by performing electrophoresis or dielectrophoresis on the partitions.

In some cases, selective swelling or shrinking of partitions, based on differences in the osmotic pressures, may be used to identify particles comprising polynucleotides. In some instances, partitions comprising polynucleotides may be isolated by flow fractionation, solvent extraction, differential melting (e.g., with nucleic acid probes), or freezing.

Isolation of partitions comprising polynucleotides provides a library of partitioned polynucleotide barcodes with significant diversity while incurring only a one-time bulk synthesis expense.

IV. GENERATION OF ADAPTERS COMPRISING BARCODES

The barcodes described in this disclosure can have a variety of structures. In some cases, barcodes of this disclosure are a part of an adapter. Generally, an "adapter" is a structure used to enable attachment of a barcode to a target polynucleotide. An adapter may comprise, for example, a barcode, polynucleotide sequence compatible for ligation with a target polynucleotide, and functional sequences such as primer binding sites and immobilization regions.

In some cases, an adapter is a forked adapter. An example of a forked adapter is schematically depicted in FIG. 1. With reference to FIG. 1, two copies of a forked adapter structure 106 are depicted on opposite sides of a target polynucleotide 105. Each forked adapter comprises a first immobilization region 101, a second immobilization region 102, a first sequencing primer region 103, a second sequencing primer region 104 and a pair of partially complementary regions (within 103 and 104) that anneal to each other. Either the sequencing primer regions or immobilization regions may be used to immobilize the barcoded polynucleotides, for example, onto the surface of a bead. The sequencing primer regions may be used, for example, as annealing sites for sequencing primers. In some cases, an overhang may be designed to enable compatibility with a target sequence. In FIG. 1, the pair of annealed polynucleotides 103 and 104 have a 3'-T overhang, which is compatible with the 3'-A overhang on the target polynucleotide 105. A barcode may be included in any suitable portion of a forked adapter. After attachment of the forked adapter comprising the barcode to the target sequence 105, the sequencing primer regions 103 and 104 can be used to sequence the target polynucleotide. Another example of a forked adapter structure includes those used in Illumina™ library preparations and NEBNext® Multiplex Oligos for Illumina available from New England Biolabs™. Examples of non-forked adapters include those disclosed in Merriman et al., *Electrophoresis,* 33(23) 3397-3417 (2012), which is incorporated herein by reference, in its entirety.

Figure 2:
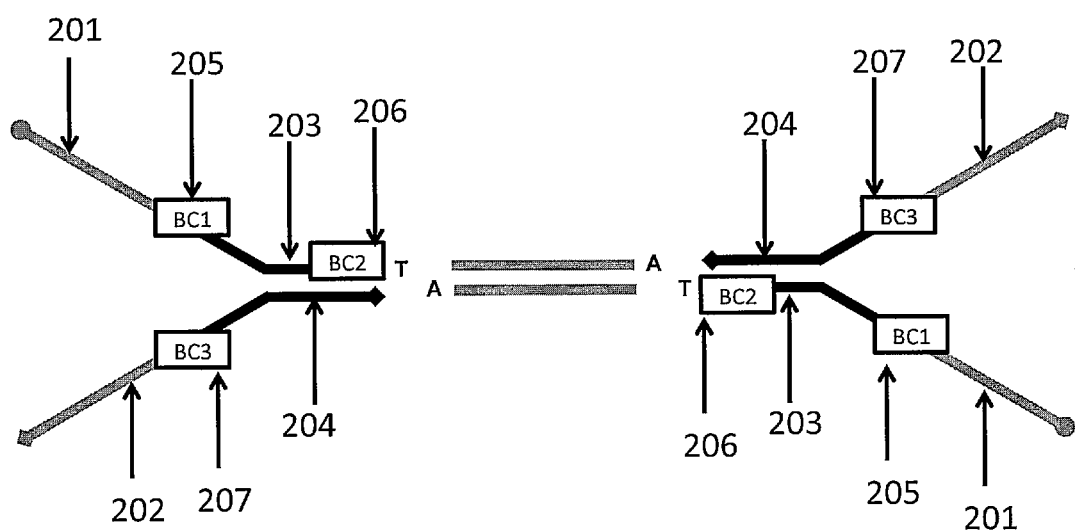
FIG. 2 schematically depicts example placements of barcode regions.

FIG. 2 illustrates three schematic examples of placement of barcode regions within the forked adapter depicted in FIG. 1. In one example, a barcode 205 (BC1) is placed within the first immobilization region 201 or between the first immobilization region 201 and the first sequencing primer region 203. In another example, a barcode 206 (BC2) is placed within or adjacent to the first sequencing primer region 203. In yet another example, a barcode 207 (BC3) is placed within the second immobilization region 202 or between the second immobilization region 202 and the second sequencing primer region 204. Although FIG. 2 depicts barcodes on both ends of the target sequence, this is not necessary, as only one barcode per target sequence is sufficient for some applications. However, as described elsewhere in this disclosure, more than one barcode per target sequence may also be used.

FIG. 3 provides exemplary sequences (SEQ ID NO: 1 and SEQ ID NO: 22) of two forked adapters ligated to opposite ends of a target polynucleotide (NNN) and shows barcode regions of each forked adapter at the sequence level (bolded, nucleotides 30-37, 71-77, 81-87, and 122-129). In FIG. 3, nucleotides 1-29 represent an immobilization region of the first forked adapter, nucleotides 38-70 represent a sequencing primer region of the first forked adapter, nucleotides 78-80 (NNN) represent a target polynucleotide of arbitrary length, nucleotides 88-120 represent a sequencing primer region of the second forked adapter, and nucleotides 129-153 represent an immobilization region of the second forked adapter.

V. PARTITIONS a. General Characteristics of Partitions

As described throughout this disclosure, certain methods, compositions, systems, devices, and kits of the disclosure may utilize the subdivision (partitioning) of certain species into separate partitions. A partition may be, for example, a well, a microwell, a hole, a droplet (e.g., a droplet in an emulsion), a continuous phase of an emulsion, a test tube, a spot, a capsule, a surface of a bead, or any other suitable container for sequestering one fraction of a sample or a species. Partitions may be used to contain a species for further processing. For example, if a species is a polynucleotide analyte, further processing may comprise cutting, ligating, and/or barcoding with species that are reagents. Any number of devices, systems or containers may be used to hold, support or contain partitions. In some cases, a microwell plate may be used to hold, support, or contain partitions. Any suitable microwell plate may be used, for example microwell plates having 96, 384, or 1536 wells.

Each partition may also contain, or be contained within any other suitable partition. For example, a well, microwell, hole, a surface of a bead, or a tube may comprise a droplet (e.g., a droplet in an emulsion), a continuous phase in an emulsion, a spot, a capsule, or any other suitable partition. A droplet may comprise a capsule, bead, or another droplet. A capsule may comprise a droplet, bead, or another capsule. These descriptions are merely illustrative, and all suitable combinations and pluralities are also envisioned. For example, any suitable partition may comprise a plurality of the same or different partitions. In one example, a well or microwell comprises a plurality of droplets and a plurality of capsules. In another example, a capsule comprises a plurality of capsules and a plurality of droplets. All combinations of partitions are envisioned. Table 1 shows non-limiting examples of partitions that may be combined with each other.

TABLE 1

Examples of partitions that may be combined with each other.

| | Well | Spot | Droplet | Capsule |
|---|---|---|---|---|
| Well | Well inside well | Spot inside well | Droplet inside well | Capsule inside well |
| Spot | Spot inside well | Spot inside spot | Droplet inside spot | Capsule inside spot |
| Droplet | Droplet inside well | Droplet inside spot | Droplet inside droplet | Droplet inside capsule Capsule inside droplet |
| Capsule | Capsule inside well | Capsule inside spot Spot inside capsule | Capsule inside droplet Droplet inside capsule | Capsule inside capsule |
| Surface of a Bead | Bead inside well | Spot on bead Bead inside spot | Bead inside droplet | Bead inside capsule |

Any partition described herein may comprise multiple partitions. For example, a partition may comprise 1, 2, 3, 4, 5, 6, 7, 8, 9, 10, 11, 12, 13, 14, 15, 16, 17, 18, 19, 20, 50, 100, 500, 1000, 1500, 2000, 2500, 3000, 3500, 4000, 4500, 5000, 5500, 6000, 6500, 7000, 7500, 8000, 8500, 9000, 9500, 10000, or 50000 partitions. A partition may comprise at least 1, 2, 3, 4, 5, 6, 7, 8, 9, 10, 11, 12, 13, 14, 15, 16, 17, 18, 19, 20, 50, 100, 500, 1000, 1500, 2000, 2500, 3000, 3500, 4000, 4500, 5000, 5500, 6000, 6500, 7000, 7500, 8000, 8500, 9000, 9500, 10000, or 50000 partitions. In some cases, a partition may comprise less than 3, 4, 5, 6, 7, 8, 9, 10, 11, 12, 13, 14, 15, 16, 17, 18, 19, 20, 50, 100, 500, 1000, 1500, 2000, 2500, 3000, 3500, 4000, 4500, 5000, 5500, 6000, 6500, 7000, 7500, 8000, 8500, 9000, 9500, 10000, or 50000 partitions. In some cases, each partition may comprise 2-50, 2-20, 2-10, or 2-5 partitions.

A partition may comprise any suitable species or mixture of species. For example, in some cases a partition may comprise a reagent, an analyte, a sample, a cell, and combinations thereof. A partition comprising other partitions may comprise certain species in the same partitions and certain species in different partitions. Species may be distributed between any suitable partitions, depending on the needs of the particular process. For example, any of the partitions in Table 1 may contain at least one first species and any of the partitions in Table 1 may contain at least one second species. In some cases the first species may be a reagent and the second species may be an analyte.

In some cases, a species is a polynucleotide isolated from a cell. For example, in some cases polynucleotides (e.g., genomic DNA, RNA, etc.) is isolated from a cell utilizing any suitable method (e.g., a commercially available kit). The polynucleotide may be quantified. The quantified polynucleotide may then be partitioned into a plurality of partitions as described herein. The partitioning of the polynucleotide may be performed at a predetermined coverage amount, according to the quantification and the needs of the assay. In some cases, all or most (e.g., at least 50%, 60%, 70%, 80%, 90%, or 95%) of the partitions do not comprise polynucleotides that overlap, such that separate mixtures of non-overlapping fragments are formed across the plurality of partitions. The partitioned polynucleotides may then be treated according to any suitable method known in the art or described in this disclosure. For example, the partitioned polynucleotides may be fragmented, amplified, barcoded, and the like.

Species may be partitioned using a variety of methods. For example, species may be diluted and dispensed across a plurality of partitions. A terminal dilution of a medium comprising species may be performed such that the number of partitions exceeds the number of species. Dilution may also be used prior to forming an emulsion or capsules, or prior to spotting a species on a substrate. The ratio of the number of species to the number of partitions may be about 0.1, 0.5, 1, 2, 4, 8, 10, 20, 50, 100, or 1000. The ratio of the number of species to the number of partitions may be at least about 0.1, 0.5, 1, 2, 4, 8, 10, 20, 50, 100, or 1000. The ratio of the number of species to the number of partitions may be less than about 0.1, 0.5, 1, 2, 4, 8, 10, 20, 50, 100, or 1000. The ratio of the number of species to the number of partitions may range from about 0.1-10, 0.5-10, 1-10, 2-10, 10-100, 100-1000, or more.

Partitioning may also be performed using piezoelectric droplet generation (e.g., Bransky et al., *Lab on a Chip*, 2009, 9, 516-520) or surface acoustic waves (e.g., Demirci and Montesano, *Lab on a Chip*, 2007, 7, 1139-1145).

The number of partitions employed may vary depending on the application. For example, the number of partitions may be about 5, 10, 50, 100, 250, 500, 750, 1000, 1500, 2000, 2500, 5000, 7500, or 10,000, 20000, 30000, 40000, 50000, 60000, 70000, 80000, 90000, 100,000, 200000, 300000, 400000, 500000, 600000, 700000, 800000, 900000, 1,000,000, 2000000, 3000000, 4000000, 5000000, 10000000, 20000000, or more. The number of partitions may be at least about 5, 10, 50, 100, 250, 500, 750, 1000, 1500, 2000, 2500, 5000, 7500, 10,000, 20000, 30000, 40000, 50000, 60000, 70000, 80000, 90000, 100,000, 200000, 300000, 400000, 500000, 600000, 700000, 800000, 900000, 1,000,000, 2000000, 3000000, 4000000, 5000000, 10000000, 20000000, or more. The number of partitions may be less than about 5, 10, 50, 100, 250, 500, 750, 1000, 1500, 2000, 2500, 5000, 7500, 10,000, 20000, 30000, 40000, 50000, 60000, 70000, 80000, 90000, 100,000, 200000, 300000, 400000, 500000, 600000, 700000, 800000, 900000, 1,000,000, 2000000, 3000000, 4000000, 5000000, 10000000, 20000000. The number of partitions may be about 5-10000000, 5-5000000, 5-1,000,000, 10-10,000, 10-5,000, 10-1,000, 1,000-6,000, 1,000-5,000, 1,000-4,000, 1,000-3,000, or 1,000-2,000.

The number of different barcodes or different sets of barcodes that are partitioned may vary depending upon, for example, the particular barcodes to be partitioned and/or the application. Different sets of barcodes may be, for example, sets of identical barcodes where the identical barcodes differ between each set. Or different sets of barcodes may be, for example, sets of different barcodes, where each set differs in its included barcodes. For example, about 1, 5, 10, 50, 100, 1000, 10000, 20,000, 30,000, 40,000, 50,000, 60,000, 70,000, 80,000, 90,000, 100000, 200,000, 300,000, 400,000, 500,000, 600,000, 700,000, 800,000, 900,000, 1000000, 2000000, 3000000, 4000000, 5000000, 6000000, 7000000, 8000000, 9000000, 10000000, 20000000, 50000000, 100000000, or more different barcodes or different sets of barcodes may be partitioned. In some examples, at least about 1, 5, 10, 50, 100, 1000, 10000, 20000, 30000, 40000, 50000, 60000, 70000, 80000, 90000, 100000, 200,000, 300,000, 400,000, 500,000, 600,000, 700,000, 800,000, 900,000, 1000000, 2000000, 3000000, 4000000, 5000000, 6000000, 7000000, 8000000, 9000000, 10000000, 20000000, 50000000, 100000000, or more different barcodes or different sets of barcodes may be partitioned. In some examples, less than about 1, 5, 10, 50, 100, 1000, 10000, 20000, 30000, 40000, 50000, 60000, 70000, 80000, 90000, 100000, 200,000, 300,000, 400,000, 500,000, 600,000, 700,000, 800,000, 900,000, 1000000, 2000000, 3000000, 4000000, 5000000, 6000000, 7000000, 8000000, 9000000, 10000000, 20000000, 50000000, or 100000000 different barcodes or different sets of barcodes may be partitioned. In some examples, about 1-5, 5-10, 10-50, 50-100, 100-1000, 1000-10000, 10000-100000, 100000-1000000, 10000-1000000, 10000-10000000, or 10000-100000000 barcodes may be partitioned.

Barcodes may be partitioned at a particular density. For example, barcodes may be partitioned so that each partition contains about 1, 5, 10, 50, 100, 1000, 10000, 20,000, 30,000, 40,000, 50,000, 60,000, 70,000, 80,000, 90,000, 100000, 200,000, 300,000, 400,000, 500,000, 600,000, 700,000, 800, 000, 900,000, 1000000, 2000000, 3000000, 4000000, 5000000, 6000000, 7000000, 8000000, 9000000, 10000000, 20000000, 50000000, or 100000000 barcodes per partition. Barcodes may be partitioned so that each partition contains at least about 1, 5, 10, 50, 100, 1000, 10000, 20000, 30000, 40000, 50000, 60000, 70000, 80000, 90000, 100000, 200, 000, 300,000, 400,000, 500,000, 600,000, 700,000, 800,000, 900,000, 1000000, 2000000, 3000000, 4000000, 5000000, 6000000, 7000000, 8000000, 9000000, 10000000, 20000000, 50000000, 100000000, or more barcodes per partition. Barcodes may be partitioned so that each partition contains less than about 1, 5, 10, 50, 100, 1000, 10000, 20000, 30000, 40000, 50000, 60000, 70000, 80000, 90000, 100000, 200,000, 300,000, 400,000, 500,000, 600,000, 700,000, 800, 000, 900,000, 1000000, 2000000, 3000000, 4000000, 5000000, 6000000, 7000000, 8000000, 9000000, 10000000, 20000000, 50000000, or 100000000 barcodes per partition. Barcodes may be partitioned such that each partition contains about 1-5, 5-10, 10-50, 50-100, 100-1000, 1000-10000, 10000-100000, 100000-1000000, 10000-1000000, 10000-10000000, or 10000-100000000 barcodes per partition.

Barcodes may be partitioned such that identical barcodes are partitioned at a particular density. For example, identical barcodes may be partitioned so that each partition contains about 1, 5, 10, 50, 100, 1000, 10000, 20,000, 30,000, 40,000, 50,000, 60,000, 70,000, 80,000, 90,000, 100000, 200,000, 300,000, 400,000, 500,000, 600,000, 700,000, 800,000, 900, 000, 1000000, 2000000, 3000000, 4000000, 5000000, 6000000, 7000000, 8000000, 9000000, 10000000, 20000000, 50000000, or 100000000 identical barcodes per partition. Barcodes may be partitioned so that each partition contains at least about 1, 5, 10, 50, 100, 1000, 10000, 20000, 30000, 40000, 50000, 60000, 70000, 80000, 90000, 100000, 200,000, 300,000, 400,000, 500,000, 600,000, 700,000, 800, 000, 900,000, 1000000, 2000000, 3000000, 4000000, 5000000, 6000000, 7000000, 8000000, 9000000, 10000000, 20000000, 50000000, 100000000, or more identical barcodes per partition. Barcodes may be partitioned so that each partition contains less than about 1, 5, 10, 50, 100, 1000, 10000, 20000, 30000, 40000, 50000, 60000, 70000, 80000, 90000, 100000, 200,000, 300,000, 400,000, 500,000, 600,000, 700,000, 800,000, 900,000, 1000000, 2000000, 3000000, 4000000, 5000000, 6000000, 7000000, 8000000, 9000000, 10000000, 20000000, 50000000, or 100000000 identical barcodes per partition. Barcodes may be partitioned such that each partition contains about 1-5, 5-10, 10-50, 50-100, 100-1000, 1000-10000, 10000-100000, 100000-1000000, 10000-1000000, 10000-10000000, or 10000-100000000 identical barcodes per partition.

Barcodes may be partitioned such that different barcodes are partitioned at a particular density. For example, different barcodes may be partitioned so that each partition contains about 1, 5, 10, 50, 100, 1000, 10000, 20,000, 30,000, 40,000, 50,000, 60,000, 70,000, 80,000, 90,000, 100000, 200,000, 300,000, 400,000, 500,000, 600,000, 700,000, 800,000, 900,000, 1000000, 2000000, 3000000, 4000000, 5000000, 6000000, 7000000, 8000000, 9000000, 10000000, 20000000, 50000000, or 100000000 different barcodes per partition. Barcodes may be partitioned so that each partition contains at least about 1, 5, 10, 50, 100, 1000, 10000, 20000, 30000, 40000, 50000, 60000, 70000, 80000, 90000, 100000, 200,000, 300,000, 400,000, 500,000, 600,000, 700,000, 800,000, 900,000, 1000000, 2000000, 3000000, 4000000, 5000000, 6000000, 7000000, 8000000, 9000000, 10000000, 20000000, 50000000, 100000000, or more different barcodes per partition. Barcodes may be partitioned so that each partition contains less than about 1, 5, 10, 50, 100, 1000, 10000, 20000, 30000, 40000, 50000, 60000, 70000, 80000, 90000, 100000, 200,000, 300,000, 400,000, 500,000, 600,000, 700,000, 800,000, 900,000, 1000000, 2000000, 3000000, 4000000, 5000000, 6000000, 7000000, 8000000, 9000000, 10000000, 20000000, 50000000, or 100000000 different barcodes per partition. Barcodes may be partitioned such that each partition contains about 1-5, 5-10, 10-50, 50-100, 100-1000, 1000-10000, 10000-100000, 100000-1000000, 10000-1000000, 10000-10000000, or 10000-100000000 different barcodes per partition.

The number of partitions employed to partition barcodes may vary, for example, depending on the application and/or the number of different barcodes to be partitioned. For example, the number of partitions employed to partition barcodes may be about 5, 10, 50, 100, 250, 500, 750, 1000, 1500, 2000, 2500, 5000, 7500, or 10,000, 20000, 30000, 40000, 50000, 60000, 70000, 80000, 90000, 100,000, 200000, 300000, 400000, 500000, 600000, 700000, 800000, 900000, 1,000,000, 2000000, 3000000, 4000000, 5000000, 10000000, 20000000 or more. The number of partitions employed to partition barcodes may be at least about 5, 10, 50, 100, 250, 500, 750, 1000, 1500, 2000, 2500, 5000, 7500, 10,000, 20000, 30000, 40000, 50000, 60000, 70000, 80000, 90000, 100000, 200000, 300000, 400000, 500000, 600000, 700000, 800000, 900000, 1000000, 2000000, 3000000, 4000000, 5000000, 10000000, 20000000 or more. The number of partitions employed to partition barcodes may be less than about 5, 10, 50, 100, 250, 500, 750, 1000, 1500, 2000, 2500, 5000, 7500, 10,000, 20000, 30000, 40000, 50000, 60000, 70000, 80000, 90000, 100000, 200000, 300000, 400000, 500000, 600000, 700000, 800000, 900000, 1000000, 2000000, 3000000, 4000000, 5000000, 10000000, or 20000000. The number of partitions employed to partition barcodes may be about 5-10000000, 5-5000000, 5-1,000,000, 10-10,000, 10-5,000, 10-1,000, 1,000-6,000, 1,000-5,000, 1,000-4,000, 1,000-3,000, or 1,000-2,000.

As described above, different barcodes or different sets of barcodes (e.g., each set comprising a plurality of identical barcodes or different barcodes) may be partitioned such that each partition comprises a different barcode or different barcode set. In some cases, each partition may comprise a different set of identical barcodes. Where different sets of identical barcodes are partitioned, the number of identical barcodes per partition may vary. For example, about 100,000 or more different sets of identical barcodes may be partitioned across about 100,000 or more different partitions, such that each partition comprises a different set of identical barcodes. In each partition, the number of identical barcodes per set of barcodes may be about 1,000,000 identical barcodes. In some cases, the number of different sets of barcodes may be equal to or substantially equal to the number of partitions. Any suitable number of different barcodes or different barcode sets (including numbers of different barcodes or different barcode sets to be partitioned described elsewhere herein), number of barcodes per partition (including numbers of barcodes per partition described elsewhere herein), and number of partitions (including numbers of partitions described elsewhere herein) may be combined to generate a diverse library of partitioned barcodes with high numbers of barcodes per partition. Thus, as will be appreciated, any of the above-described different numbers of barcodes may be provided with any of the above-described barcode densities per partition, and in any of the above-described numbers of partitions.

The volume of the partitions may vary depending on the application. For example, the volume of any of the partitions described in this disclosure (e.g., wells, spots, droplets (e.g., in an emulsion), and capsules) may be about 1000 µl, 900 µl, 800 µl, 700 µl, 600 µl, 500 µl, 400 µl, 300 µl, 200 µl, 100 µl, 50 µl, 25 µl, 10 µl, 5 µl, 1 µl, 900 nL, 800 nL, 700 nL, 600 nL, 500 nL, 400 nL, 300 nL, 200 nL, 100 nL, 50 nL, 25 nL, 10 nL, 5 nL, 2.5 nL, 1 nL, 900 pL, 800 pL, 700 pL, 600 pL, 500 pL, 400 pL, 300 pL, 200 pL, 100 pL, 50 pL, 25 pL, 10 pL, 5 pL, 1 pL, 900 fL, 800 fL, 700 fL, 600 fL, 500 fL, 400 fL, 300 fL, 200 fL, 100 fL, 50 fL, 25 fL, 10 fL, 5 fL, 1 fL, or 0.5 fL. The volume of the partitions may be at least about 1000 µl, 900 µl, 800 µl, 700 µl, 600 µl, 500 µl, 400 µl, 300 µl, 200 µl, 100 µl, 50 µl, 25 µl, 10 µl, 5 µl, 1 µl, 900 nL, 800 nL, 700 nL, 600 nL, 500 nL, 400 nL, 300 nL, 200 nL, 100 nL, 50 nL, 25 nL, 10 nL, 5 nL, 5 nL, 2.5 nL, 1 nL, 900 pL, 800 pL, 700 pL, 600 pL, 500 pL, 400 pL, 300 pL, 200 pL, 100 pL, 50 pL, 25 pL, 10 pL, 5 pL, 1 pL, 900 fL, 800 fL, 700 fL, 600 fL, 500 fL, 400 fL, 300 fL, 200 fL, 100 fL, 50 fL, 25 fL, 10 fL, 5 fL, 1 fL, or 0.5 fL. The volume of the partitions may be less than about 1000 µl, 900 µl, 800 µl, 700 µl, 600 µl, 500 µl, 400 µl, 300 µl, 200 µl, 100 µl, 50 µl, 25 µl, 10 µl, 5 µl, 1 µl, 900 nL, 800 nL, 700 nL, 600 nL, 500 nL, 400 nL, 300 nL, 200 nL, 100 nL, 50 nL, 25 nL, 10 nL, 5 nL, 5 nL, 2.5 nL, 1 nL, 900 pL, 800 pL, 700 pL, 600 pL, 500 pL, 400 pL, 300 pL, 200 pL, 100 pL, 50 pL, 25 pL, 10 pL, 5 pL, 1 pL, 900 fL, 800 fL, 700 fL, 600 fL, 500 fL, 400 fL, 300 fL, 200 fL, 100 fL, 50 fL, 25 fL, 10 fL, 5 fL, 1 fL, or 0.5 fL. the volume of the partitions may be about 0.5 fL-5 pL, 10 pL-10 nL, 10 nL-10 µl, 10 µl-100 µl, or 100 µl to 1 mL.

There may be variability in the volume of fluid in different partitions. More specifically, the volume of different partitions may vary by at least (or at most) plus or minus 1%, 2%, 3%, 4%, 5%, 10%, 20%, 30%, 40%, 50%, 60%, 70%, 80%, 90%, 100%, 200%, 300%, 400%, 500%, or 1000% across a set of partitions. For example, a well (or other partition) may comprise a volume of fluid that is at most 80% of the fluid volume within a second well (or other partition).

Particular species may also be targeted to specific partitions. For example, in some cases, a capture reagent (e.g., an oligonucleotide probe) may be immobilized or placed within a partition to capture specific species (e.g., polynucleotides). For example, a capture oligonucleotide may be immobilized on the surface of a bead in order to capture a species comprising an oligonucleotide with a complementary sequence.

Species may also be partitioned at a particular density. For example, species may be partitioned so that each partition contains about 1, 5, 10, 50, 100, 1000, 10000, 100000, or 1000000 species per partition. Species may be partitioned so that each partition contains at least about 1, 5, 10, 50, 100, 1000, 10000, 100000, 1000000 or more species per partition. Species may be partitioned so that each partition contains less than about 1, 5, 10, 50, 100, 1000, 10000, 100000, or 1000000 species per partition. Species may be partitioned such that each partition contains about 1-5, 5-10, 10-50, 50-100, 100-1000, 1000-10000, 10000-100000, or 100000-1000000 species per partition.

Species may be partitioned such that at least one partition comprises a species that is unique within that partition. This may be true for about 1%, 5%, 10%, 20%, 30%, 40%, 50%, 60%, 70%, 80%, 90%, or more of the partitions. This may be true for at least about 1%, 5%, 10%, 20%, 30%, 40%, 50%, 60%, 70%, 80%, 90%, or more of the partitions. This may be true for less than about 1%, 5%, 10%, 20%, 30%, 40%, 50%, 60%, 70%, 80%, or 90% of the partitions.

a. Wells as Partitions

In some cases, wells are used as partitions. The wells may be microwells. A well may comprise a medium comprising a species or plurality of species. Species may be contained within a well in various configurations. In one example, a species is dispensed directly into a well. A species dispensed directly into a well may be overlaid with a layer that is, for example, dissolvable, meltable, or permeable. This layer may be, for example, an oil, wax, membrane, or the like. The layer may be dissolved or melted prior to or after introduction of another species into the well. The well may be sealed at any point, with a sealing layer, for example after addition of any species.

In one example, reagents for sample processing are dispensed directly into a well and overlaid with a layer that is dissolvable, meltable, or permeable. A sample comprising an analyte to be processed is introduced on top of the layer. The layer is dissolved or melted, or the analyte (or reagent) diffuses through the layer. The well is sealed and incubated under appropriate conditions for the processing of the analyte. Processed analyte may then be recovered.

In some cases, wells comprise other partitions. A well may comprise any suitable partition including, for example, another well, a spot, a droplet (e.g., a droplet in an emulsion), a capsule, a bead, and the like. Each partition may be present as a single partition or a plurality of partitions, and each partition may comprise the same species or different species.

In one example, a well comprises a capsule comprising reagents for sample processing. A capsule may be loaded into a well using a liquid medium, or loaded into a well without a liquid medium (e.g., essentially dry). As described elsewhere in this disclosure, a capsule may contain one or more capsules, or other partitions. A sample comprising an analyte to be processed may be introduced into the well. The well may be sealed and a stimulus may be applied to cause release of the contents of the capsule into the well, resulting in contact between the reagents and the analyte to be processed. The well may be incubated under appropriate conditions for the processing of the analyte. Processed analyte may then be recovered. While this example describes an embodiment where a reagent is in a capsule and an analyte is in the well, the opposite configuration—i.e., reagent in the well and analyte in the capsule—is also possible.

In another example, a well comprises an emulsion and the droplets of the emulsion comprise capsules comprising reagents for sample processing. A sample comprising an analyte to be processed is contained within the droplets of the emulsion. The well is sealed and a stimulus is applied to cause release of the contents of the capsules into the droplets, resulting in contact between the reagents and the analyte to be processed. The well is incubated under appropriate conditions for the processing of the analyte. Processed analyte may then be recovered. While this example describes an embodiment where a reagent is in a capsule and an analyte is in a droplet, the opposite configuration—i.e., reagent in the droplet and analyte in the capsule—is also possible.

Wells may be arranged as an array, for example a microwell array. Based on the dimensions of individual wells and the size of the substrate, the well array may comprise a range of well densities. In some cases, the well density may be 10 wells/cm$^2$, 50 wells/cm$^2$, 100 wells/cm$^2$, 500 wells/cm$^2$, 1000 wells/cm$^2$, 5000 wells/cm$^2$, 10000 wells/cm$^2$, 50000 wells/cm$^2$, or 100000 wells/cm$^2$. In some cases, the well density may be at least 10 wells/cm$^2$, 50 wells/cm$^2$, 100 wells/cm$^2$, 500 wells/cm$^2$, 1000 wells/cm$^2$, 5000 wells/cm$^2$, 10000 wells/cm$^2$, 50000 wells/cm$^2$, or 100000 wells/cm$^2$. In some cases, the well density may be less than 10 wells/cm$^2$, 50 wells/cm$^2$, 100 wells/cm$^2$, 500 wells/cm$^2$, 1000 wells/cm$^2$, 5000 wells/cm$^2$, 10000 wells/cm$^2$, 50000 wells/cm$^2$, or 100000 wells/cm$^2$.

b. Spots as Partitions

In some cases, spots are used as partitions. A spot may be made, for example, by dispensing a substance on a surface. Species may be contained within a spot in various configurations. In one example, a species is dispensed directly into a spot by including the species in the medium used to form the spot. A species dispensed directly onto a spot may be overlaid with a layer that is, for example, dissolvable, meltable, or permeable. This layer may be, for example, an oil, wax, membrane, or the like. The layer may be dissolved or melted prior to or after introduction of another species onto the spot. The spot may be sealed at any point, for example after addition of any species, by an overlay.

In one example, reagents for sample processing are dispensed directly onto a spot, for example on a glass slide, and overlaid with a layer that is dissolvable, meltable, or permeable. A sample comprising an analyte to be processed is introduced on top of the layer. The layer is dissolved or melted, or the analyte (or reagent) diffuses through the layer. The spot is sealed and incubated under appropriate conditions for the processing of the analyte. Processed analyte may then be recovered.

As described elsewhere in this disclosure (e.g., Table 1), spots may also be arranged within a well. In some cases, a plurality of spots may be arranged within a well such that the contents of each spot do not mix. Such a configuration may be useful, for example, when it is desirable to prevent species from contacting each other. In some cases, a well may comprise 2, 3, 4, 5, 6, 7, 8, 9, 10, 11, 12, 13, 14, 15, 16, 17, 18, 19, 20, 21, 22, 23, 24, 25, 26, 27, 28, 29, 30, or more spots. In some cases, a well may comprise at least 2, 3, 4, 5, 6, 7, 8, 9, 10, 11, 12, 13, 14, 15, 16, 17, 18, 19, 20, 21, 22, 23, 24, 25, 26, 27, 28, 29, 30, or more spots. In some cases, a well may comprise less than 2, 3, 4, 5, 6, 7, 8, 9, 10, 11, 12, 13, 14, 15, 16, 17, 18, 19, 20, 21, 22, 23, 24, 25, 26, 27, 28, 29, or 30 spots. In some cases, a well may comprise 2-4, 2-6, 2-8, 4-6, 4-8, 5-10, or 4-12 spots. Upon addition of a substance (e.g., a medium containing an analyte) to the well, the species in the spot may mix. Moreover, using separate spots to contain different species (or combinations of species) may also be useful to prevent cross-contamination of devices used to place the spots inside the well.

In some cases, spots comprise other partitions. A spot may comprise any suitable partition including, for example, another spot a droplet (e.g., a droplet in an emulsion), a capsule, a bead, and the like. Each partition may be present as a single partition or a plurality of partitions, and each partition may comprise the same species or different species.

In one example, a spot comprises a capsule comprising reagents for sample processing. As described elsewhere in this disclosure, a capsule may contain one or more capsules, or other partitions. A sample comprising an analyte to be processed is introduced into the spot. The spot is sealed and a stimulus is applied to cause release of the contents of the capsule into the spot, resulting in contact between the reagents and the analyte to be processed. The spot is incubated under appropriate conditions for the processing of the analyte. Processed analyte may then be recovered. While this example describes an embodiment where a reagent is in a capsule and an analyte is in the spot, the opposite configuration—i.e., reagent in the spot and analyte in the capsule—is also possible.

In another example, a spot comprises an emulsion and the droplets of the emulsion comprise capsules comprising reagents for sample processing. A sample comprising an analyte to be processed is contained within the droplets of the emulsion. The spot is sealed and a stimulus is applied to cause release of the contents of the capsules into the droplets, resulting in contact between the reagents and the analyte to be processed. The spot is incubated under appropriate conditions for the processing of the analyte. Processed analyte may then be recovered. While this example describes an embodiment where a reagent is in a capsule and an analyte is in a droplet, the opposite configuration—i.e., reagent in the droplet and analyte in the capsule—is also possible.

Spots may be of uniform size or heterogeneous size. In some cases, the diameter of a spot may be about 0.1 µm, 0.5 µm, 1 µm, 5 µm, 10 µm, 50 µm, 100 µm, 150 µm, 200 µm, 300 µm, 400 µm, 500 µm, 600 µm, 700 µm, 800 µm, 900 µm, 1 mm, 2 mm, 5 mm, or 1 cm. A spot may have a diameter of at least about 0.1 µm, 0.5 µm, 1 µm, 5 µm, 10 µm, 50 µm, 100 µm, 150 µm, 200 µm, 300 µm, 400 µm, 500 µm, 600 µm, 700 µm, 800 µm, 900 µm, 1 mm, 1 mm, 2 mm, 5 mm, or 1 cm. In some cases, a spot may have a diameter of less than about 0.1 µm, 0.5 µm, 1 µm, 5 µm, 10 µm, 50 µm, 100 µm, 150 µm, 200 µm, 300 µm, 400 µm, 500 µm, 600 µm, 700 µm, 800 µm, 900 µm, 1 mm, 1 mm, 2 mm, 5 mm, or 1 cm. In some cases, a spot may have a diameter of about 0.1 µm to 1 cm, 100 µm to 1 mm, 100 µm to 500 µm, 100 µm to 600 µm, 150 µm to 300 µm, or 150 µm to 400 µm.

Spots may be arranged as an array, for example a spot array. Based on the dimensions of individual spots and the size of the substrate, the spot array may comprise a range of spot densities. In some cases, the spot density may be 10 spots/cm$^2$, 50 spots/cm$^2$, 100 spots/cm$^2$, 500 spots/cm$^2$, 1000 spots/cm$^2$, 5000 spots/cm$^2$, 10000 spots/cm$^2$, 50000 spots/cm$^2$, or 100000 spots/cm$^2$. In some cases, the spot density may be at least 10 spots/cm$^2$, 50 spots/cm$^2$, 100 spots/cm$^2$, 500 spots/cm$^2$, 1000 spots/cm$^2$, 5000 spots/cm$^2$, 10000 spots/cm$^2$, 50000 spots/cm$^2$, or 100000 spots/cm$^2$. In some cases, the spot density may be less than 10 spots/cm$^2$, 50 spots/cm$^2$, 100 spots/cm$^2$, 500 spots/cm$^2$, 1000 spots/cm$^2$, 5000 spots/cm$^2$, 10000 spots/cm$^2$, 50000 spots/cm$^2$, or 100000 spots/cm$^2$.

c. Emulsions as Partitions

In some cases, the droplets in an emulsion are used as partitions. An emulsion may be prepared, for example, by any suitable method, including methods known in the art. (See e.g., Weizmann et al., Nature Methods, 2006, 3(7):545-550; Weitz et al. U.S. Pub. No. 2012/0211084). In some cases, water-in-fluorocarbon emulsions may be used. These emulsions may incorporate fluorosurfactants such as oligomeric perfluorinated polyethers (PFPE) with polyethylene glycol (PEG). (Holtze et al., Lab on a Chip, 2008, 8(10):1632-1639). In some cases, monodisperse emulsions may be formed in a microfluidic flow focusing device. (Garstecki et al., Applied Physics Letters, 2004, 85(13):2649-2651).

A species may be contained within a droplet in an emulsion containing, for example, a first phase (e.g., oil or water) forming the droplet and a second (continuous) phase (e.g., water or oil). An emulsion may be a single emulsion, for example, a water-in-oil or an oil-in-water emulsion. An emulsion may be a double emulsion, for example a water-in-oil-in-water or an oil-in-water-in-oil emulsion. Higher-order emulsions are also possible. The emulsion may be held in any suitable container, including any suitable partition described in this disclosure.

In some cases, droplets in an emulsion comprise other partitions. A droplet in an emulsion may comprise any suitable partition including, for example, another droplet (e.g., a droplet in an emulsion), a capsule, a bead, and the like. Each partition may be present as a single partition or a plurality of partitions, and each partition may comprise the same species or different species.

In one example, a droplet in an emulsion comprises a capsule comprising reagents for sample processing. As described elsewhere in this disclosure, a capsule may contain one or more capsules, or other partitions. A sample comprising an analyte to be processed is contained within the droplet. A stimulus is applied to cause release of the contents of the capsule into the droplet, resulting in contact between the reagents and the analyte to be processed. The droplet is incubated under appropriate conditions for the processing of the analyte. Processed analyte may then be recovered. While this example describes an embodiment where a reagent is in a capsule and an analyte is in the droplet, the opposite configuration—i.e., reagent in the droplet and analyte in the capsule—is also possible.

The droplets in an emulsion may be of uniform size or heterogeneous size. In some cases, the diameter of a droplet in an emulsion may be about 0.001 µm, 0.01 µm, 0.05 µm, 0.1 µm, 0.5 µm, 1 µm, 5 µm, 10 µm, 50 µm, 100 µm, 150 µm, 200 µm, 300 µm, 400 µm, 500 µm, 600 µm, 700 µm, 800 µm, 900 µm, or 1 mm. A droplet may have a diameter of at least about 0.001 µm, 0.01 µm, 0.05 µm, 0.1 µm, 0.5 µm, 1 µm, 5 µm, 10 µm, 50 µm, 100 µm, 150 µm, 200 µm, 300 µm, 400 µm, 500 µm, 600 µm, 700 µm, 800 µm, 900 µm, or 1 mm. In some cases, a droplet may have a diameter of less than about 0.001 µm, 0.01 µm, 0.05 µm, 0.1 µm, 0.5 µm, 1 µm, 5 µm, 10 µm, 50 µm, 100 µm, 150 µm, 200 µm, 300 µm, 400 µm, 500 µm, 600 µm, 700 µm, 800 µm, 900 µm, or 1 mm. In some cases, a droplet may have a diameter of about 0.001 µm to 1 mm, 0.01 µm to 900 µm, 0.1 µm to 600 µm, 100 µm to 200 µm, 100 µm to 300 µm, 100 µm to 400 µm, 100 µm to 500 µm, 100 µm to 600 µm, 150 µm to 200 µm, 150 µm to 300 µm, or 150 µm to 400 µm.

Droplets in an emulsion also may have a particular density. In some cases, the droplets are less dense than an aqueous fluid (e.g., water); in some cases, the droplets are denser than an aqueous fluid. In some cases, the droplets are less dense than a non-aqueous fluid (e.g., oil); in some cases, the droplets are denser than a non-aqueous fluid. Droplets may have a density of about 0.05 g/cm$^3$, 0.1 g/cm$^3$, 0.2 g/cm$^3$, 0.3 g/cm$^3$, 0.4 g/cm$^3$, 0.5 g/cm$^3$, 0.6 g/cm$^3$, 0.7 g/cm$^3$, 0.8 g/cm$^3$, 0.81 g/cm$^3$, 0.82 g/cm$^3$, 0.83 g/cm$^3$, 0.84 g/cm$^3$, 0.85 g/cm$^3$, 0.86 g/cm$^3$, 0.87 g/cm$^3$, 0.88 g/cm$^3$, 0.89 g/cm$^3$, 0.90 g/cm$^3$, 0.91 g/cm$^3$, 0.92 g/cm$^3$, 0.93 g/cm$^3$, 0.94 g/cm$^3$, 0.95 g/cm$^3$, 0.96 g/cm$^3$, 0.97 g/cm$^3$, 0.98 g/cm$^3$, 0.99 g/cm$^3$, 1.00 g/cm$^3$, 1.05 g/cm$^3$, 1.1 g/cm$^3$, 1.2 g/cm$^3$, 1.3 g/cm$^3$, 1.4 g/cm$^3$, 1.5 g/cm$^3$, 1.6 g/cm$^3$, 1.7 g/cm$^3$, 1.8 g/cm$^3$, 1.9 g/cm$^3$, 2.0 g/cm$^3$, 2.1 g/cm$^3$, 2.2 g/cm$^3$, 2.3 g/cm$^3$, 2.4 g/cm$^3$, or 2.5 g/cm$^3$. Droplets may have a density of at least about 0.05 g/cm$^3$, 0.1 g/cm$^3$, 0.2 g/cm$^3$, 0.3 g/cm$^3$, 0.4 g/cm$^3$, 0.5 g/cm$^3$, 0.6 g/cm$^3$, 0.7 g/cm$^3$, 0.8 g/cm$^3$, 0.81 g/cm$^3$, 0.82 g/cm$^3$, 0.83 g/cm$^3$, 0.84 g/cm$^3$, 0.85 g/cm$^3$, 0.86 g/cm$^3$, 0.87 g/cm$^3$, 0.88 g/cm$^3$, 0.89 g/cm$^3$, 0.90 g/cm$^3$, 0.91 g/cm$^3$, 0.92 g/cm$^3$, 0.93 g/cm$^3$, 0.94 g/cm$^3$, 0.95 g/cm$^3$, 0.96 g/cm$^3$, 0.97 g/cm$^3$, 0.98 g/cm$^3$, 0.99 g/cm$^3$, 1.00 g/cm$^3$, 1.05 g/cm$^3$, 1.1 g/cm$^3$, 1.2 g/cm$^3$, 1.3 g/cm$^3$, 1.4 g/cm$^3$, 1.5 g/cm$^3$, 1.6 g/cm$^3$, 1.7 g/cm$^3$, 1.8 g/cm$^3$, 1.9 g/cm$^3$, 2.0 g/cm$^3$, 2.1 g/cm$^3$, 2.2 g/cm$^3$, 2.3 g/cm$^3$, 2.4 g/cm$^3$, or 2.5 g/cm$^3$. In other cases, droplet densities may be at most about 0.7 g/cm$^3$, 0.8 g/cm$^3$, 0.81 g/cm$^3$, 0.82 g/cm$^3$, 0.83 g/cm$^3$, 0.84 g/cm$^3$, 0.85 g/cm$^3$, 0.86 g/cm$^3$, 0.87 g/cm$^3$, 0.88 g/cm$^3$, 0.89 g/cm$^3$, 0.90 g/cm$^3$, 0.91 g/cm$^3$, 0.92 g/cm$^3$, 0.93 g/cm$^3$, 0.94 g/cm$^3$, 0.95 g/cm$^3$, 0.96 g/cm$^3$, 0.97 g/cm$^3$, 0.98 g/cm$^3$, 0.99 g/cm$^3$, 1.00 g/cm$^3$, 1.05 g/cm$^3$, 1.1 g/cm$^3$, 1.2 g/cm$^3$, 1.3 g/cm$^3$, 1.4 g/cm$^3$, 1.5 g/cm$^3$, 1.6 g/cm$^3$, 1.7 g/cm$^3$, 1.8 g/cm$^3$, 1.9 g/cm$^3$, 2.0 g/cm$^3$, 2.1 g/cm$^3$, 2.2 g/cm$^3$, 2.3 g/cm$^3$, 2.4 g/cm$^3$, or 2.5 g/cm$^3$. Such densities can reflect the density of the capsule in any particular fluid (e.g., aqueous, water, oil, etc.)

d. Capsules as Partitions

In some cases, capsules are used as partitions. A capsule may be prepared by any suitable method, including methods known in the art, including emulsification polymerization (Weitz et al. (U.S. Pub. No. 2012/0211084)), layer-by-layer assembly with polyelectrolytes, coacervation, internal phase separation, and flow focusing. Any suitable species may be contained within a capsule. The capsule may be held in any suitable container, including any suitable partition described in this disclosure.

In some cases, capsules comprise other partitions. A capsule may comprise any suitable partition including, for example, another capsule, a droplet in an emulsion, a bead, and the like. Each partition may be present as a single partition or a plurality of partitions, and each partition may comprise the same species or different species.

In one example, an outer capsule comprises an inner capsule. The inner capsule comprises reagents for sample processing. An analyte is encapsulated in the medium between the inner capsule and the outer capsule. A stimulus is applied to cause release of the contents of the inner capsule into the outer capsule, resulting in contact between the reagents and the analyte to be processed. The outer capsule is incubated under appropriate conditions for the processing of the analyte. Processed analyte may then be recovered. While this example describes an embodiment where a reagent is in an inner capsule and an analyte in the medium between the inner capsule and the outer capsule, the opposite configuration—i.e., reagent in the medium between the inner capsule and the outer capsule, and analyte in the inner capsule—is also possible.

Capsules may be pre-formed and filled with reagents by injection. For example, the picoinjection methods described in Abate et al. (Proc. Natl. Acad. Sci. U.S.A., 2010, 107(45), 19163-19166) and Weitz et al. (U.S. Pub. No. 2012/0132288) may be used to introduce reagents into the interior of capsules described herein. Generally, the picoinjection will be performed prior to the hardening of the capsule shell, for example by injecting species into the interior of a capsule precursor, such as a droplet of an emulsion, before formation of the capsule shell.

Capsules may be of uniform size or heterogeneous size. In some cases, the diameter of a capsule may be about 0.001 μm, 0.01 μm, 0.05 μm, 0.1 μm, 0.5 μm, 1 μm, 5 μm, 10 μm, 50 μm, 100 μm, 150 μm, 200 μm, 300 μm, 400 μm, 500 μm, 600 μm, 700 μm, 800 μm, 900 μm, or 1 mm. A capsule may have a diameter of at least about 0.001 μm, 0.01 μm, 0.05 μm, 0.1 μm, 0.5 μm, 1 μm, 5 μm, 10 μm, 50 μm, 100 μm, 150 μm, 200 μm, 300 μm, 400 μm, 500 μm, 600 μm, 700 μm, 800 μm, 900 μm, or 1 mm. In some cases, a capsule may have a diameter of less than about 0.001 μm, 0.01 μm, 0.05 μm, 0.1 μm, 0.5 μm, 1 μm, 5 μm, 10 μm, 50 μm, 100 μm, 150 μm, 200 μm, 300 μm, 400 μm, 500 μm, 600 μm, 700 μm, 800 μm, 900 μm, or 1 mm. In some cases, a capsule may have a diameter of about 0.001 μm to 1 mm, 0.01 μm to 900 μm, 0.1 μm to 600 μm, 100 μm to 200 μm, 100 μm to 300 μm, 100 μm to 400 μm, 100 μm to 500 μm, 100 μm to 600 μm, 150 μm to 200 μm, 150 μm to 300 μm, or 150 μm to 400 μm.

Capsules also may have a particular density. In some cases, the capsules are less dense than an aqueous fluid (e.g., water); in some cases, the capsules are denser than an aqueous fluid. In some cases, the capsules are less dense than a non-aqueous fluid (e.g., oil); in some cases, the capsules are denser than a non-aqueous fluid. Capsules may have a density of about 0.05 g/cm$^3$, 0.1 g/cm$^3$, 0.2 g/cm$^3$, 0.3 g/cm$^3$, 0.4 g/cm$^3$, 0.5 g/cm$^3$, 0.6 g/cm$^3$, 0.7 g/cm$^3$, 0.8 g/cm$^3$, 0.81 g/cm$^3$, 0.82 g/cm$^3$, 0.83 g/cm$^3$, 0.84 g/cm$^3$, 0.85 g/cm$^3$, 0.86 g/cm$^3$, 0.87 g/cm$^3$, 0.88 g/cm$^3$, 0.89 g/cm$^3$, 0.90 g/cm$^3$, 0.91 g/cm$^3$, 0.92 g/cm$^3$, 0.93 g/cm$^3$, 0.94 g/cm$^3$, 0.95 g/cm$^3$, 0.96 g/cm$^3$, 0.97 g/cm$^3$, 0.98 g/cm$^3$, 0.99 g/cm$^3$, 1.00 g/cm$^3$, 1.05 g/cm$^3$, 1.1 g/cm$^3$, 1.2 g/cm$^3$, 1.3 g/cm$^3$, 1.4 g/cm$^3$, 1.5 g/cm$^3$, 1.6 g/cm$^3$, 1.7 g/cm$^3$, 1.8 g/cm$^3$, 1.9 g/cm$^3$, 2.0 g/cm$^3$, 2.1 g/cm$^3$, 2.2 g/cm$^3$, 2.3 g/cm$^3$, 2.4 g/cm$^3$, or 2.5 g/cm$^3$. Capsules may have a density of at least about 0.05 g/cm$^3$, 0.1 g/cm$^3$, 0.2 g/cm$^3$, 0.3 g/cm$^3$, 0.4 g/cm$^3$, 0.5 g/cm$^3$, 0.6 g/cm$^3$, 0.7 g/cm$^3$, 0.8 g/cm$^3$, 0.81 g/cm$^3$, 0.82 g/cm$^3$, 0.83 g/cm$^3$, 0.84 g/cm$^3$, 0.85 g/cm$^3$, 0.86 g/cm$^3$, 0.87 g/cm$^3$, 0.88 g/cm$^3$, 0.89 g/cm$^3$, 0.90 g/cm$^3$, 0.91 g/cm$^3$, 0.92 g/cm$^3$, 0.93 g/cm$^3$, 0.94 g/cm$^3$, 0.95 g/cm$^3$, 0.96 g/cm$^3$, 0.97 g/cm$^3$, 0.98 g/cm$^3$, 0.99 g/cm$^3$, 1.00 g/cm$^3$, 1.05 g/cm$^3$, 1.1 g/cm$^3$, 1.2 g/cm$^3$, 1.3 g/cm$^3$, 1.4 g/cm$^3$, 1.5 g/cm$^3$, 1.6 g/cm$^3$, 1.7 g/cm$^3$, 1.8 g/cm$^3$, 1.9 g/cm$^3$, 2.0 g/cm$^3$, 2.1 g/cm$^3$, 2.2 g/cm$^3$, 2.3 g/cm$^3$, 2.4 g/cm$^3$, or 2.5 g/cm$^3$. In other cases, capsule densities may be at most about 0.7 g/cm$^3$, 0.8 g/cm$^3$, 0.81 g/cm$^3$, 0.82 g/cm$^3$, 0.83 g/cm$^3$, 0.84 g/cm$^3$, 0.85 g/cm$^3$, 0.86 g/cm$^3$, 0.87 g/cm$^3$, 0.88 g/cm$^3$, 0.89 g/cm$^3$, 0.90 g/cm$^3$, 0.91 g/cm$^3$, 0.92 g/cm$^3$, 0.93 g/cm$^3$, 0.94 g/cm$^3$, 0.95 g/cm$^3$, 0.96 g/cm$^3$, 0.97 g/cm$^3$, 0.98 g/cm$^3$, 0.99 g/cm$^3$, 1.00 g/cm$^3$, 1.05 g/cm$^3$, 1.1 g/cm$^3$, 1.2 g/cm$^3$, 1.3 g/cm$^3$, 1.4 g/cm$^3$, 1.5 g/cm$^3$, 1.6 g/cm$^3$, 1.7 g/cm$^3$, 1.8 g/cm$^3$, 1.9 g/cm$^3$, 2.0 g/cm$^3$, 2.1 g/cm$^3$, 2.2 g/cm$^3$, 2.3 g/cm$^3$, 2.4 g/cm$^3$, or 2.5 g/cm$^3$. Such densities can reflect the density of the capsule in any particular fluid (e.g., aqueous, water, oil, etc.)

1. Production of Capsules by Flow Focusing

Figure 12:
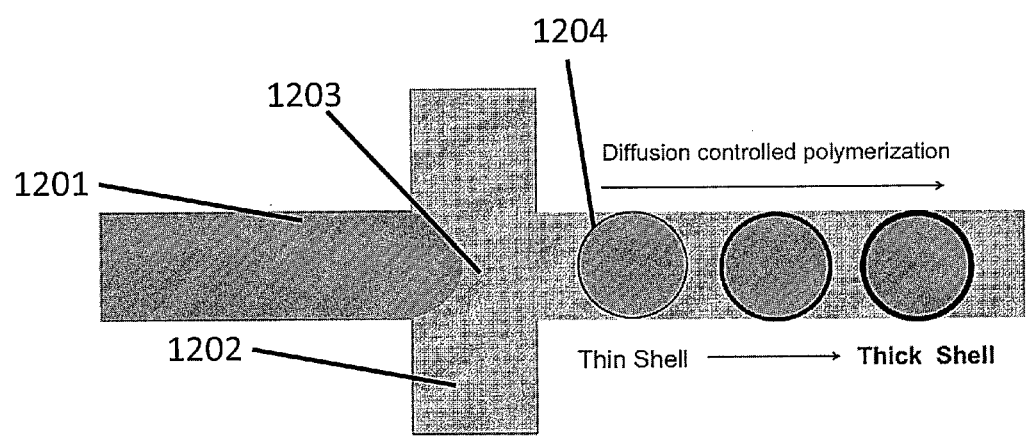
FIG. 12 schematically depicts the production capsules via an example flow-focusing method.

In some cases, capsules may be produced by flow focusing. Flow focusing is a method whereby a first fluid that is immiscible with a second fluid is flowed into the second fluid. With reference to FIG. 12, a first (e.g., aqueous) fluid comprising a monomer, crosslinker, initiator, and aqueous surfactant 1201 is flowed into a second (e.g., oil) fluid comprising a surfactant and an accelerator 1202. After entering the second fluid at a T-junction in a microfluidic device 1203, a droplet of first fluid breaks off from the first fluid stream and a capsule shell begins to form 1204 due to the mixing of the monomer, crosslinker, and initiator in the first fluid and the accelerator in the second fluid. Thus, a capsule is formed. As the capsule proceeds downstream, the shell becomes thicker due to increased exposure to the accelerator. Varying the concentrations of the reagents may also be used to vary the thickness and permeability of the capsule shell.

A species, or other partition such as a droplet, may be encapsulated by, for example, including the species in the first fluid. Including the species in the second fluid may embed the species in the shell of the capsule. Of course, depending on the needs of the particular sample processing method, the phases may also be reversed—i.e., the first phase may be an oil phase and the second phase may be an aqueous phase.

2. Production of Capsules within Capsules by Flow Focusing

Figure 13:
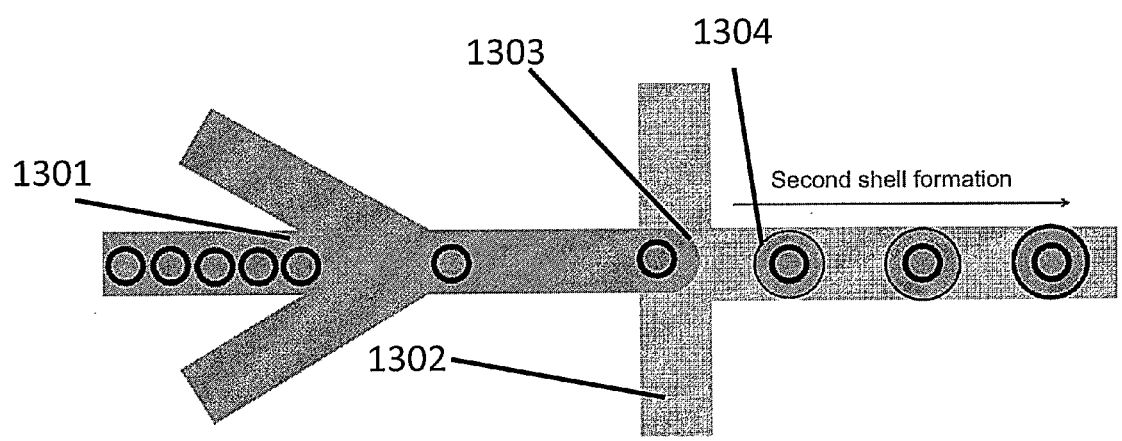
FIG. 13 schematically depicts the production of capsules within capsules via an example flow-focusing method.

In some cases, capsules within capsules may be produced by flow focusing. With reference to FIG. 13, a first (e.g., aqueous) fluid comprising a capsule, monomer, crosslinker, initiator, and aqueous surfactant 1301 is flowed into a second (oil) fluid comprising a surfactant and an accelerator 1302. After entering the second fluid at a T-junction in a microfluidic device 1303, a droplet of first fluid breaks off from the first fluid stream and a second capsule shell begins to form around the capsule 1304 due to the mixing of the monomer, crosslinker, and initiator in the first fluid and the accelerator in the second fluid. Thus, a capsule within a capsule is formed. As the capsule proceeds downstream, the shell becomes thicker due to increased exposure to the accelerator. Varying the concentrations of the reagents may also be used to vary the thickness and permeability of the second capsule shell.

A species may be encapsulated by, for example, including the species in the first fluid. Including the species in the second fluid may embed the species in the second shell of the capsule. Of course, depending on the needs of the particular sample processing method, the phases may also be reversed—i.e., the first phase may be an oil phase and the second phase may be an aqueous phase.

3. Production of Capsules in Batch

In some cases, capsules may be produced in batch, using capsule precursors, such as the droplets in an emulsion. Capsule precursors may be formed by any suitable method, for example by producing an emulsion with droplets comprising a monomer, a crosslinker, an initiator, and a surfactant. An accelerator may then be added to the medium, resulting in the formation of capsules. As for the methods of flow focusing, the thickness of the shell can be varied by varying the concentrations of the reactants, and the time of exposure to the accelerator. The capsules may then be washed and recovered. As for any method described herein, a species, including other partitions, may be encapsulated within the capsule or, if suitable, within the shell.

In another example, the droplets of an emulsion may be exposed to an accelerator that is present in an outlet well during the emulsion generation process. For example, capsule precursors may be formed by any suitable method, such as the flow focusing method illustrated in FIG. 12. Rather than including the accelerator in second fluid 1202, the accelerator may be included in a medium located at the exit of the T-junction (e.g., a medium located at the far-right of the horizontal channel of FIG. 12. As the emulsion droplets (i.e., capsule precursors) exit the channel, they contact the medium comprising the accelerator (i.e., the outlet medium). If the capsule precursor has a density that is less than the density of outlet medium, the capsule precursors will rise through the medium, ensuring convectional and diffusional exposure to the accelerator and reducing the likelihood of polymerization at the outlet of the channel.

VI. SPECIES

The methods, compositions, systems, devices, and kits of this disclosure may be used with any suitable species. A species can be, for example, any substance used in sample processing, such as a reagent or an analyte. Exemplary species include whole cells, chromosomes, polynucleotides, organic molecules, proteins, polypeptides, carbohydrates, saccharides, sugars, lipids, enzymes, restriction enzymes, ligases, polymerases, barcodes, adapters, small molecules, antibodies, fluorophores, deoxynucleotide triphosphates (dNTPs), dideoxynucleotide triphosphates (ddNTPs), buffers, acidic solutions, basic solutions, temperature-sensitive enzymes, pH-sensitive enzymes, light-sensitive enzymes, metals, metal ions, magnesium chloride, sodium chloride, manganese, aqueous buffer, mild buffer, ionic buffer, inhibitors, saccharides, oils, salts, ions, detergents, ionic detergents, non-ionic detergents, oligonucleotides, nucleotides, DNA, RNA, peptide polynucleotides, complementary DNA (cDNA), double stranded DNA (dsDNA), single stranded DNA (ssDNA), plasmid DNA, cosmid DNA, chromosomal DNA, genomic DNA, viral DNA, bacterial DNA, mtDNA (mitochondrial DNA), mRNA, rRNA, tRNA, nRNA, siRNA, snRNA, snoRNA, scaRNA, microRNA, dsRNA, ribozyme, riboswitch and viral RNA, a locked nucleic acid (LNA) in whole or part, locked nucleic acid nucleotides, any other type of nucleic acid analogue, proteases, nucleases, protease inhibitors, nuclease inhibitors, chelating agents, reducing agents, oxidizing agents, probes, chromophores, dyes, organics, emulsifiers, surfactants, stabilizers, polymers, water, small molecules, pharmaceuticals, radioactive molecules, preservatives, antibiotics, aptamers, and the like. In summary, the species that are used will vary depending on the particular sample processing needs.

In some cases, a partition comprises a set of species that have a similar attribute (e.g., a set of enzymes, a set of minerals, a set of oligonucleotides, a mixture of different barcodes, a mixture of identical barcodes). In other cases, a partition comprises a heterogeneous mixture of species. In some cases, the heterogeneous mixture of species comprises all components necessary to perform a particular reaction. In some cases, such mixture comprises all components necessary to perform a reaction, except for 1, 2, 3, 4, 5, or more components necessary to perform the reaction. In some cases, such additional components are contained within a different partition or within a solution within or surrounding a partition.

A species may be naturally-occurring or synthetic. A species may be present in a sample obtained using any methods known in the art. In some cases, a sample may be processed before analyzing it for an analyte.

A species may be obtained from any suitable location, including from organisms, whole cells, cell preparations and cell-free compositions from any organism, tissue, cell, or environment. A species may be obtained from environmental samples, biopsies, aspirates, formalin fixed embedded tissues, air, agricultural samples, soil samples, petroleum samples, water samples, or dust samples. In some instances, a species may be obtained from bodily fluids which may include blood, urine, feces, serum, lymph, saliva, mucosal secretions, perspiration, central nervous system fluid, vaginal fluid, or semen. Species may also be obtained from manufactured products, such as cosmetics, foods, personal care products, and the like. Species may be the products of experimental manipulation including, recombinant cloning, polynucleotide amplification, polymerase chain reaction (PCR) amplification, purification methods (such as purification of genomic DNA or RNA), and synthesis reactions.

In some cases, a species may quantified by mass. A species may be provided in a mass of about 1, 2, 3, 4, 5, 6, 7, 8, 9, 10, 11, 12, 13, 14, 15, 16, 17, 18, 19, 20, 50, 100, 500, 1000, 1500, 2000, 2500, 3000, 3500, 4000, 4500, 5000, 5500, 6000, 6500, 7000, 7500, 8000, 8500, 9000, 9500, 10000 ng, 1 µg, 5 µg, 10

µg, 15 µg, or 20 µg. A species may be provided in a mass of at least about 1, 2, 3, 4, 5, 6, 7, 8, 9, 10, 11, 12, 13, 14, 15, 16, 17, 18, 19, 20, 50, 100, 500, 1000, 1500, 2000, 2500, 3000, 3500, 4000, 4500, 5000, 5500, 6000, 6500, 7000, 7500, 8000, 8500, 9000, 9500, 10000 ng, 1 µg, 5 µg, 10 µg, 15 µg, or 20 µg. A species may be provided in a mass of less than about 2, 3, 4, 5, 6, 7, 8, 9, 10, 11, 12, 13, 14, 15, 16, 17, 18, 19, 20, 50, 100, 500, 1000, 1500, 2000, 2500, 3000, 3500, 4000, 4500, 5000, 5500, 6000, 6500, 7000, 7500, 8000, 8500, 9000, 9500, 10000 ng 1 µg, 5 µg, 10 µg, 15 µg, or 20 µg. A species may be provided in a mass ranging from about 1-10, 10-50, 50-100, 100-200, 200-1000, 1000-10000 ng, 1-5 µg, or 1-20 µg. As described elsewhere in this disclosure, if a species is a polynucleotide, amplification may be used to increase the quantity of a polynucleotide.

Polynucleotides may also be quantified as "genome equivalents." A genome equivalent is an amount of polynucleotide equivalent to one haploid genome of an organism from which the target polynucleotide is derived. For example, a single diploid cell contains two genome equivalents of DNA. Polynucleotides may be provided in an amount ranging from about 1-10, 10-50, 50-100, 100-1000, 1000-10000, 10000-100000, or 100000-1000000 genome equivalents. Polynucleotides may be provided in an amount of at least about 1, 2, 3, 4, 5, 6, 7, 8, 9, 10, 11, 12, 13, 14, 15, 16, 17, 18, 19, 20, 50, 100, 500, 1000, 1500, 2000, 2500, 3000, 3500, 4000, 4500, 5000, 5500, 6000, 6500, 7000, 7500, 8000, 8500, 9000, 9500, 10000, 20000, 30000, 40000, 50000, 60000 70000, 80000, 90000, 100000, 200000, 300000, 400000, 500000, 600000, 700000, 800000, 900000, or 1000000 genome equivalents. Polynucleotides may be provided in an amount less than about 2, 3, 4, 5, 6, 7, 8, 9, 10, 11, 12, 13, 14, 15, 16, 17, 18, 19, 20, 50, 100, 500, 1000, 1500, 2000, 2500, 3000, 3500, 4000, 4500, 5000, 5500, 6000, 6500, 7000, 7500, 8000, 8500, 9000, 9500, 10000, 20000, 30000, 40000, 50000, 60000 70000, 80000, 90000, 100000, 200000, 300000, 400000, 500000, 600000, 700000, 800000, 900000, or 1000000 genome equivalents.

Polynucleotides may also be quantified by the amount of sequence coverage provided. The amount of sequence coverage refers to the average number of reads representing a given nucleotide in a reconstructed sequence. Generally, the greater the number of times a region is sequenced, the more accurate the sequence information obtained. Polynucleotides may be provided in an amount that provides a range of sequence coverage from about 0.1×-10×, 10×-50×, 50×-100×, 100×-200×, or 200×-500×. Polynucleotides may be provided in an amount that provides at least about 0.1×, 0.2×, 0.3×, 0.4×, 0.5×, 0.6×, 0.7×, 0.8×, 0.9×, 1.0×, 5×, 10×, 25×, 50×, 100×, 125×, 150×, 175×, or 200× sequence coverage. Polynucleotides may be provided in an amount that provides less than about 0.2×, 0.3×, 0.4×, 0.5×, 0.6×, 0.7×, 0.8×, 0.9×, 1.0×, 5×, 10×, 25×, 50×, 100×, 125×, 150×, 175×, or 200× sequence coverage.

In some cases, species are introduced into a partition either before or after a particular step. For example, a lysis buffer reagent may be introduced into a partition following partitioning of a cellular sample into the partitions. In some cases, reagents and/or partitions comprising reagents are introduced sequentially such that different reactions or operations occur at different steps. The reagents (or partitions comprising reagents) may be also be loaded at steps interspersed with a reaction or operation step. For example, capsules comprising reagents for fragmenting molecules (e.g., nucleic acids) may be loaded into a well, followed by a fragmentation step, which may be followed by loading of capsules comprising reagents for ligating barcodes (or other unique identifiers, e.g., antibodies) and subsequent ligation of the barcodes to the fragmented molecules.

VII. PROCESSING OF ANALYTES AND OTHER SPECIES

In some cases, the methods, compositions, systems, devices, and kits of this disclosure may be used to process a sample containing a species, for example an analyte. Any suitable process can be performed.

a. Fragmentation of Target Polynucleotides

In some cases, the methods, compositions, systems, devices, and kits of this disclosure may be used for polynucleotide fragmentation. Fragmentation of polynucleotides is used as a step in a variety of methods, including polynucleotide sequencing. The size of the polynucleotide fragments, typically described in terms of length (quantified by the linear number of nucleotides per fragment), may vary depending on the source of the target polynucleotide, the method used for fragmentation, and the desired application. A single fragmentation step or a plurality of fragmentation steps may be used.

Fragments generated using the methods described herein may be about 1-10, 10-20, 20-50, 50-100, 50-200, 100-200, 200-300, 300-400, 400-500, 500-1000, 1000-5000, 5000-10000, 10000-100000, 100000-250000, or 250000-500000 nucleotides in length. Fragments generated using the methods described herein may be at least about 10, 20, 100, 200, 300, 400, 500, 1000, 5000, 10000, 100000, 250000, 500000, or more nucleotides in length. Fragments generated using the methods described herein may be less than about 10, 20, 100, 200, 300, 400, 500, 1000, 5000, 10000, 100000, 250000, 500000, nucleotides in length.

Fragments generated using the methods described herein may have a mean or median length of about 1-10, 10-20, 20-50, 50-100, 50-200, 100-200, 200-300, 300-400, 400-500, 500-1000, 1000-5000, 5000-10000, 10000-100000, 100000-250000, or 250000-500000 nucleotides.

Fragments generated using the methods described herein may have a mean or median length of at least about 10, 20, 100, 200, 300, 400, 500, 1000, 5000, 10000, 100000, 250000, 500000, or more nucleotides. Fragments generated using the methods described herein may have a mean or median length of less than about 10, 20, 100, 200, 300, 400, 500, 1000, 5000, 10000, 100000, 250000, 500000, nucleotides.

Numerous fragmentation methods are known in the art. For example, fragmentation may be performed through physical, mechanical or enzymatic methods. Physical fragmentation may include exposing a target polynucleotide to heat or to UV light. Mechanical disruption may be used to mechanically shear a target polynucleotide into fragments of the desired range. Mechanical shearing may be accomplished through a number of methods known in the art, including repetitive pipetting of the target polynucleotide, sonication (e.g., using ultrasonic waves), cavitation and nebulization. Target polynucleotides may also be fragmented using enzymatic methods. In some cases, enzymatic digestion may be performed using enzymes such as using restriction enzymes.

While the methods of fragmentation described in the preceding paragraph, and in some paragraphs of the disclosure, are described with reference to "target" polynucleotides, this is not meant to be limiting, above or anywhere else in this disclosure. Any method of fragmentation described herein, or known in the art, can be applied to any polynucleotide used with the invention. In some cases, this polynucleotide may be a target polynucleotide, such as a genome.

In other cases, this polynucleotide may be a fragment of a target polynucleotide which one wishes to further fragment. In still other cases, still further fragments may be still further fragmented. Any suitable polynucleotide may be fragmented according to the methods described herein.

Restriction enzymes may be used to perform specific or non-specific fragmentation of target polynucleotides. The methods of the present disclosure may use one or more types of restriction enzymes, generally described as Type I enzymes, Type II enzymes, and/or Type III enzymes. Type II and Type III enzymes are generally commercially available and well known in the art. Type II and Type III enzymes recognize specific sequences of nucleotide base pairs within a double stranded polynucleotide sequence (a "recognition sequence" or "recognition site"). Upon binding and recognition of these sequences, Type II and Type III enzymes cleave the polynucleotide sequence. In some cases, cleavage will result in a polynucleotide fragment with a portion of overhanging single stranded DNA, called a "sticky end." In other cases, cleavage will not result in a fragment with an overhang, creating a "blunt end." The methods of the present disclosure may comprise use of restriction enzymes that generate either sticky ends or blunt ends.

Restriction enzymes may recognize a variety of recognition sites in the target polynucleotide. Some restriction enzymes ("exact cutters") recognize only a single recognition site (e.g., GAATTC). Other restriction enzymes are more promiscuous, and recognize more than one recognition site, or a variety of recognition sites. Some enzymes cut at a single position within the recognition site, while others may cut at multiple positions. Some enzymes cut at the same position within the recognition site, while others cut at variable positions.

The present disclosure provides method of selecting one or more restriction enzymes to produce fragments of a desired length. Polynucleotide fragmentation may be simulated in silico, and the fragmentation may be optimized to obtain the greatest number or fraction of polynucleotide fragments within a particular size range, while minimizing the number or fraction of fragments within undesirable size ranges. Optimization algorithms may be applied to select a combination of two or more enzymes to produce the desired fragment sizes with the desired distribution of fragments quantities.

A polynucleotide may be exposed to two or more restriction enzymes simultaneously or sequentially. This may be accomplished by, for example, adding more than one restriction enzyme to a partition, or by adding one restriction enzyme to a partition, performing the digestion, deactivating the restriction enzyme (e.g., by heat treatment) and then adding a second restriction enzyme. Any suitable restriction enzyme may be used alone, or in combination, in the methods presented herein.

In some cases, a species is a restriction enzyme that is a "rare-cutter." The term "rare-cutter enzyme," as used herein, generally refers to an enzyme with a recognition site that occurs only rarely in a genome. The size of restriction fragments generated by cutting a hypothetical random genome with a restriction enzyme may be approximated by $4^N$, where N is the number of nucleotides in the recognition site of the enzyme. For example, an enzyme with a recognition site consisting of 7 nucleotides would cut a genome once every $4^7$ bp, producing fragments of about 16,384 bp. Generally rare-cutter enzymes have recognition sites comprising 6 or more nucleotides. For example, a rare cutter enzyme may have a recognition site comprising or consisting of 6, 7, 8, 9, 10, 11, 12, 13, 14, or 15 nucleotides. Examples of rare-cutter enzymes include NotI (GCGGCCGC), XmaIII (CGGCCG), SstII (CCGCGG), SalI (GTCGAC), NruI (TCGCGA), NheI (GCTAGC), Nb.BbvCI (CCTCAGC), BbvCI (CCTCAGC), AscI (GGCGCGCC), AsiSI (GCGATCGC), FseI (GGCCGGCC), PacI (TTAATTAA), PmeI (GTTTAAAC), SbfI (CCTGCAGG), SgrAI (CRCCGGYG), SwaI (ATTTAAAT), BspQI (GCTCTTC), SapI (GCTCTTC), SfiI (GGCCNNNNNGGCC) (SEQ ID NO: 27), CspCI (CAANNNNNGTGG) (SEQ ID NO: 28), AbsI (CCTCGAGG), CciNI (GCGGCCGC), FspAI (RTGCGCAY), MauBI (CGCGCGCG), MreI (CGCCGGCG), MssI (GTTTAAAC), PalAI (GGCGCGCC), RgaI (GCGATCGC), RigI (GGCCGGCC), SdaI (CCTGCAGG), SfaAI (GCGATCGC), SgfI (GCGATCGC), SgrDI (CGTCGACG), SgsI (GGCGCGCC), SmiI (ATTTAAAT), SrfI (GCCCGGGC), Sse2321 (CGCCGGCG), Sse83871 (CCTGCAGG), LguI (GCTCTTC), PciSI (GCTCTTC), AarI (CACCTGC), AjuI (GAANNNNNNNTTGG) (SEQ ID NO: 29), AloI (GAACNNNNNNTCC) (SEQ ID NO: 30), BarI (GAAGNNNNNNTAC) (SEQ ID NO: 31), PpiI (GAACNNNNNCTC) (SEQ ID NO: 32), PsrI (GAACNNNNNNTAC) (SEQ ID NO: 33), and others.

In some cases, polynucleotides may be fragmented and barcoded at the same time. For example, a transposase (e.g., NEXTERA) may be used to fragment a polynucleotide and add a barcode to the polynucleotide.

VIII. STIMULI-RESPONSIVENESS

In some cases, stimuli may be used to trigger the release of a species from a partition. Generally, a stimulus may cause disruption of the structure of a partition, such as the wall of a well, a component of a spot, the stability of a droplet (e.g., a droplet in an emulsion), or the shell of a capsule. These stimuli are particularly useful in inducing a partition to release its contents. Because a partition may be contained within another partition, and each partition may be responsive (or not responsive) to different stimuli, stimuli-responsiveness may be employed to release the contents of one partition (e.g., a partition responsive to the stimulus) into another partition (e.g., a partition not responsive to that stimulus, or less responsive to that stimulus).

In some cases, the contents of an inner capsule may be released into the contents of an outer capsule by applying a stimulus that dissolves the inner capsule, resulting in a capsule containing a mixed sample. Of course, this embodiment is purely illustrative, and stimuli-responsiveness may be used to release the contents of any suitable partition into any other suitable partition, medium, or container (see, e.g., Table 1 for more specific examples of partitions within partitions).

Examples of stimuli that may be used include chemical stimuli, bulk changes, biological stimuli, light, thermal stimuli, magnetic stimuli, addition of a medium to a well, and any combination thereof, as described more fully below. (See, e.g., Esser-Kahn et al., (2011) *Macromolecules* 44: 5539-5553; Wang et al., (2009) *ChemPhysChem* 10:2405-2409.)

a. Chemical Stimuli and Bulk Changes

Numerous chemical triggers may be used to trigger the disruption of partitions (e.g., Plunkett et al., Biomacromolecules, 2005, 6:632-637). Examples of these chemical changes may include, but are not limited to pH-mediated changes to the integrity of a component of a partition, disintegration of a component of a partition via chemical cleavage of crosslink bonds, and triggered depolymerization of a component of a partition. Bulk changes may also be used to trigger disruption of partitions.

A change in pH of a solution, such as a decrease in pH, may trigger disruption of a partition via a number of different mechanisms. The addition of acid may cause degradation or disassembly a portion of a partition through a variety of mechanisms. Addition of protons may disassemble cross-linking of polymers in a component of a partition, disrupt ionic or hydrogen bonds in a component of a partition, or create nanopores in a component of a partition to allow the inner contents to leak through to the exterior. A change in pH may also destabilize an emulsion, leading to release of the contents of the droplets.

In some examples, a partition is produced from materials that comprise acid-degradable chemical cross-linkers, such a ketals. A decrease in pH, particular to a pH lower than 5, may induce the ketal to convert to a ketone and two alcohols and facilitate disruption of the partition. In other examples, the partitions may be produced from materials comprising one or more polyelectrolytes that are pH sensitive. A decrease in pH may disrupt the ionic- or hydrogen-bonding interactions of such partitions, or create nanopores therein. In some cases, partitions made from materials comprising polyelectrolytes comprise a charged, gel-based core that expands and contracts upon a change of pH.

Disruption of cross-linked materials comprising a partition can be accomplished through a number of mechanisms. In some examples, a partition can be contacted with various chemicals that induce oxidation, reduction or other chemical changes. In some cases, a reducing agent, such as beta-mercaptoethanol, can be used, such that disulfide bonds of a partition are disrupted. In addition, enzymes may be added to cleave peptide bonds in materials forming a partition, thereby resulting in a loss of integrity of the partition.

Depolymerization can also be used to disrupt partitions. A chemical trigger may be added to facilitate the removal of a protecting head group. For example, the trigger may cause removal of a head group of a carbonate ester or carbamate within a polymer, which in turn causes depolymerization and release of species from the inside of a partition.

In yet another example, a chemical trigger may comprise an osmotic trigger, whereby a change in ion or solute concentration in a solution induces swelling of a material used to make a partition. Swelling may cause a buildup of internal pressure such that a partition ruptures to release its contents. Swelling may also cause an increase in the pore size of the material, allowing species contained within the partition to diffuse out, and vice versa.

A partition may also be made to release its contents via bulk or physical changes, such as pressure induced rupture, melting, or changes in porosity.

b. Biological Stimuli

Biological stimuli may also be used to trigger disruption of partitions. Generally, biological triggers resemble chemical triggers, but many examples use biomolecules, or molecules commonly found in living systems such as enzymes, peptides, saccharides, fatty acids, nucleic acids and the like. For example, partitions may be made from materials comprising polymers with peptide cross-links that are sensitive to cleavage by specific proteases. More specifically, one example may comprise a partition made from materials comprising GFLGK (SEQ ID NO: 34) peptide cross links. Upon addition of a biological trigger such as the protease Cathepsin B, the peptide cross links of the shell well are cleaved and the contents of the capsule are released. In other cases, the proteases may be heat-activated. In another example, partitions comprise a component comprising cellulose. Addition of the hydrolytic enzyme chitosan serves as biologic trigger for cleavage of cellulosic bonds, depolymerization of component of the partition comprising chitosan, and release of its inner contents.

c. Thermal Stimuli

Partitions may also be induced to release their contents upon the application of a thermal stimulus. A change in temperature can cause a variety changes to a partition. A change in heat may cause melting of a partition such that a portion of the partition disintegrates, or disruption of an emulsion. In other cases, heat may increase the internal pressure of the inner components of a partition such that the partition ruptures or explodes. In still other cases, heat may transform a partition into a shrunken dehydrated state. Heat may also act upon heat-sensitive polymers used as materials to construct partitions.

In one example, a partition is made from materials comprising a thermo-sensitive hydrogel. Upon the application of heat, such as a temperature above 35 C, the hydrogel material shrinks. The sudden shrinkage of the material increases the pressure and ruptures the partition.

In some cases, a material used to produce a partition may comprise a diblock polymer, or a mixture of two polymers, with different heat sensitivities. One polymer may be particularly likely to shrink after the application of heat, while the other is more heat-stable. When heat is applied to such shell wall, the heat-sensitive polymer may shrink, while the other remains intact, causing a pore to form. In still other cases, a material used to produce a partition may comprise magnetic nanoparticles. Exposure to a magnetic field may cause the generation of heat, leading to rupture of the partition.

d. Magnetic Stimuli

Inclusion of magnetic nanoparticles in a material used to produce a partition may allow triggered rupture of the partition, as described above, as well as enable guidance of these partitions to other partitions (e.g., guidance of capsules to wells in an array). In one example, incorporation of $Fe_3O_4$ nanoparticles into materials used to produce partitions triggers rupture in the presence of an oscillating magnetic field stimulus.

e. Electrical and Light Stimuli

A partition may also be disrupted as the result of electrical stimulation. Similar to the magnetic particles described in the previous section, electrically sensitive particles can allow for both triggered rupture of partitions, as well as other functions such as alignment in an electric field or redox reactions. In one example, partitions made from materials comprising electrically sensitive material are aligned in an electric field such that release of inner reagents can be controlled. In other examples, electric fields may induce redox reactions within a partition that may increase porosity.

A light stimulus may also be used to disrupt the partitions. Numerous light triggers are possible and may include systems that use various molecules such as nanoparticles and chromophores capable of absorbing photons of specific ranges of wavelengths. For example, metal oxide coatings can be used to produce certain partitions. UV irradiation of partitions coated with SiO2/TiO2 may result in disintegration of the partition wall. In yet another example, photo switchable materials such as azobenzene groups may be incorporated in the materials used to produce the partitions. Upon the application of UV or visible light, chemicals such as these undergo a reversible cis-to-trans isomerization upon absorption of photons. In this aspect, incorporation of photo switches results in disintegration of a portion of a partition, or an increase in porosity of a portion of a partition.

f. Application of Stimuli

The devices, methods, compositions, systems, and kits of this disclosure may be used in combination with any apparatus or device that provides such trigger or stimulus. For example, if the stimulus is thermal, a device may be used in combination with a heated or thermally controlled plate, which allows heating of the wells and may induce the rupture of capsules. Any of a number of methods of heat transfer may be used for thermal stimuli, including but not limited to applying heat by radiative heat transfer, convective heat transfer, or conductive heat transfer. In other cases, if the stimulus is a biological enzyme, the enzyme may be injected into a device such that it is deposited into each well. In another aspect, if the stimulus is a magnetic or electric field, a device may be used in combination with a magnetic or electric plate.

IX. APPLICATIONS a. Polynucleotide Sequencing

Generally, the methods and compositions provided herein are useful for preparation of polynucleotide fragments for downstream applications such as sequencing. Sequencing may be performed by any available technique. For example, sequencing may be performed by the classic Sanger sequencing method. Sequencing methods may also include: high-throughput sequencing, pyrosequencing, sequencing-by-synthesis, single-molecule sequencing, nanopore sequencing, sequencing-by-ligation, sequencing-by-hybridization, RNA-Seq (Illumina), Digital Gene Expression (Helicos), next generation sequencing, single molecule sequencing by synthesis (SMSS) (Helicos), massively-parallel sequencing, clonal single molecule Array (Solexa), shotgun sequencing, Maxim-Gilbert sequencing, primer walking, and any other sequencing methods known in the art.

In some cases varying numbers of fragments are sequenced. For example, in some cases about 30%-90% of the fragments are sequenced. In some cases, about 35%-85%, 40%-80%, 45%-75%, 50%-70%, 55%-65%, or 50%-60% of the fragments are sequenced. In some cases, at least about 30%, 40%, 50%, 60%, 70%, 80%, or 90% of the fragments are sequenced. In some cases less than about 30%, 40%, 50%, 60%, 70%, 80%, or 90% of the fragments are sequenced.

In some cases sequences from fragments are assembled to provide sequence information for a contiguous region of the original target polynucleotide that is longer than the individual sequence reads. Individual sequence reads may be about 10-50, 50-100, 100-200, 200-300, 300-400, or more nucleotides in length.

The identities of the barcode tags may serve to order the sequence reads from individual fragments as well as to differentiate between haplotypes. For example, during the partitioning of individual fragments, parental polynucleotide fragments may separated into different partitions. With an increase in the number of partitions, the likelihood of a fragment from both a maternal and paternal haplotype contained in the same partition becomes negligibly small. Thus, sequence reads from fragments in the same partition may be assembled and ordered.

b. Polynucleotide Phasing

This disclosure also provides methods and compositions to prepare polynucleotide fragments in such a manner that may enable phasing or linkage information to be generated. Such information may allow for the detection of linked genetic variations in sequences, including genetic variations (e.g., SNPs, mutations, indels, copy number variations, transversions, translocations, inversions, etc.) that are separated by long stretches of polynucleotides. The term "indel" refers to a mutation resulting in a colocalized insertion and deletion and a net gain or loss in nucleotides. A "microindel" is an indel that results in a net gain or loss of 1 to 50 nucleotides. These variations may exist in either a cis or trans relationship. In a cis relationship, two or more genetic variations exist in the same polynucleotide or strand. In a trans relationship, two or more genetic variations exist on multiple polynucleotide molecules or strands.

Methods provided herein may be used to determine polynucleotide phasing. For example, a polynucleotide sample (e.g., a polynucleotide that spans a given locus or loci) may be partitioned such that at most one molecule of polynucleotide is present per partition. The polynucleotide may then be fragmented, barcoded, and sequenced. The sequences may be examined for genetic variation. The detection of genetic variations in the same sequence tagged with two different bar codes may indicate that the two genetic variations are derived from two separate strands of DNA, reflecting a trans relationship. Conversely, the detection of two different genetic variations tagged with the same bar codes may indicate that the two genetic variations are from the same strand of DNA, reflecting a cis relationship.

Phase information may be important for the characterization of a polynucleotide fragment, particularly if the polynucleotide fragment is derived from a subject at risk of, having, or suspected of a having a particular disease or disorder (e.g., hereditary recessive disease such as cystic fibrosis, cancer, etc.). The information may be able to distinguish between the following possibilities: (1) two genetic variations within the same gene on the same strand of DNA and (2) two genetic variations within the same gene but located on separate strands of DNA. Possibility (1) may indicate that one copy of the gene is normal and the individual is free of the disease, while possibility (2) may indicate that the individual has or will develop the disease, particularly if the two genetic variations are damaging to the function of the gene when present within the same gene copy. Similarly, the phasing information may also be able to distinguish between the following possibilities: (1) two genetic variations, each within a different gene on the same strand of DNA and (2) two genetic variations, each within a different gene but located on separate strands of DNA.

c. Sequencing Polynucleotides from Small Numbers of Cells

Methods provided herein may also be used to prepare polynucleotides contained within cells in a manner that enables cell-specific information to be obtained. The methods enable detection of genetic variations (e.g., SNPs, mutations, indels, copy number variations, transversions, translocations, inversions, etc.) from very small samples, such as from samples comprising about 10-100 cells. In some cases, about 1, 5, 10, 20, 30, 40, 50, 60, 70, 80, 90 or 100 cells may be used in the methods described herein. In some cases, at least about 1, 5, 10, 20, 30, 40, 50, 60, 70, 80, 90 or 100 cells may be used in the methods described herein. In other cases, at most about 5, 10, 20, 30, 40, 50, 60, 70, 80, 90 or 100 cells may be used in the methods described herein.

In an example, a method comprises partitioning a cellular sample (or crude cell extract) such that at most one cell (or extract of one cell) is present per partition, lysing the cells, fragmenting the polynucleotides contained within the cells by any of the methods described herein, attaching the fragmented polynucleotides to barcodes, pooling, and sequencing.

As described elsewhere herein, the barcodes and other reagents may be contained within a partition (e.g., a capsule). These capsules may be loaded into another partition (e.g., a well) before, after, or concurrently with the loading of the cell, such that each cell is contacted with a different capsule. This technique may be used to attach a unique barcode to polynucleotides obtained from each cell. The resulting tagged polynucleotides may then be pooled and sequenced, and the barcodes may be used to trace the origin of the polynucleotides. For example, polynucleotides with identical barcodes may be determined to originate from the same cell, while polynucleotides with different barcodes may be determined to originate from different cells.

The methods described herein may be used to detect the distribution of oncogenic mutations across a population of cancerous tumor cells. For example, some tumor cells may have a mutation, or amplification, of an oncogene (e.g., HER2, BRAF, EGFR, KRAS) in both alleles (homozygous), others may have a mutation in one allele (heterozygous), and still others may have no mutation (wild-type). The methods described herein may be used to detect these differences, and also to quantify the relative numbers of homozygous, heterozygous, and wild-type cells. Such information may be used, for example, to stage a particular cancer and/or to monitor the progression of the cancer and its treatment over time.

In some examples, this disclosure provides methods of identifying mutations in two different oncogenes (e.g., KRAS and EGFR). If the same cell comprises genes with both mutations, this may indicate a more aggressive form of cancer. In contrast, if the mutations are located in two different cells, this may indicate that the cancer is more benign, or less advanced.

d. Analysis of Gene Expression

Methods of the disclosure may be applicable to processing samples for the detection of changes in gene expression. A sample may comprise a cell, mRNA, or cDNA reverse transcribed from mRNA. The sample may be a pooled sample, comprising extracts from several different cells or tissues, or a sample comprising extracts from a single cell or tissue.

Cells may be placed directly into a partition (e.g., a microwell) and lysed. After lysis, the methods of the invention may be used to fragment and barcode the polynucleotides of the cell for sequencing. Polynucleotides may also be extracted from cells prior to introducing them into a partition used in a method of the invention. Reverse transcription of mRNA may be performed in a partition described herein, or outside of such a partition. Sequencing cDNA may provide an indication of the abundance of a particular transcript in a particular cell over time, or after exposure to a particular condition.

The methods presented above provide several advantages over current polynucleotide processing methods. First, inter-operator variability is greatly reduced. Second, the methods may be carried out in microfluidic devices, which have a low cost and can be easily fabricated. Third, the controlled fragmentation of the target polynucleotides allows the user to produce polynucleotide fragments with a defined and appropriate length. This aids in partitioning the polynucleotides and also reduces the amount of sequence information loss due to the present of overly-large fragments. The methods and systems also provide a facile workflow that maintains the integrity of the processed polynucleotide. Additionally, the use of restriction enzymes enables the user to create DNA overhangs ("sticky ends") that may be designed for compatibility with adapters and/or barcodes.

e. Partitioning of Polynucleotides, Such as Chromosomes, from Cells

In one example the methods, compositions, systems, devices, and kits provided in this disclosure may be used to partition polynucleotides, including whole chromosomes, from cells. In one example, a single cell or a plurality of cells (e.g., 2, 10, 50, 100, 1000, 10000, 25000, 50000, 100000, 500000, 1000000, or more cells) is loaded into a vessel with lysis buffer and proteinase K, and incubated for a specified period of time. Utilization of a plurality of cells will enable polynucleotide phasing, for example, by partitioning each polynucleotide to be analyzed in its own partition.

After incubation, the cell lysate is partitioned, for example by flow focusing the cell lysate into a capsule. If phasing is to be performed, flow focusing is performed such that each capsule comprises only a single analyte (e.g., a single chromosome), or only a single copy of any particular chromosome (e.g., one copy of a first chromosome and one copy of a second chromosome). In some cases, a plurality of chromosomes may be encapsulated within the same capsule, so long as the chromosomes are not the same chromosome. The encapsulation is performed under gentle flow, to minimize shearing of the polynucleotides. The capsule may be porous, to allow washing of the contents of the capsule, and introduction of reagents into the capsule, while maintaining the polynucleotides (e.g., chromosomes) within the capsules. The encapsulated polynucleotides (e.g., chromosomes) may then be processed according to any of the methods provided in this disclosure, or known in the art. The capsule shells protect the encapsulated polynucleotides (e.g., chromosomes) from shearing and further degradation. Of course, this method can also be applied to any other cellular component.

As described above, the capsule shell may be used to protect a polynucleotide from shearing. However, a capsule may also be used as a partition to enable compartmentalized shearing of a polynucleotide or other analyte. For example, in some cases a polynucleotide may be encapsulated within a capsule and then subject to ultrasonic shear, or any other suitable shearing. The capsule shell may be configured to remain intact under the shear, while the encapsulated polynucleotide may be sheared, but will remain within the capsule. In some cases, a hydrogel droplet may be used to accomplish the same end.

f. Cancer Mutation Detection and Forensics

Barcoding methods via amplification-based barcoding schemes in partitions described herein may be useful generating barcode libraries from degraded samples such as, for example, fixed formalin-fixed, paraffin-embedded (FFPE) tissue sections. Methods described herein may be capable of identifying that all amplicons within a partition originated from the same initial molecule. Indeed, with partition barcoding, information can be retained about a unique starting polynucleotide. Such identification may aid in determinations of library complexity as amplicons from different original molecules can be distinguished. Moreover, methods described herein can permit assessing unique coverage which may aid in determining variant calling sensitivity. These advantages may be particularly useful in cancer mutation detection and forensics.

g. Low Input DNA Applications (Circulating Tumor Cell (CTC) Sequencing)

Barcoding methods described herein may be useful in low polynucleotide input applications, such as, for example the sequencing of nucleic acids of circulating tumor cells (CTCs). For example, MALBAC methods described herein within a partition may aid in obtaining good data quality in low polynucleotide input applications and/or aid in filtering out amplification errors.

VIII. KITS

In some cases, this disclosure provides kits comprising reagents for the generation of partitions. The kit may comprise any suitable reagents and instructions for the generation of partitions and partitions within partitions.

In one example, a kit comprises reagents for generating capsules within droplets in an emulsion. For example, a kit may comprise reagents for generating capsules, reagents for generating an emulsion, and instructions for introducing the capsules into the droplets of the emulsion. As specified throughout this disclosure, any suitable species may be incorporated into the droplets and/or into the capsule. A kit of this disclosure may also provide any of these species, such as a polynucleotide comprising a barcode that is pre-partitioned. Similarly, as described throughout the disclosure, the capsule may be designed to release its contents into the droplets of the emulsion upon the application of a stimulus.

In another example, a kit comprises reagents for generating capsules within capsules. For example, a kit may comprise reagents for generating inner capsules, reagents for generating outer capsules, and instructions for generating capsules within capsules. As specified throughout this disclosure, any suitable species may be incorporated into the inner and/or outer capsules. A kit of this disclosure may also provide any of these species, such as a polynucleotide comprising a barcode that is pre-partitioned. Similarly, as described throughout the disclosure, the inner capsule may be designed to release its contents into the outer capsule upon the application of a stimulus.

IX. DEVICES

In some cases, this disclosure provides devices comprising partitions for the processing of analytes. A device may be a microwell array, or a microspot array, as described elsewhere in this disclosure. A device may formed in a manner that it comprises any suitable partition. In some cases, a device comprises a plurality of wells, or a plurality of spots. Of course, any partition in a device may also hold other partitions, such as a capsule, a droplet in an emulsion, and the like.

A device may be formed from any suitable material. In some examples, a device is formed from a material selected from the group consisting of fused silica, soda lime glass, borosilicate glass, poly(methyl methacrylate), sapphire, silicon, germanium, cyclic olefin copolymer, polyethylene, polypropylene, polyacrylate, polycarbonate, plastic, and combinations thereof.

In some cases, a device comprises channels for the flow of fluids into and between partitions. Any suitable channels may be used. A device may comprise a fluid inlet and a fluid outlet. The inlet and outlet may be attached to liquid handling devices to introduce species into the device. The device may be sealed, before or after introduction of any species.

Materials that are hydrophilic and/or hydrophobic may be used in different parts of the device. For example, in some cases a device of this disclosure comprises a partition with an interior surface comprising a hydrophilic material. In some cases a surface exterior to the partitions comprises a hydrophobic material. In some cases, a fluid flow path is coated with a hydrophobic or hydrophilic material.

As will be appreciated, the instant disclosure provides for the use of any of the compositions, libraries, methods, devices, and kits described herein for a particular use or purpose, including the various applications, uses, and purposes described herein. For example, the disclosure provides for the use of the compositions, methods, libraries, devices, and kits described herein in partitioning species, in partitioning oligonucleotides, in stimulus-selective release of species from partitions, in performing reactions (e.g., ligation and amplification reactions) in partitions, in performing nucleic acid synthesis reactions, in barcoding nucleic acid, in preparing polynucleotides for sequencing, in sequencing polynucleotides, in polynucleotide phasing, in sequencing polynucleotides from small numbers of cells, in analyzing gene expression, in partitioning polynucleotides from cells, in mutation detection, in neurologic disorder diagnostics, in diabetes diagnostics, in fetal aneuploidy diagnostics, in cancer mutation detection and forensics, in disease detection, in medical diagnostics, in low input nucleic acid applications, such as circulating tumor cell (CTC) sequencing, in a combination thereof, and in any other application, method, process or use described herein.

EXAMPLES

Example 1

Production of a Library of Forked Adapters Comprising Barcode Sequences by Asymmetric PCR and Addition of a Partially Complementary Universal Sequence This example provides methods for the manufacture of forked adapters comprising barcode sequences compatible with next generation sequencing technologies (e.g., ILLUMINA). In this example, the barcode is placed in position 207 as depicted in FIG. 2.

Figure 4:
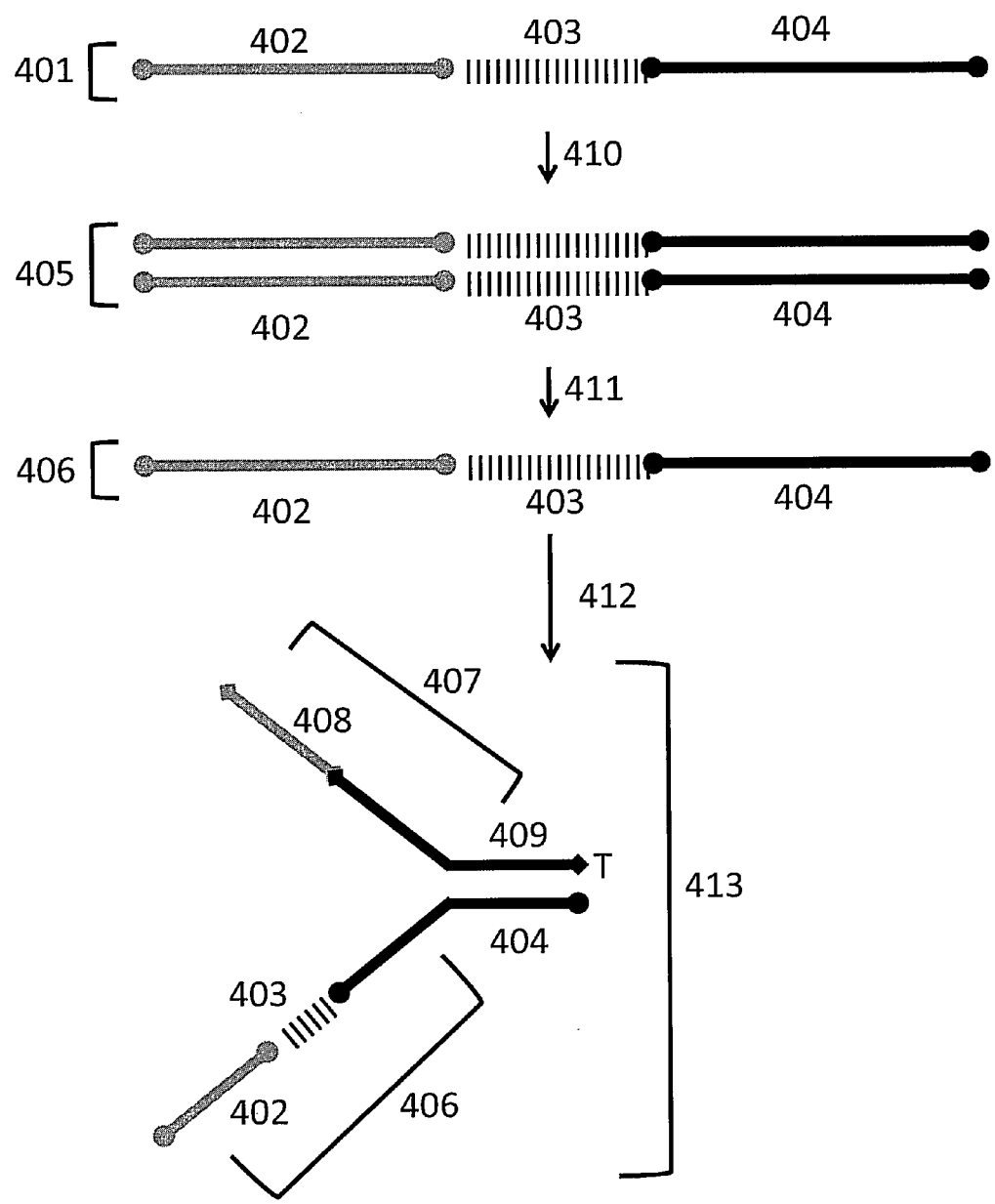
FIG. 4 is a schematic example method used to generate a forked adapter described in Example 1.

With reference to FIG. 4, a single-stranded adapter-barcode polynucleotide sequence 401 comprising a first immobilization region 402, a barcode region 403, and a first sequencing primer region 404 is synthesized. The barcode region 403 is a seven nucleotide random sequence synthesized by including equimolar concentrations of A, G, T, and C in each coupling step.

Following synthesis, the single-stranded adapter-barcode polynucleotide 401 is diluted into aqueous droplets in a water-in-oil emulsion such that each droplet comprises, on average, 0.1 polynucleotides. The droplets also comprise reagents for amplification of the single-stranded adapter-barcode polynucleotide 401, by asymmetric PCR (e.g., polymerase, primers, dNTPs, buffer, salts) and a DNA intercalating dye (e.g., ethidium bromide). The reverse primer is present in excess of the forward primer, or vice versa, enabling asymmetric amplification. The polynucleotides are amplified and the reaction proceeds through an exponential phase of amplification 410, which produces double-stranded products 405, and a linear phase amplification 411, which produces single-stranded products 406.

The droplets are sorted on a fluorescence assisted cell sorter (FACS) 412 to collect droplets comprising amplified polynucleotides. A partially complementary universal sequence 407 is added to the partitions to generate a partially annealed fork structure 413. Partially complementary universal sequence 407 comprises a second immobilization region 408 and a second sequencing primer region 409, the latter of which comprises a T overhang that is compatible with the A overhang on a polynucleotide target to be sequenced (not shown).

Example 2

Fragmentation and Barcoding with Fragmentase

A single-stranded adapter-barcode polynucleotide sequence (e.g., FIG. 4: 401) comprising a first immobilization region 402, a barcode region 403, and a first sequencing primer region 404 is synthesized, partitioned, amplified, and sorted as described in Example 1, or by any other method described in this disclosure. Interfacial polymerization is performed on the droplet comprising the single-stranded adapter-barcode polynucleotide sequence, to generate a plurality of capsules comprising a library of single-stranded adapter-barcode polynucleotide sequences 406, where each (or most) sequences in the library differ in the sequence of their respective barcode regions 403. Thus, a library of encapsulated single-stranded adapter-barcode polynucleotides is generated.

Two mixtures are prepared. Mixture Z1 comprises a target polynucleotide (i.e., a polynucleotide to be fragmented and barcoded), a fragmentase enzyme (e.g., NEBNEXT DSDNA FRAGMENTASE), and a partially complementary universal sequence (e.g., FIG. 4: 407). A second mixture Z2 comprises the library of encapsulated single-stranded adapter-barcode polynucleotides, generated as described above and magnesium chloride in a concentration sufficient to activate the fragmentase enzyme. Mixture Z1, Z2, or both Z1 and Z2 also comprise T4 polymerase, Taq polymerase, and a thermostable ligase.

Figure 5:
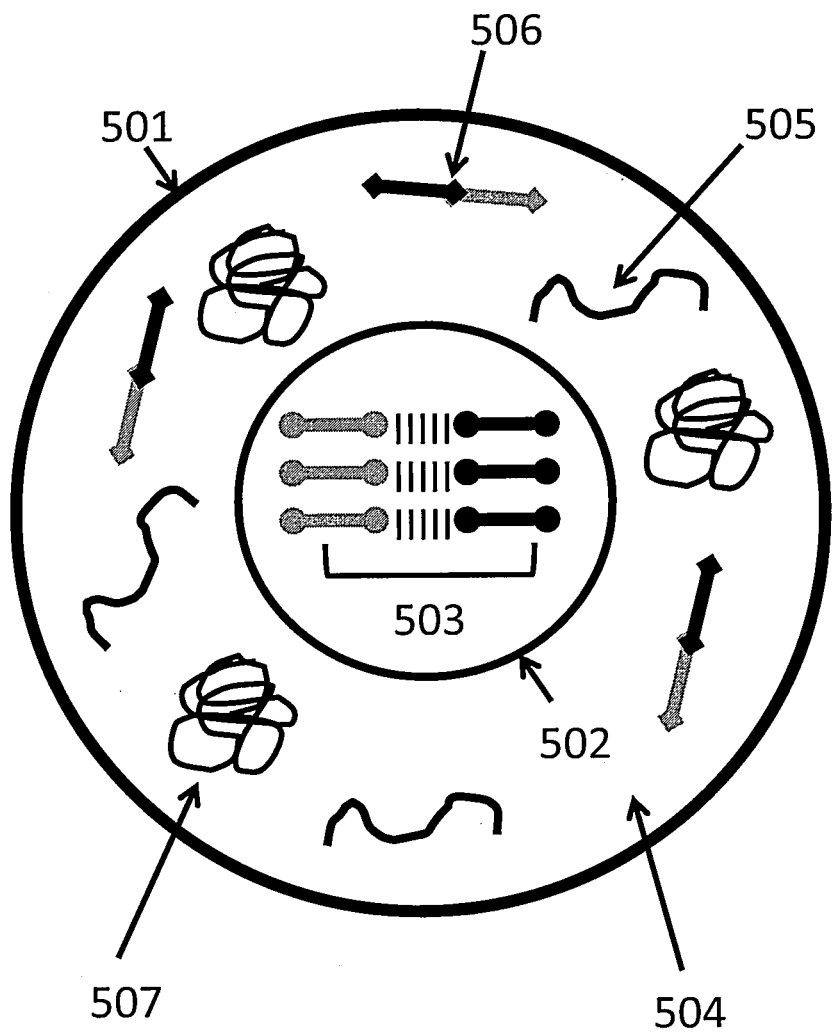
FIG. 5 is a schematic example of a capsule within a capsule described in Example 2.

Mixtures Z1 and Z2 are combined and a capsule within a capsule is formed according to methods described elsewhere in this disclosure, such as flow focusing. FIG. 5 illustrates a capsule within a capsule produced according to the method described above. The outer capsule 501 comprises an inner capsule 502 and medium 504. The inner capsule 502 is one member of the library of encapsulated single-stranded adapter-barcode polynucleotides. Thus, inner capsule 502 comprises multiple copies of a single-stranded adapter-barcode polynucleotide 503, which can be used to attach the same barcode to a polynucleotide within a partition, such as outer capsule 501.

The medium 504 contains the contents of mixtures Z1 and Z2, described above. More specifically, medium 504 comprises target polynucleotide 505, the partially complementary universal sequence 506, and the enzyme mix 507 comprising fragmentase, T4 polymerase, Taq polymerase, thermostable ligase, magnesium chloride, and appropriate buffers.

Upon generation of the capsule within capsule, and exposure of the capsule within capsule to appropriate conditions, the enzymes process the target polynucleotide. More specifically, the fragmentase fragments the target polynucleotide and the T4 polymerase blunts the ends of the fragmented target polynucleotide. The fragmentase and T4 polymerase are then heat inactivated and a stimulus is used to rupture inner capsule 502, releasing its contents into outer capsule 501. The Taq polymerase adds 3'-A overhangs to the fragmented, blunt-ended target polynucleotide. The single-stranded adapter-barcode polynucleotide 503 hybridizes with the partially complementary universal sequence 506, forming a forked adapter with a 3'-T overhang that is compatible with the 3'-A overhang on the fragmented target polynucleotide. The thermostable ligase ligates the forked adapter to the fragmented target polynucleotide, generating barcoded target polynucleotide. The outer capsule 501 is then ruptured, samples from all outer capsules are pooled, and the target polynucleotides are sequenced. Additional preparation steps (e.g., bulk amplification, size selection, etc.) may then be performed as needed prior to sequencing.

In some cases, mixture Z1 comprises multiple versions of the partially complementary universal sequence 506, where each version has its own sample-specific barcode.

Moreover, although the example described above utilizes a thermally stable ligase to attach the forked adapter comprising the barcode sequence to the target polynucleotide, PCR can also be used to accomplish this step, as described elsewhere in this disclosure.

Example 3

Fragmentation and Barcoding by Sonication

A library of encapsulated single-stranded adapter-barcode polynucleotides is generated as described in Example 2, or by any other suitable method described in this disclosure. Target polynucleotides (i.e., polynucleotides to be fragmented) are partitioned into capsules. The capsules comprising the target polynucleotides are configured to withstand ultrasonic stress. The capsules comprising the target polynucleotides are exposed to ultrasonic stress (e.g., COVARIS Focused-Ultrasonicator) and the target polynucleotide is fragmented, generating fragmented target polynucleotide capsules.

A mixture Z1 is prepared, comprising the library of encapsulated single-stranded adapter-barcode polynucleotides (e.g., FIG. 4: 406), the fragmented target polynucleotide capsules, a partially complementary universal sequence (e.g., FIG. 4: 407), an enzyme mixture (T4 polymerase, Taq polymerase, and a thermostable ligase), and appropriate buffers. A capsule within capsule is generated according to the method described elsewhere in this disclosure, such as flow focusing.

Figure 6:
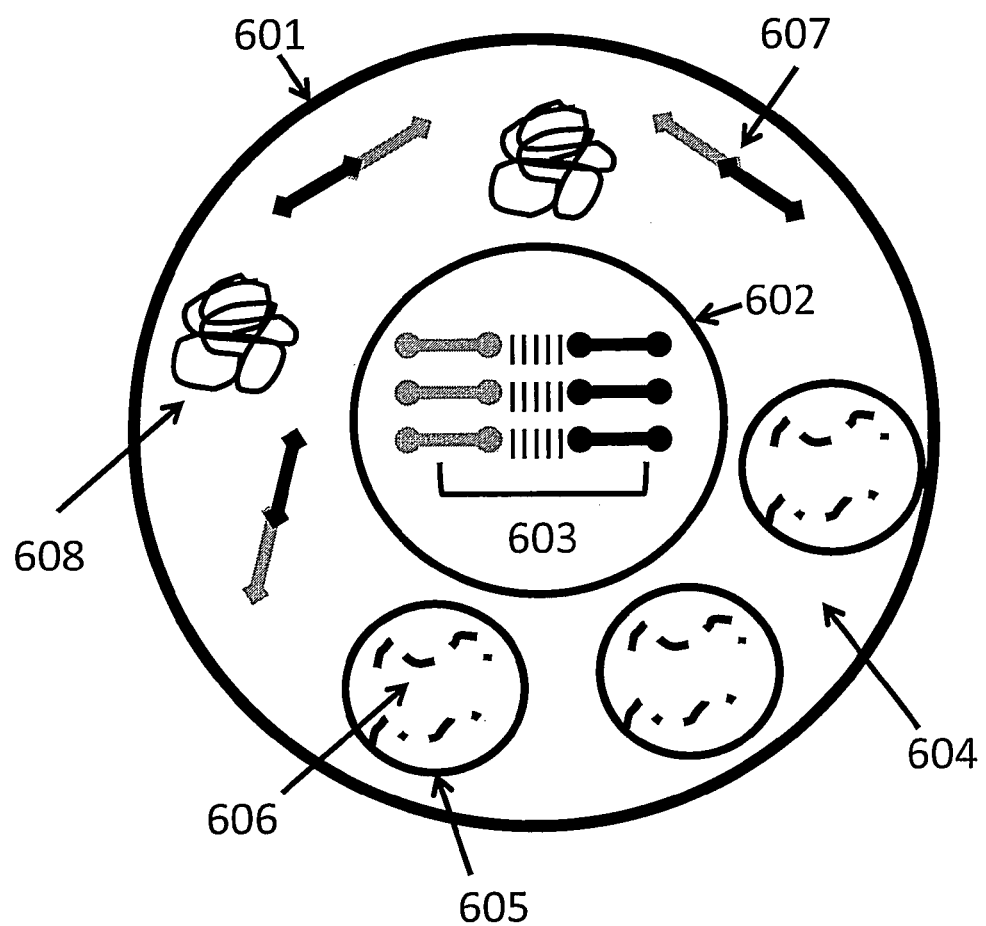
FIG. 6 is a schematic example of capsules within a capsule described in Example 3.

FIG. 6 illustrates capsules within a capsule produced according to the methods described above. The outer capsule 601 comprises a plurality of inner capsules 602 and 605 and medium 604. The inner capsules 602 and 605 include capsules comprising single-stranded adapter-barcode polynucleotides 603 and capsules comprising fragmented target polynucleotide 606, respectively. Inner capsule 602 comprises multiple copies of a single-stranded adapter-barcode polynucleotide 603, which can be used to attach the same barcode to a polynucleotide within a partition, such as the fragmented polynucleotides 606 contained within inner capsules 605.

The medium 604 contains the contents of mixture Z1, described above. More specifically, medium 604 comprises a partially complementary universal sequence 607, an enzyme mixture (T4 polymerase, Taq polymerase, and a thermostable ligase) 608, and appropriate buffers.

Inner capsules 605 comprising fragmented target polynucleotides 606 are exposed to a stimulus to rupture them and release their contents into the contents of outer capsule 601. The T4 polymerase blunts the ends of the fragmented target polynucleotides; the Taq polymerase adds 3'-A overhangs to the fragmented, blunt-ended target polynucleotide. The T4 polymerase and Taq polymerase is then heat-inactivated and a stimulus is applied to release the contents of inner capsule 602 into outer capsule 601. The single-stranded adapter-barcode polynucleotide 603 hybridizes with the partially complementary universal sequence 607, forming a forked adapter with a 3'-T overhang that is compatible with the 3'-A overhang on the fragmented target polynucleotide. The thermostable ligase ligates the forked adapter to the fragmented target polynucleotide, generating a barcoded target polynucleotide. The outer capsule 601 is then ruptured, samples from all outer capsules are pooled, and the target polynucleotides are sequenced.

As described in Example 2, in some cases Z1 can comprise multiple versions of the partially complementary universal sequence 607. Furthermore, although this example demonstrates barcoding of a target polynucleotide by utilizing a thermostable ligase, PCR can also be used to accomplish this step.

Example 4

Figure 7:
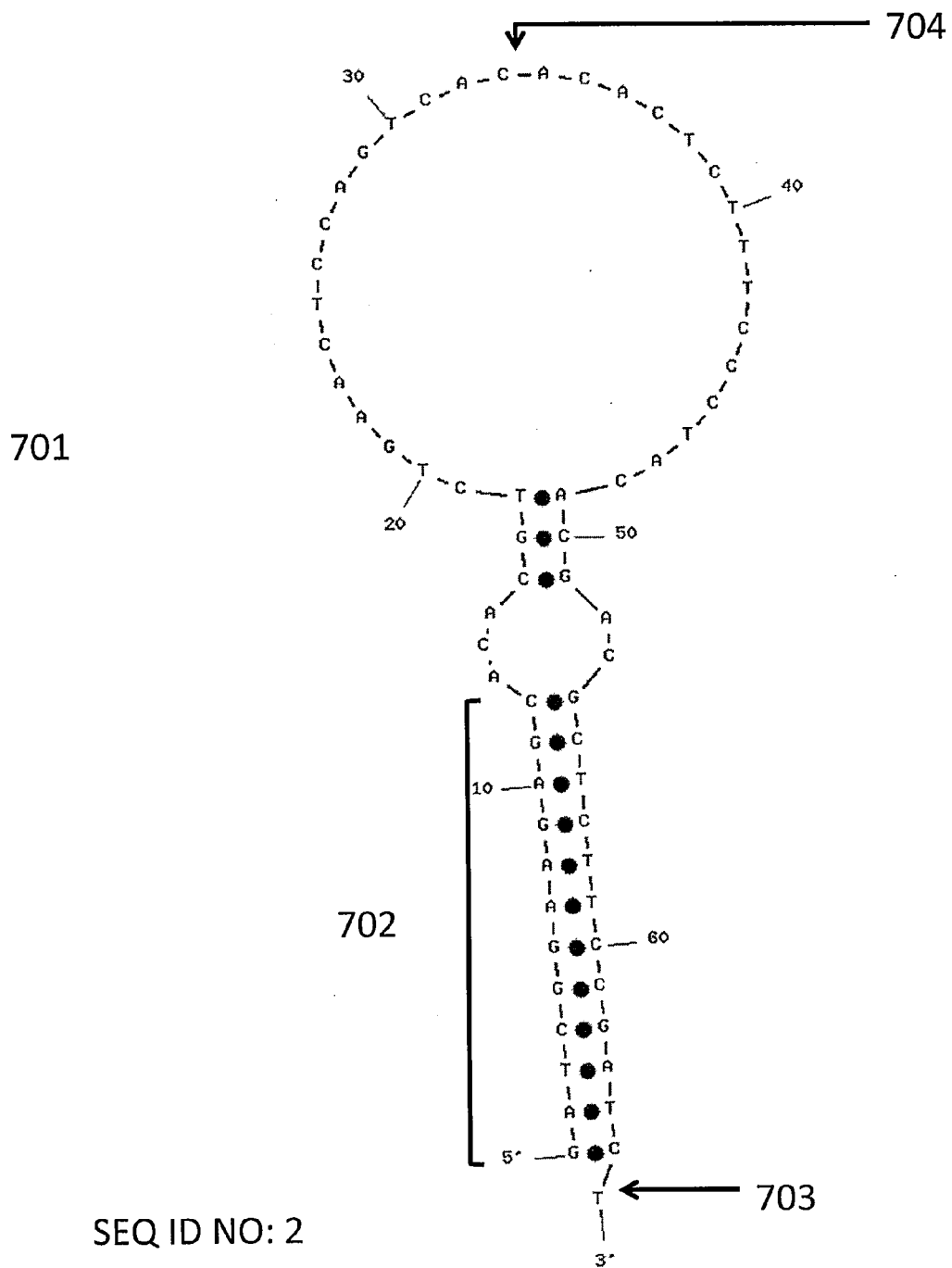
FIG. 7 is a schematic example of a product (or intermediate) that may be generated according to methods of Example 4.

Generation of Forked Adapters by Single Primer Isothermal Amplification (SPIA) and Restriction Digestion This example demonstrates the synthesis of a forked adapter by SPIA and restriction digestion. FIG. 7 provides an example of a product (or intermediate) that may be generated according to the methods of this example. With reference to FIG. 7, a hairpin adapter 701 (SEQ ID NO: 2) is shown that can be used as a precursor to a forked-adapter as described elsewhere in this disclosure. In this example, the hairpin adapter is synthesized as a single-stranded amplification product utilizing SPIA. The hairpin adapter 701 comprises a double-stranded region 702, a 3'-T overhang for AT ligation 703, and a region that can be cut by a restriction enzyme 704 (i.e., between positions 33 and 34). The hairpin adapter may comprise a barcode region and functional regions, such as immobilization regions and regions for annealing of sequencing primers.

Cutting of the adapter (e.g., between positions 33 and 34) generates the forked-adapter depicted in FIG. 8a (SEQ ID NOs: 3-4). The adapter is cut by introducing an oligonucleotide sequence complementary to the region to be cut and exposing the annealed adapter to a restriction enzyme. Ligation of the forked-adapter region depicted in FIG. 8a to a target polynucleotide results in the structure depicted in FIG. 8b (SEQ ID NOs: 5-6). With reference to FIG. 8, the underlined portions of the sequences in FIG. 8b comprise the target polynucleotide with 3'-A overhangs compatible for ligation with the forked adapter depicted in FIG. 8a. The sequences shown in FIG. 8b (SEQ ID NOs: 5-6) are then amplified by polymerase chain reaction to produce SEQ ID NO: 7 (amplification product of SEQ ID NO: 5) and SEQ ID NO: 8 (amplification product of SEQ ID NO: 6), shown in FIG. 8c. In FIG. 8c, SEQ ID NO: 7 represents an amplification product of SEQ ID NO: 5 that adds a first immobilization sequence (underlined 5' portion) and a second immobilization sequence (underlined 3' portion) to SEQ ID NO: 5. SEQ ID NO: 8 represents an amplification product of SEQ ID NO: 6 that replaces the unhybridized portions of SEQ ID NO: 6 with different sequences (underlined 3' portion and underlined 5' portion). Additionally, SEQ ID NO: 8 includes a six nucleotide barcode (TAGTGC; bolded) within the 5' unhybridized region of the polynucleotide. The amplification product therefore comprises barcoded target polynucleotide sequence (represented by 111), immobilization sequences, and a barcode.

Example 5

Additional Forked Adapters by Single Primer Isothermal Amplification (SPIA) and Restriction Digestion This example demonstrates the synthesis of a forked adapter as depicted in FIG. 9a (SEQ ID NOs: 9-10) by SPIA and restriction digestion, where N represents A, T, G, or C. FIG. 9b shows the forked-adapter in single-stranded format (SEQ ID NO: 11), where the single stranded format is capable of forming a hairpin structure. Cutting the hairpin structure at the position designated by the asterisk yields the forked adapter shown in FIG. 9a.

The template for the SPIA will be the sequence shown in FIG. 9c (SEQ ID NO: 12). In FIG. 9c, "R" represents a region of RNA. FIG. 9d shows the hairpin structure formed by the sequence in FIG. 9c. The sequence in FIG. 9d (SEQ ID NO: 12) is treated with polymerase to add nucleotides to the 3' end, generating the sequence shown in FIG. 9e (SEQ ID NO: 13). The sequence in FIG. 9e (SEQ ID NO: 13) is then treated with RNase H, which degrades RNA hybridized to DNA, yielding the sequence in FIG. 9f (SEQ ID NO: 14).

Strand displacement SPIA is then performed on SEQ ID NO: 14. The primer in the strand displacement amplification is of the form RRRRRRRRRRRRR (i.e., $R_{13}$). This primer is an RNA primer that is one base longer than the unhybridized 3' terminus of SEQ ID NO: 14 (i.e., $N_{12}$) (FIG. 9f). More specifically, as shown in FIG. 9f, the 3' terminus of SEQ ID NO: 14 contains twelve N nucleotides. The RNA primer contains 13 nucleotides. Nucleotides 2-13 of the RNA primer are complementary with the twelve unhybridized N nucleotides of SEQ ID NO: 14. Nucleotide 1 of the RNA primer is complementary with the first hybridized base (going from 3' to 5'), in this case, T. The RNA primer displaces the A and generates the double-stranded extension product shown in FIG. 9g (SEQ ID NOs: 15-16). Because only one primer is present, the reaction produces multiple copies of the single-stranded product. The single-stranded amplification products are treated with RNase H to generate the single-stranded amplification products shown in FIG. 9h (SEQ ID NO: 17). FIG. 9i shows this sequence in 5'-3' format (SEQ ID NO: 17). FIG. 9j shows this sequence in hairpin format (SEQ ID NO 17).

The hairpin adapter shown in FIG. 9j is then ligated to a fragmented polynucleotide with a 3'-A overhang. The hairpin is cleaved between the A and C residues separated by the curved line in FIG. 9j by adding an oligonucleotide complementary to that region and cutting with a restriction enzyme. This generates a forked adapter. PCR amplification is then conducted, as described in Example 4, to add immobilization regions and barcodes to the forked adapter that is attached to the target polynucleotide.

Example 6

Generation of Forked Adapters Comprising Barcodes by Exponential PCR and Hybridization This example demonstrates the production of forked adapters comprising barcodes by hybridization. FIG. 10a shows the exemplary forked adapter provided in FIG. 8a. As described in Example 4, this adapter may be ligated to a target polynucleotide and then an amplification reaction may be performed to add additional functional sequences, including a barcode. However, a barcode (and other functional sequences) may also be incorporated directly into the forked adapter, prior to attachment of the forked adapter to the target polynucleotide. For example, FIG. 10b shows the forked adapter of FIG. 10a, with the addition of a first immobilization region (underlined) and a seven nucleotide barcode region (bold/underline; "N").

The barcoded forked adapter of FIG. 10b is produced by first synthesizing SEQ ID NO: 18 as a single strand. The diversity in the barcode region is generated using an equimolar mixture of A, G, T, and C, as described throughout this disclosure. Droplet-based PCR is performed, as described in Example 1. However, one DNA primer and one RNA primer are used to amplify SEQ ID NO: 18 in the droplets. The amplification is conducted in the presence of an intercalating dye, and droplets comprising amplified SEQ ID NO: 18 are isolated, as described in Example 1. FIG. 10c shows the double-stranded amplification product. The underlined portion of SEQ ID NO: 19 is an RNA strand derived from the RNA primer. The sequences shown in FIG. 10c are then treated with RNase H, which digests the underlined RNA region, yielding the construct shown in FIG. 10d. In order to generate a forked construct, a partially complementary universal sequence (SEQ ID NO: 21) is added to the construct shown in FIG. 10d, producing the product shown in FIG. 10e. The advantage to utilizing this process is that it utilizes the significantly greater amplification of polynucleotides provided by exponential PCR versus the linear amplification of polynucleotides provided by SPIA.

Example 7

Dual Indexing Approach

This example demonstrates an approach for synthesis of barcodes for dual-index reads. A dual-index read is a read of both strands of a double-stranded fragment, using barcodes attached to each strand. FIG. 11 shows an example of the synthesis of barcodes for a dual-indexing approach and an example use of the barcodes in a capsules in a capsule configuration.

Figure 11A:
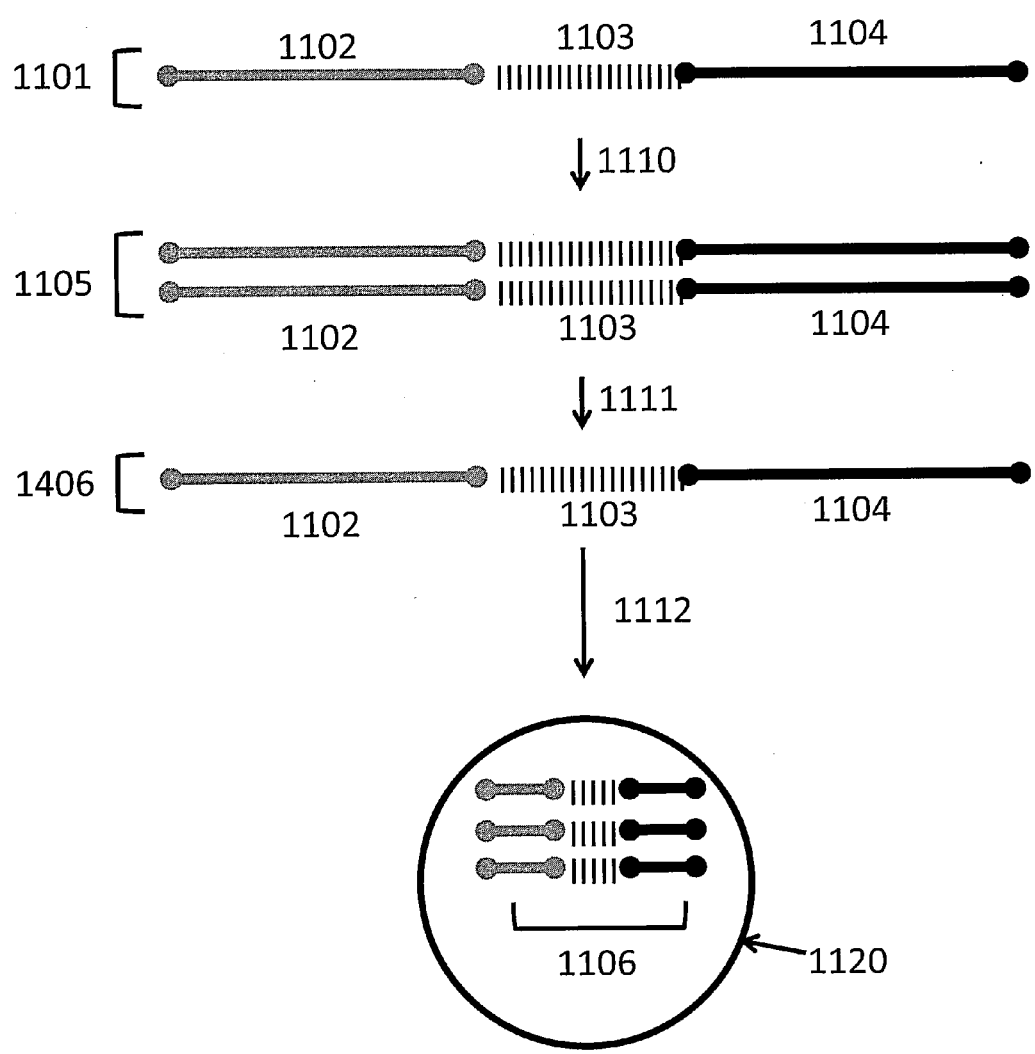
FIGS. 11a-d schematically depict methods and structures described in Example 7.
Figure 11B:
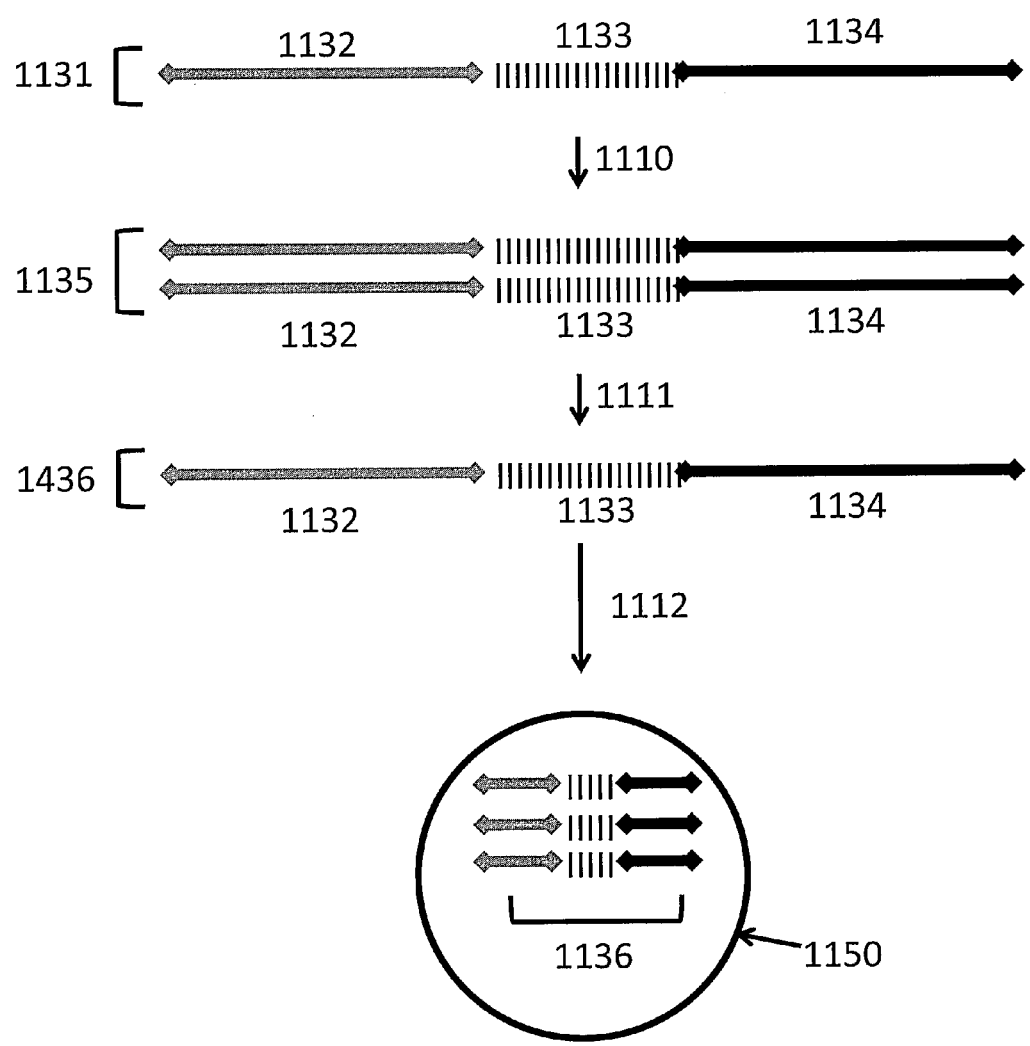

As shown in FIG. 11a, a first single-stranded adapter-barcode polynucleotide sequence 1101 comprising a first immobilization region 1102, a first barcode region 1103, and a first sequencing primer region 1104 is synthesized. In parallel, as shown in FIG. 11b, a second single-stranded adapter-barcode polynucleotide sequence 1131, comprising a second immobilization region 1132, a second barcode region 1133, and a second sequencing primer region 1134 is synthesized. In some cases, barcode regions 1103 and 1133 are of the same sequence. In other cases, barcode regions 1103 and 1133 are of different sequences or of partially different sequences.

Following synthesis, the single-stranded adapter-barcode polynucleotides 1101 (FIG. 11a) and 1131 (FIG. 11b) are, in parallel, diluted into aqueous droplets in a water-in-oil emulsion. The droplets also comprise reagents for amplification of the single-stranded adapter-barcodes polynucleotide 1101 (FIG. 11a) and 1131 (FIG. 11b) respectively, by asymmetric PCR (e.g., polymerase, primers, dNTPs, buffer, salts) and a DNA intercalating dye (e.g., ethidium bromide). The reverse primer is present in excess of the forward primer, or vice versa, enabling asymmetric amplification. The polynucleotides 1101 (FIG. 11a) and 1131 (FIG. 11b) are amplified and the reaction proceeds through an exponential phase of amplification 1110, which produces double-stranded products 1105 (FIG. 11a) and 1135 (FIG. 11b), and a linear phase amplification 1111, which produces single-stranded products 1106 (FIG. 11a) and 1136 (FIG. 11b) respectively.

The droplets are sorted on a fluorescence assisted cell sorter (FACS) 1112 to collect droplets comprising amplified polynucleotides.

Interfacial polymerization is then performed on the droplets comprising the single-stranded adapter-barcode polynucleotide sequences 1106 and 1136 droplets respectively, to generate two types of capsules 1120 (FIG. 11a) and 1150 (FIG. 11b), each comprising one of single-stranded adapter barcode polynucleotide sequences 1106 or 1136 respectively.

Two mixtures are prepared. Mixture Z1 comprises a target polynucleotide (i.e., a polynucleotide to be fragmented and barcoded) 1170 and a fragmentase enzyme (e.g., NEBNEXT DSDNA FRAGMENTASE). A second mixture Z2 comprises capsules 1120 and 1180, generated as described above and magnesium chloride in a concentration sufficient to activate the fragmentase enzyme. Mixture Z1, Z2, or both Z1 and Z2 also comprise T4 polymerase, Taq polymerase, and a thermostable ligase.

Figure 11C:
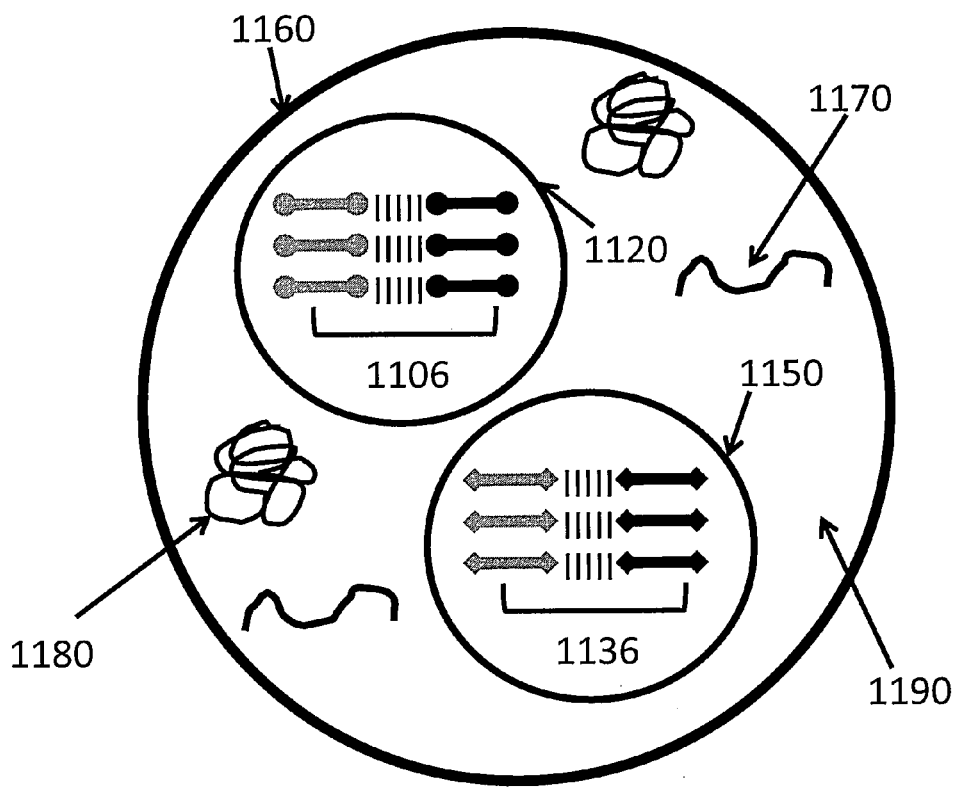
Figure 11D:
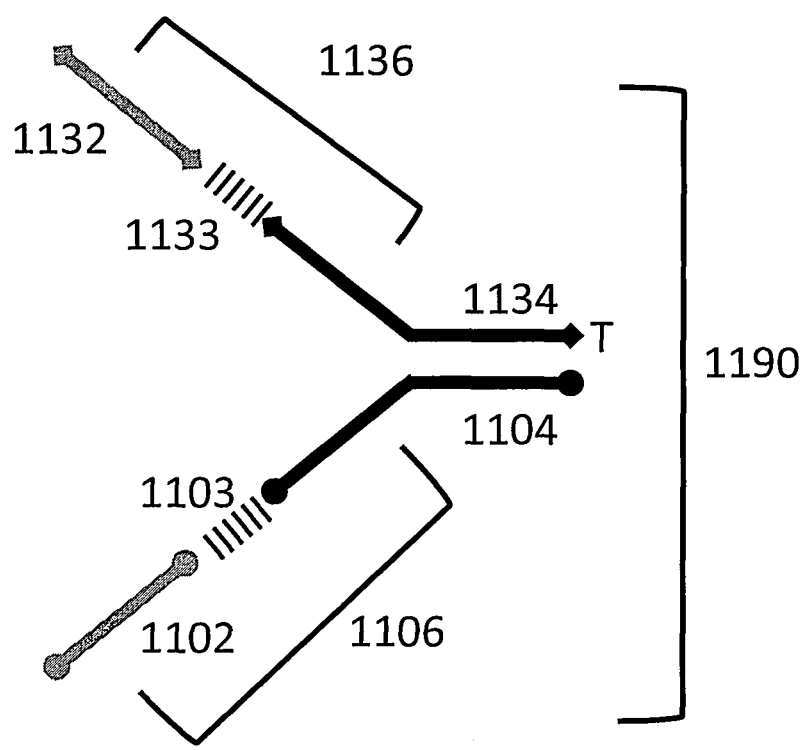

Mixtures Z1 and Z2 are combined and a capsule within a capsule is formed according to methods described elsewhere in this disclosure, such as flow focusing. FIG. 11c illustrates capsules within a capsule produced according to the method described above. The outer capsule 1160 comprises capsules 1120 and 1150 and medium 1190. Thus, capsules 1120 and 1150 each comprise multiple copies of single-stranded adapter-barcode polynucleotides 1106 and 1136, respectively, and can be used to attach barcodes 1103 and 1133 to a polynucleotide within a partition, such as target polynucleotide 1170 in medium 1190 of outer capsule 1160.

The medium 1190 contains the contents of mixtures Z1 and Z2, described above. More specifically, medium 1190 comprises target polynucleotide 1170 and the enzyme mix 1180 comprising fragmentase, T4 polymerase, Taq polymerase, thermostable ligase, magnesium chloride, and appropriate buffers.

Upon generation of the capsules within a capsule, and exposure of the capsules within the capsule to appropriate conditions, the enzymes process the target polynucleotide. More specifically, the fragmentase fragments the target polynucleotide and the T4 polymerase blunts the ends of the fragmented target polynucleotide. The fragmentase and T4 polymerase are then heat inactivated and a stimulus is used to rupture capsules 1120 and 1150, releasing their contents into medium 1190 of outer capsule 1160. The Taq polymerase adds 3'-A overhangs to the fragmented, blunt-ended target polynucleotide. The single-stranded adapter-barcode polynucleotide 1106 hybridizes with single-stranded adapter-barcode polynucleotide 1136, forming a forked adapter, comprising barcode regions 1103 and 1133, with a 3'-T overhang that is compatible with the 3'-A overhang (not shown) on the fragmented target polynucleotide. The thermostable ligase ligates the forked adapter to the fragmented target polynucleotide, generating barcoded target polynucleotide. The outer capsule 1160 is then ruptured, samples from all outer capsules are pooled, and the target polynucleotides are sequenced.

Moreover, although the example described above utilizes a thermally stable ligase to attach the forked adapter comprising the barcode sequence to the target polynucleotide, PCR can also be used to accomplish this step, as described elsewhere in this disclosure.

Example 8

Figure 14A:
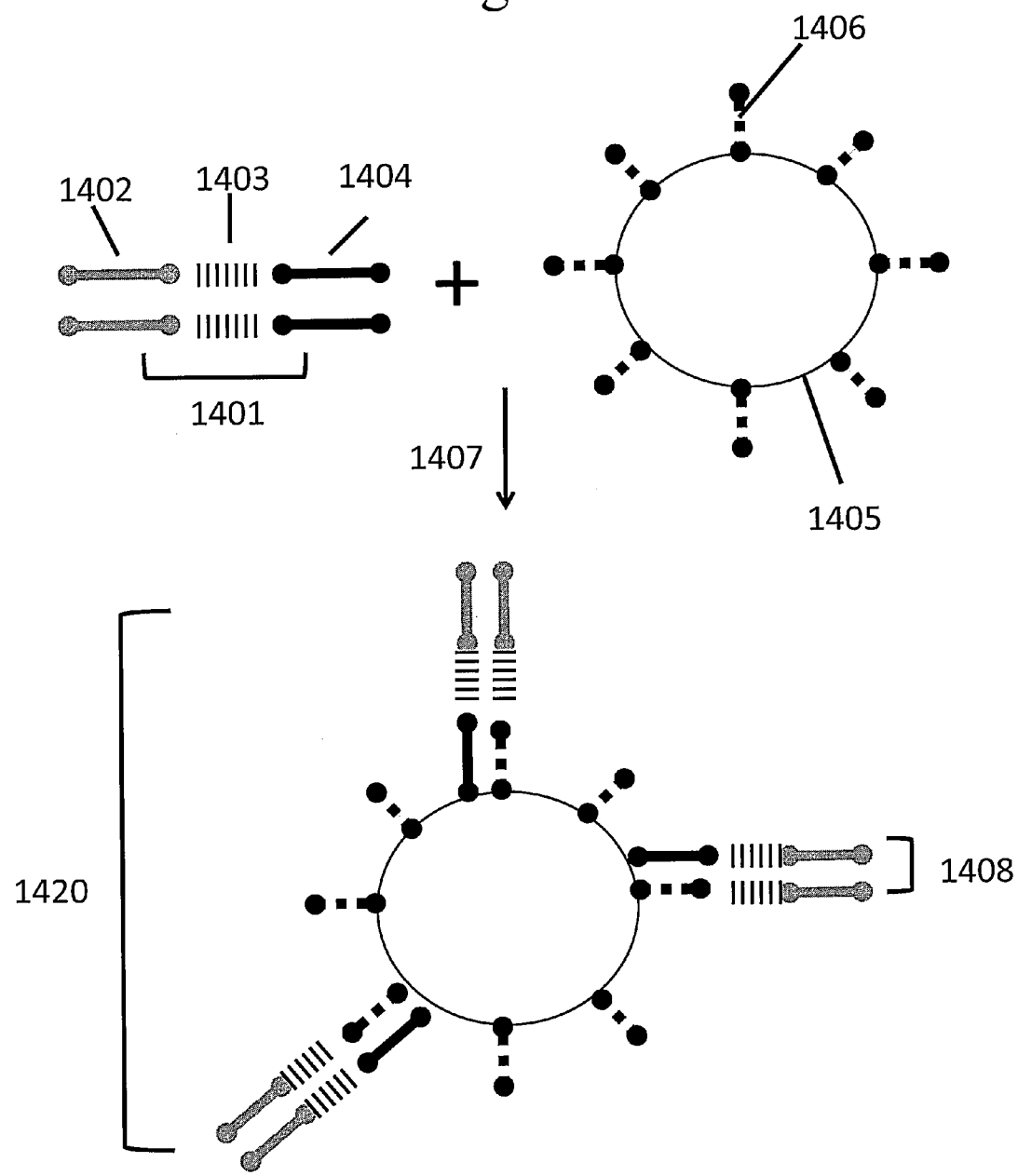
FIGS. 14a-e schematically depict methods and structures described in Example 8.

Production of a Forked Adapter Comprising Barcode Sequences by Bead Emulsion PCR and Addition of a Partially Complementary Universal Sequence As shown in FIG. 14a, a single-stranded adapter-barcode sequence 1401 comprising a first immobilization region 1402, a barcode region 1403, and a first sequencing primer region 1404 is synthesized. Following synthesis, the single-stranded adapter-barcode sequence 1401 is diluted into aqueous droplets in a water-in-oil emulsion such that each droplet comprises, on average, 1 polynucleotide. The droplets also comprise first beads 1405 that are linked, via a photolabile linker, to one or more copies of an RNA primer 1406 complementary to a sequence comprised in the first sequencing primer region 1404; a DNA primer complementary to a sequence (not shown) comprised in the first immobilization region 1402; and reagents necessary for amplification (e.g., polymerase, dNTPs, buffer, salts) of single-stranded adapter-barcode sequence 1401. The polynucleotides are amplified 1407 which produces double-stranded products 1408 both attached to the first beads 1405 to form structure 1420 and in solution (not shown).

Figure 14B:
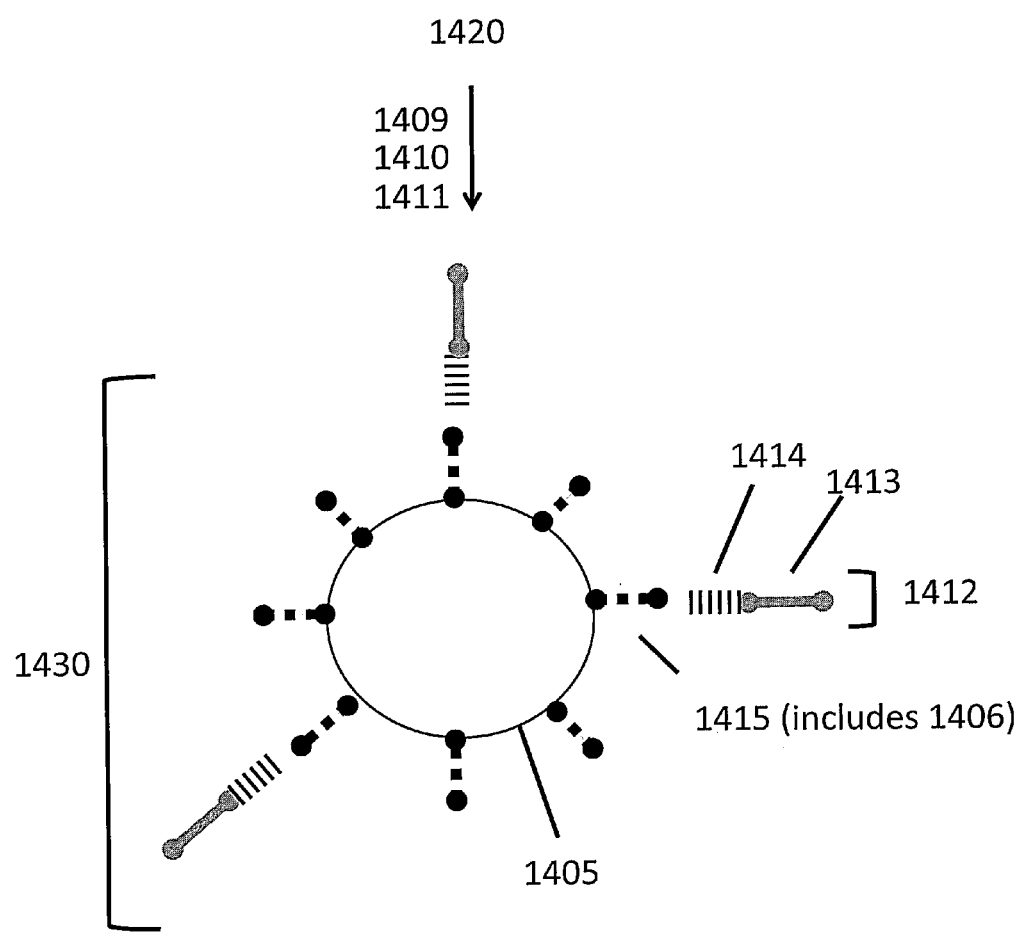

The emulsion is then broken and the emulsion components are pooled to form a product mixture. As shown in FIG. 14b, the liberated beads are then washed 1409 (via centrifugation) several times with appropriate medium, treated with sodium hydroxide (NaOH) 1410 to denature the double-stranded products attached to the first beads 1405, and then further washed 1411. After denaturation 1410 and washing 1411 of structure 1420, the resulting structure 1430 comprises a single-stranded complement 1412 to the single-stranded adapter-barcode sequence 1401, comprising a complementary immobilization region 1413, a complementary barcode region 1414, and a complementary sequencing primer region 1415. As shown, the complementary sequencing primer region 1415 comprises the RNA primer 1406. Structure 1430 is then resuspended in an appropriate medium.

Figure 14C:
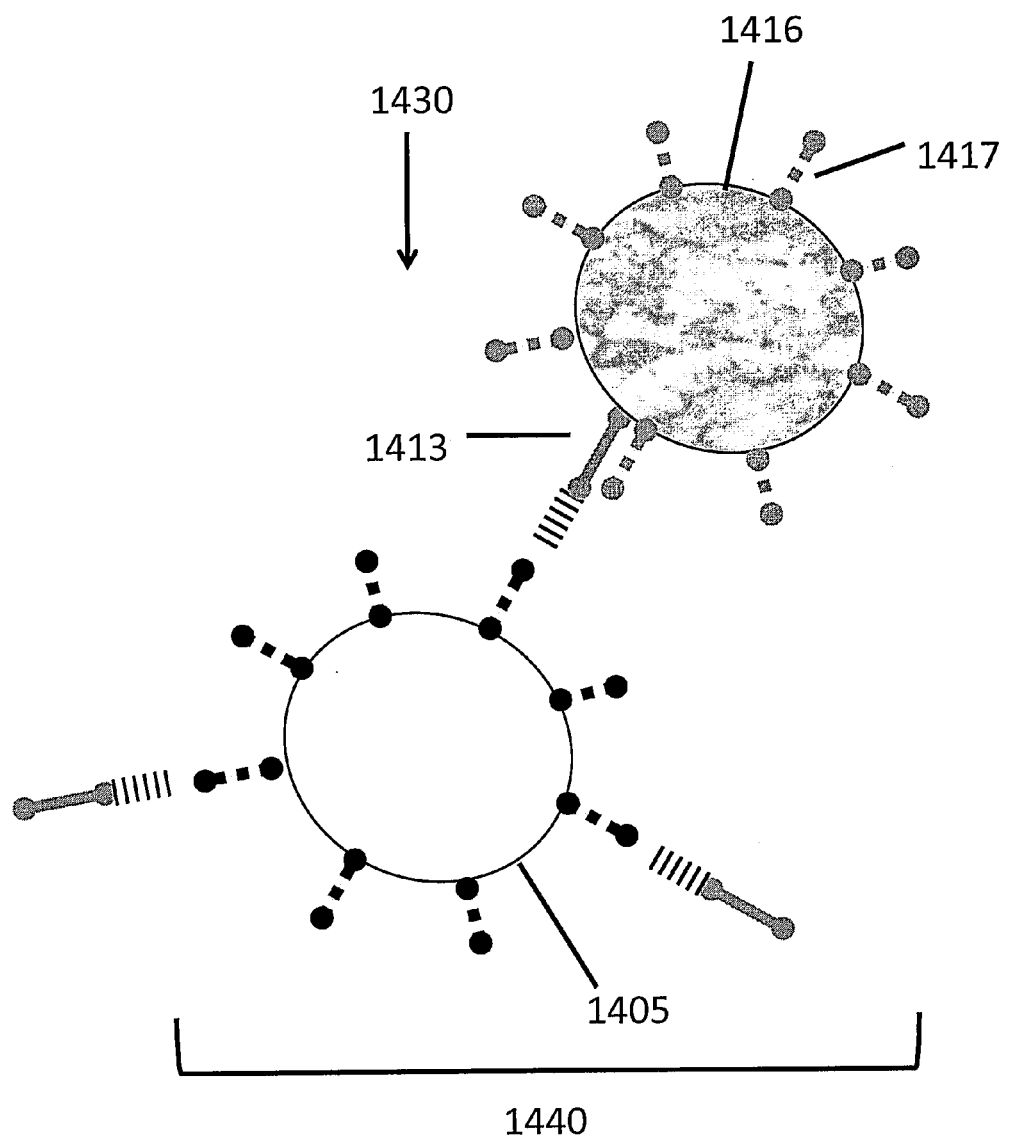

Next, as shown in FIG. 14c, second beads 1416 that comprise one or more copies of a DNA polynucleotide 1417 complementary to the complementary immobilization region 1413 are then added to the medium. Via the complementary DNA polynucleotide 1417 and the complementary immobilization region 1413 of the single-stranded complement 1412, the second beads 1416 bind to the single-stranded complement 1412. The single stranded complement is now bound at one end to first bead 1405 and at its other end second bead 1416 to form structure 1440.

Figure 14D:
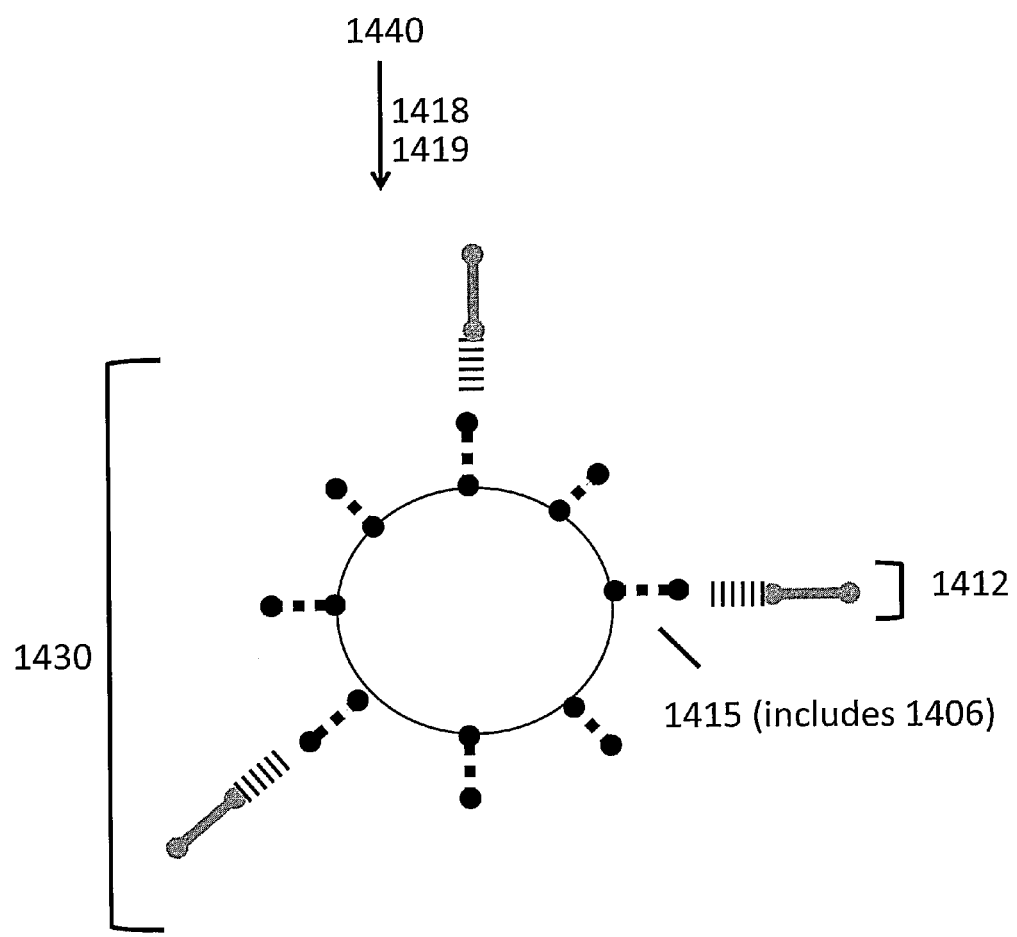

As shown in FIG. 14d, structure 1440 is then centrifuged 1418 using a glycerol gradient to separate structure 1440 from structure 1430 not comprised in structure 1440. In cases where the second beads 1416 are magnetic, a magnetic separation may be used as an alternative. The product is then treated with NaOH 1419 to denature the single-stranded complement 1412 from the second bead 1416, resulting in regeneration of structure 1430. Structure 1430 is then subject to several rounds of washing (via centrifugation) to remove second beads 1416. Single-stranded complement 1412, attached to structure 1430, represents a single-stranded barcode adapter.

Figure 14E:
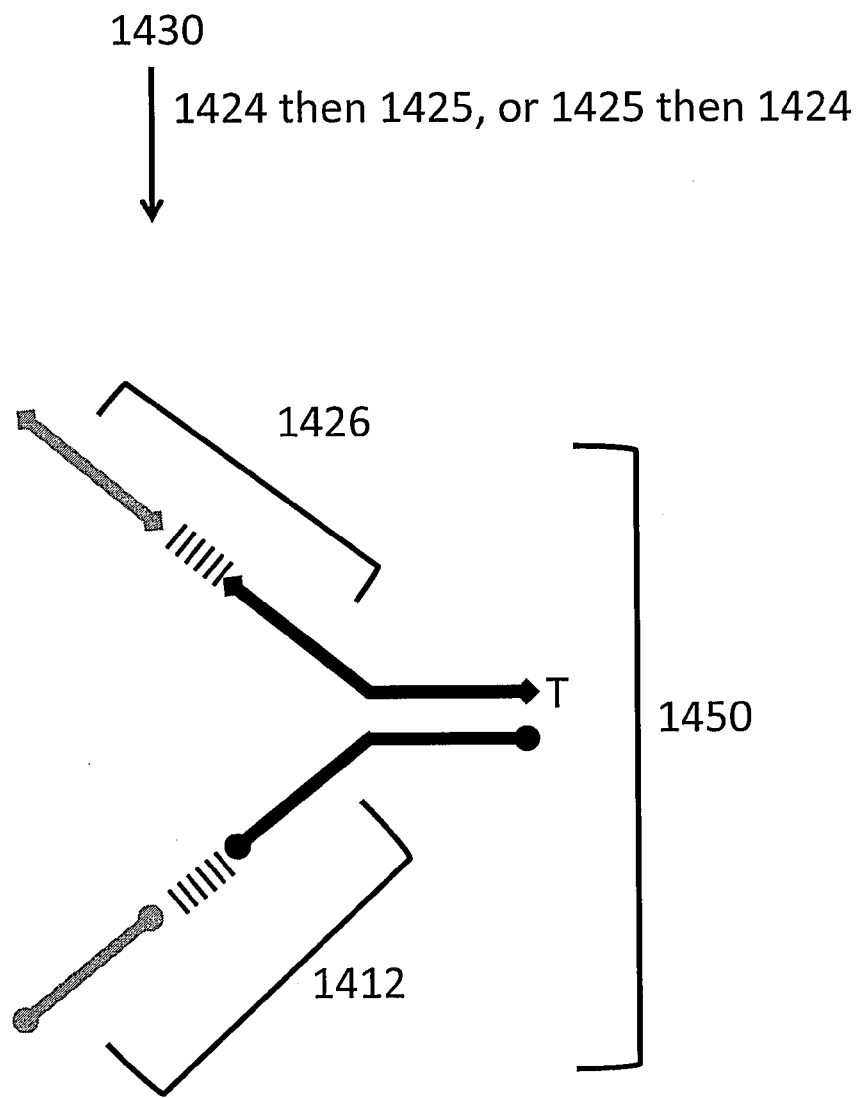

As shown in FIG. 14e, single-stranded complement 1412 can be used to generate a forked adapter. To generate a forked adapter 1450, the single-stranded complement 1412 is then released 1424 from structure 1430 with light and then combined 1425 with a universal complementary sequence 1426 or is first combined 1425 with a universal complementary sequence 1426 and then released 1424 from structure 1430. In order to generate ligatable ends, RNAase H is used to digest the RNA primer 1406 of the single-stranded complement 1412 and a Type IIs restriction enzyme is used to generate a single base T overhang on the universal complementary sequence 1426. The T overhang is compatible with the A overhang on a polynucleotide target to be sequenced (not shown).

Example 9

Figure 15A:
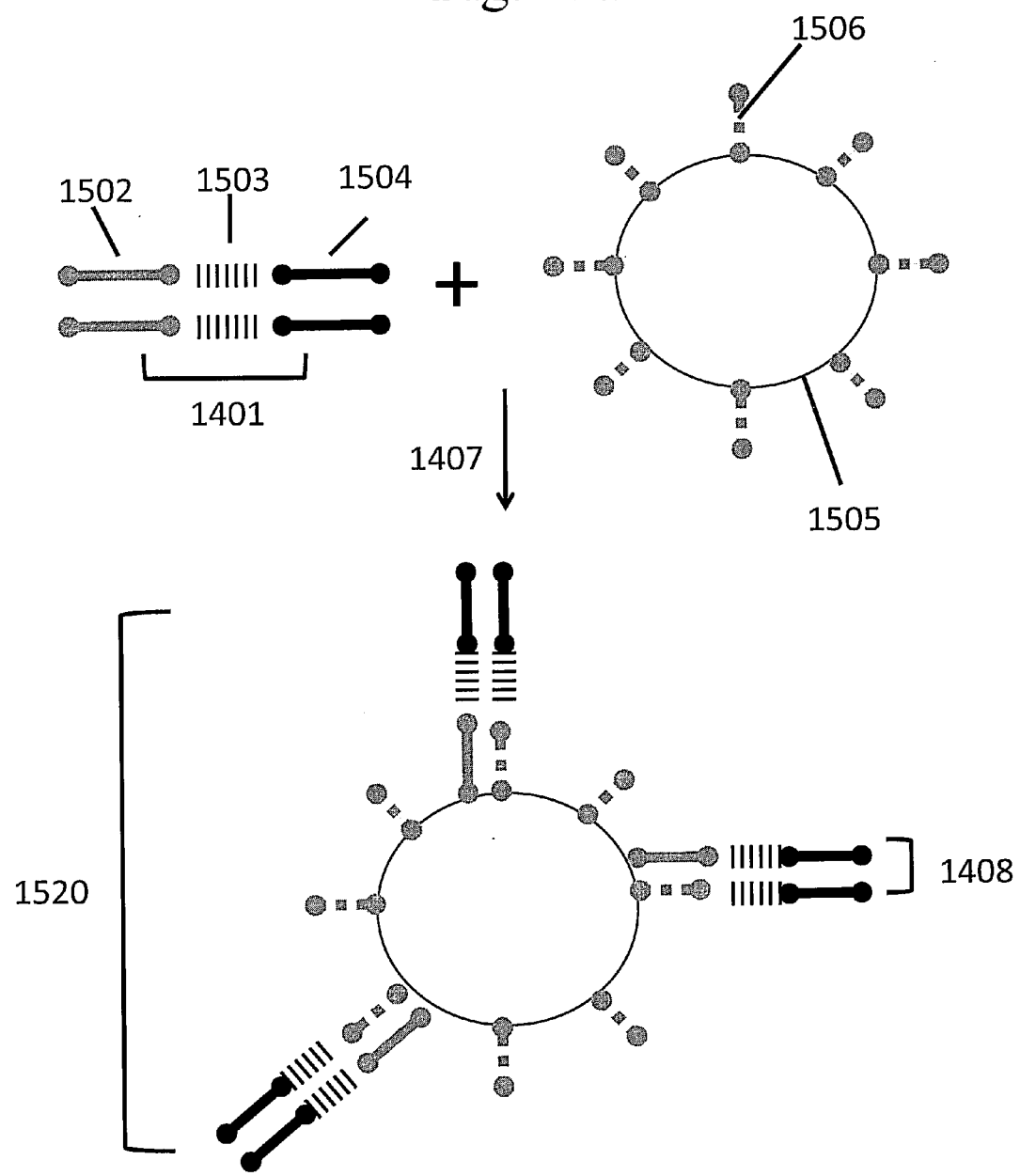

Production of a Forked Adapter Comprising Barcode Sequences by Bead Emulsion PCR and Addition of a Partially Complementary Universal Sequence As shown in FIG. 15a, a single-stranded adapter-barcode sequence 1501 comprising a first immobilization region 1502, a barcode region 1503, and a first sequencing primer region 1504 is synthesized. Following synthesis, the single-stranded adapter-barcode sequence 1501 is diluted into aqueous droplets in a water-in-oil emulsion such that each droplet comprises, on average, 1 polynucleotides. The droplets also comprise first beads 1505 that are linked, via a photolabile linker, to one or more copies of an RNA primer 1506 complementary to a sequence comprised in the first immobilization region 1502; a DNA primer complementary to a sequence (not shown) comprised in the first sequencing primer region 1502; and reagents necessary for amplification (e.g., polymerase, dNTPs, buffer, salts) of single-stranded adapter-barcode sequence 1501. The polynucleotides are amplified 1507 which produces double-stranded products 1508 both attached to the first beads 1505 to form structure 1520 and in solution (not shown).

The emulsion is then broken and the emulsion components are pooled to form a product mixture. As shown in FIG. 15b, the liberated beads are then washed 1509 (via centrifugation) several times with appropriate medium, treated with sodium hydroxide (NaOH) 1510 to denature the double-stranded products attached to the first beads 1505, and then further washed 1511. After denaturation 1510 and washing 1511 of structure 1520, the resulting structure 1430 comprises a single-stranded complement 1512 to the single-stranded adapter-barcode sequence 1501, comprising a complementary immobilization region 1513, a complementary barcode region 1514, and a complementary sequencing primer region 1515. As shown, the complementary sequencing primer region 1515 comprises the RNA primer 1506. Structure 1530 is then resuspended in an appropriate medium.

Figure 15C:
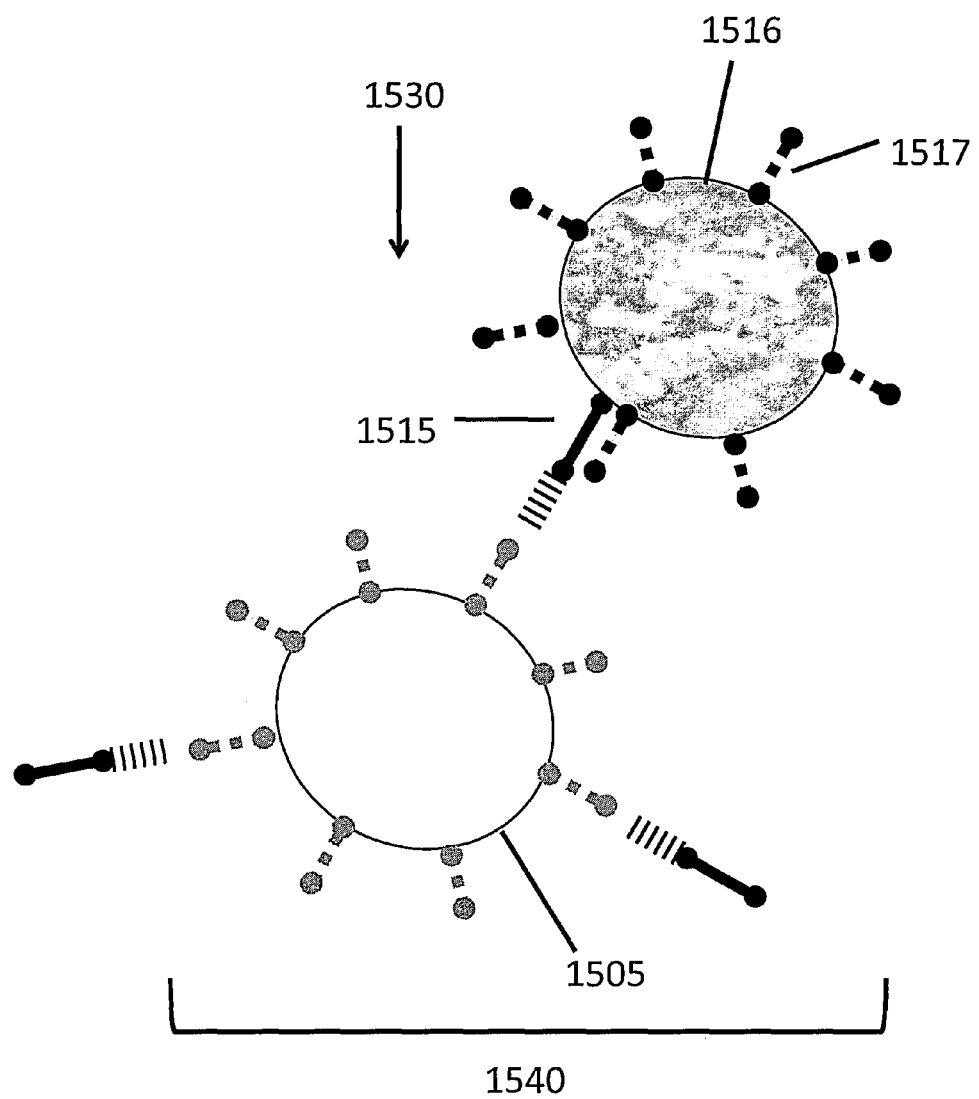

Next, as shown in FIG. 15c, second beads 1516 that comprise one or more copies of a DNA polynucleotide 1517 complementary to the complementary sequencing primer region 1515 are then added to the medium. Via the complementary DNA polynucleotide 1517 and the complementary sequencing primer region 1515 of the single-stranded complement 1512, the second beads 1416 bind to the single-stranded complement 1512. The single stranded complement is now bound at one end to first bead 1505 and at its other end second bead 1516 to form structure 1540.

Figure 15D:
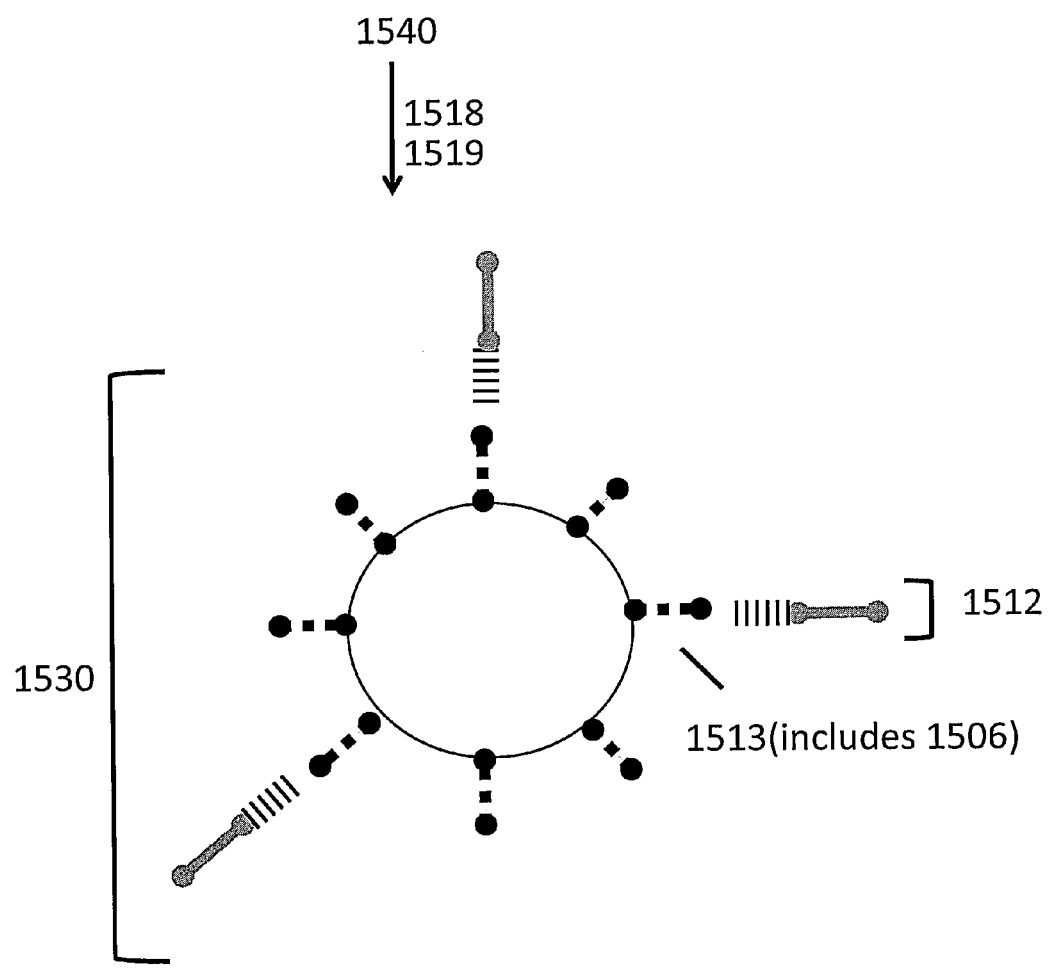

As shown in FIG. 15d, structure 1540 is then centrifuged 1518 using a glycerol gradient to separate structure 1540 from structure 1530 not comprised in structure 1540. In cases where the second beads 1516 are magnetic, a magnetic separation may be used as an alternative. The product is then treated with NaOH 1519 to denature the single-stranded complement 1512 from the second bead 1516, resulting in regeneration of structure 1530. Structure 1530 is then subject to several rounds of washing (via centrifugation) to remove second beads 1516. Single-stranded complement 1512, attached to structure 1530, represents a single-stranded barcode adapter.

Figure 15E:
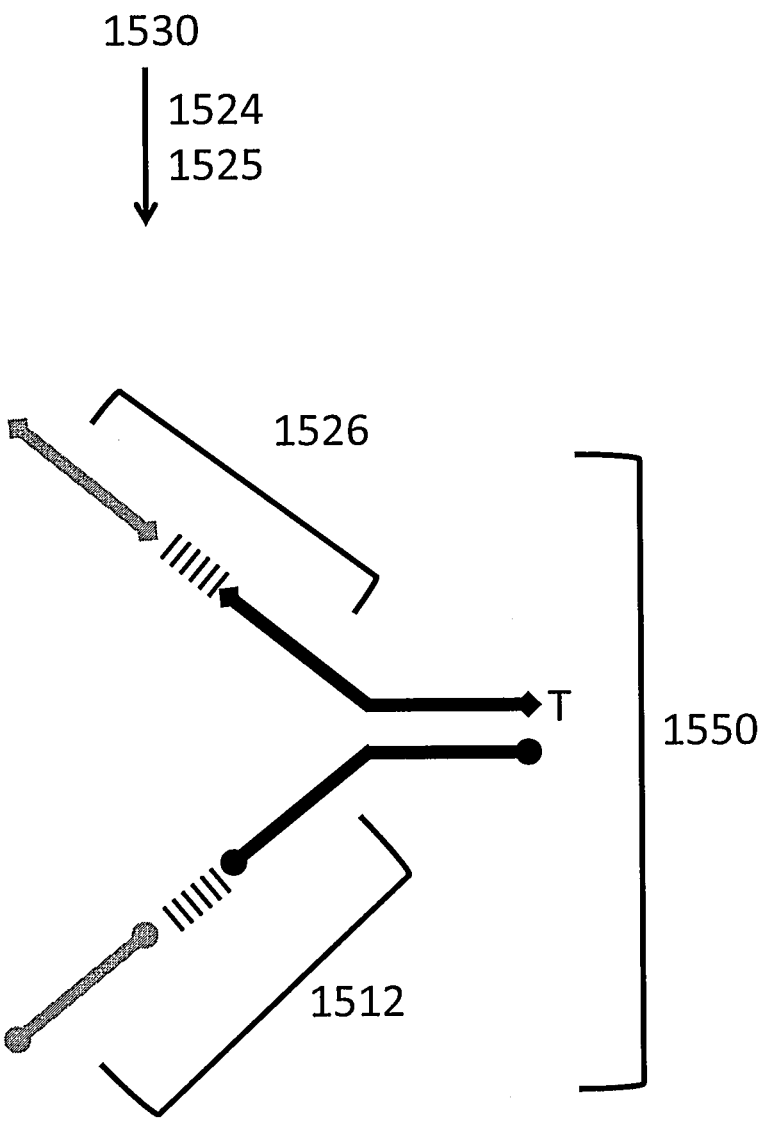

As shown in FIG. 15e, single-stranded complement 1512 can be used to generate a forked adapter. To generate a forked adapter 1550, the single-stranded complement 1512 is then optionally released 1524 from structure 1530 with light and then combined 1525 with a universal complementary sequence 1526. In order to generate ligatable ends, a Type IIs restriction enzyme is used to generate a single base T overhang on the universal complementary sequence 1526. The T overhang is compatible with the A overhang on a polynucleotide target to be sequenced (not shown).

Example 10

Figure 16:
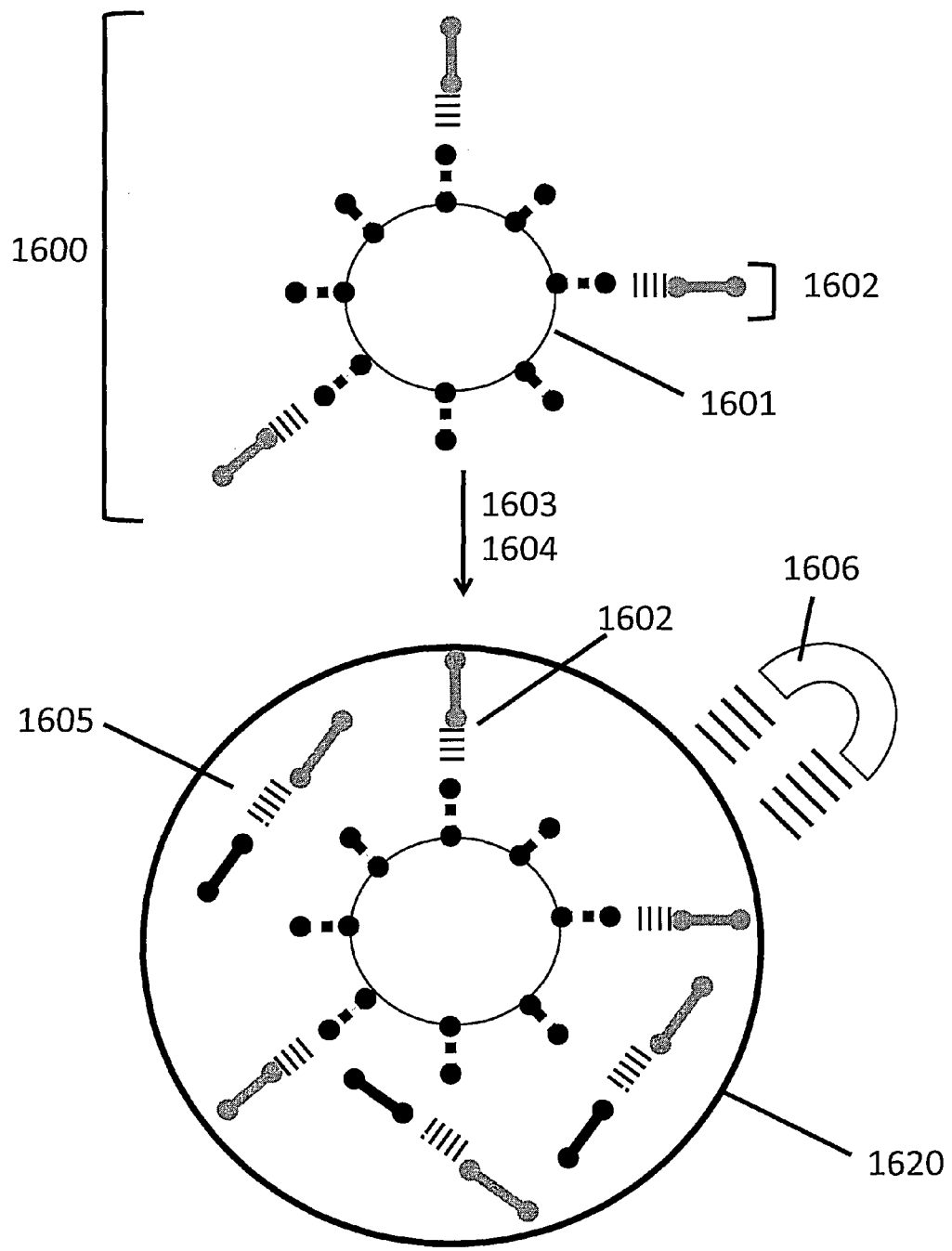
FIG. 16 schematically depicts methods and structures described in Example 10.

Production of a Forked Adapter Template Barcode Sequences by Bead Emulsion PCR and an Adapter Derived Therefrom As shown in FIG. 16, structure 1600 comprising a magnetic bead (1601)-bound single-stranded adapter-barcode sequence 1602 is produced according to methods described in Example 8, Example 9, or any other method described herein. Next, structure 1600 is partitioned into capsules (or alternatively, another emulsion) 1620 by methods described herein, for example, interfacial polymerization. The capsules 1620 also comprise reagents for amplification of the single-stranded adapter-barcode sequence 1602, by asymmetric PCR (e.g., polymerase, primers, dNTPs, buffer, salts). The reverse primer is present in excess of the forward primer, or vice versa, enabling asymmetric amplification. Single-stranded adapter-barcode sequence 1602 is amplified 1603 and the reaction proceeds through a linear phase amplification 1604, which produces single-stranded adapter product 1605, complementary to single-stranded barcode adapter-template 1602. At this juncture, capsules 1620 comprise both single-stranded adapter 1605 in solution and magnetic bead (1601)-bound single-stranded adapter-barcode sequence 1602. Capsules 1620 are then separated from those not comprising beads (and thus templates 1602 and single-stranded adapters 1605) by magnetic separation 1606. Capsules 1620 may be ruptured and forked adapters generated as described in Example 9.

Example 11

Barcoding with Bead Emulsion PCR and Fragmentation with Fragmentase

Figure 17:
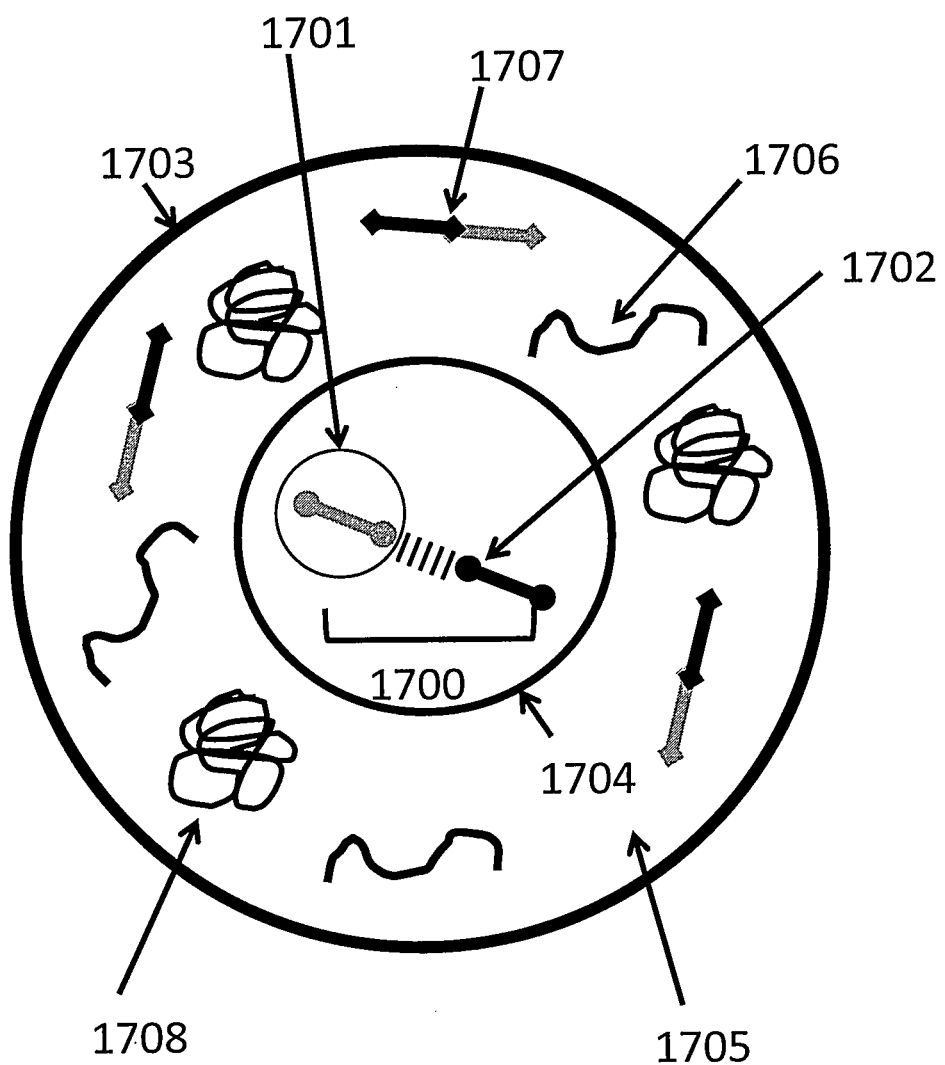
FIG. 17 schematically depicts a capsule within a capsule described in Example 11.

As shown in FIG. 17, structure 1700 comprising a magnetic bead (1701)-bound single-stranded adapter-barcode sequence 1702 is produced according to methods described in Example 8, Example 9, or any other method described herein. Interfacial polymerization is performed on the droplet comprising the structure 1700, to generate a capsule 1704 comprising single-stranded adapter-barcode sequence 1702 attached, via a photolabile linker, to a bead 1701.

Two mixtures are prepared. Mixture Z1 comprises a target polynucleotide (i.e., a polynucleotide to be fragmented and barcoded), a fragmentase enzyme (e.g., NEBNEXT DSDNA FRAGMENTASE), and a partially complementary universal sequence. A second mixture Z2 comprises capsule 1704 generated as described above and magnesium chloride in a concentration sufficient to activate the fragmentase enzyme. Mixture Z1, Z2, or both Z1 and Z2 also comprise T4 polymerase, Taq polymerase, and a thermostable ligase.

Mixtures Z1 and Z2 are combined and a capsule within a capsule is formed according to methods described elsewhere in this disclosure, such as flow focusing. FIG. 17 illustrates a capsule within a capsule produced according to the method described above. The outer capsule 1703 comprises an inner capsule 1704 and medium 1705. The inner capsule 1704 is one member of a library of encapsulated, bead-bound single-stranded barcode adapters. Thus, inner capsule 1704 comprises multiple copies of structure 1700, which can be used to generate a free single-stranded adapter-barcode sequence 1702 and attach the same barcode adapter to a polynucleotide within a partition, such as outer capsule 1703.

The medium 1705 contains the contents of mixtures Z1 and Z2, described above. More specifically, medium 1705 comprises target polynucleotide 1706, the partially complementary universal sequence 1707, and the enzyme mix 1708 comprising fragmentase, T4 polymerase, Taq polymerase, thermostable ligase, magnesium chloride, and appropriate buffers.

Upon generation of the capsule within capsule, and exposure of the capsule within capsule to appropriate conditions, the enzymes process the target polynucleotide. More specifically, the fragmentase fragments the target polynucleotide and the T4 polymerase blunts the ends of the fragmented target polynucleotide. The fragmentase and T4 polymerase are then heat inactivated and a stimulus is used to rupture inner capsule 1704, releasing its contents into outer capsule 1703. The Taq polymerase adds 3'-A overhangs to the fragmented, blunt-ended target polynucleotide. The single-stranded adapter-barcode sequence 1702 hybridizes with the partially complementary universal sequence 1707 and is released from the bead with light, forming a forked adapter with a 3'-T overhang that is compatible with the 3'-A overhang on the fragmented target polynucleotide. The thermostable ligase ligates the forked adapter to the fragmented target polynucleotide, generating barcoded target polynucleotide. The outer capsule 1703 is then ruptured, samples from all outer capsules are pooled, and the target polynucleotides are sequenced. Additional preparation steps (e.g., bulk amplification, size selection, etc.) may be performed as needed prior to sequencing.

In some cases Z1 can comprise multiple versions of the partially complementary universal sequence 1707. Furthermore, although this example demonstrates barcoding of a target polynucleotide by utilizing a thermostable ligase, PCR can also be used to accomplish this step.

Example 12

Barcoding with Bead Emulsion PCR and Fragmentation by Sonication

Figure 18:
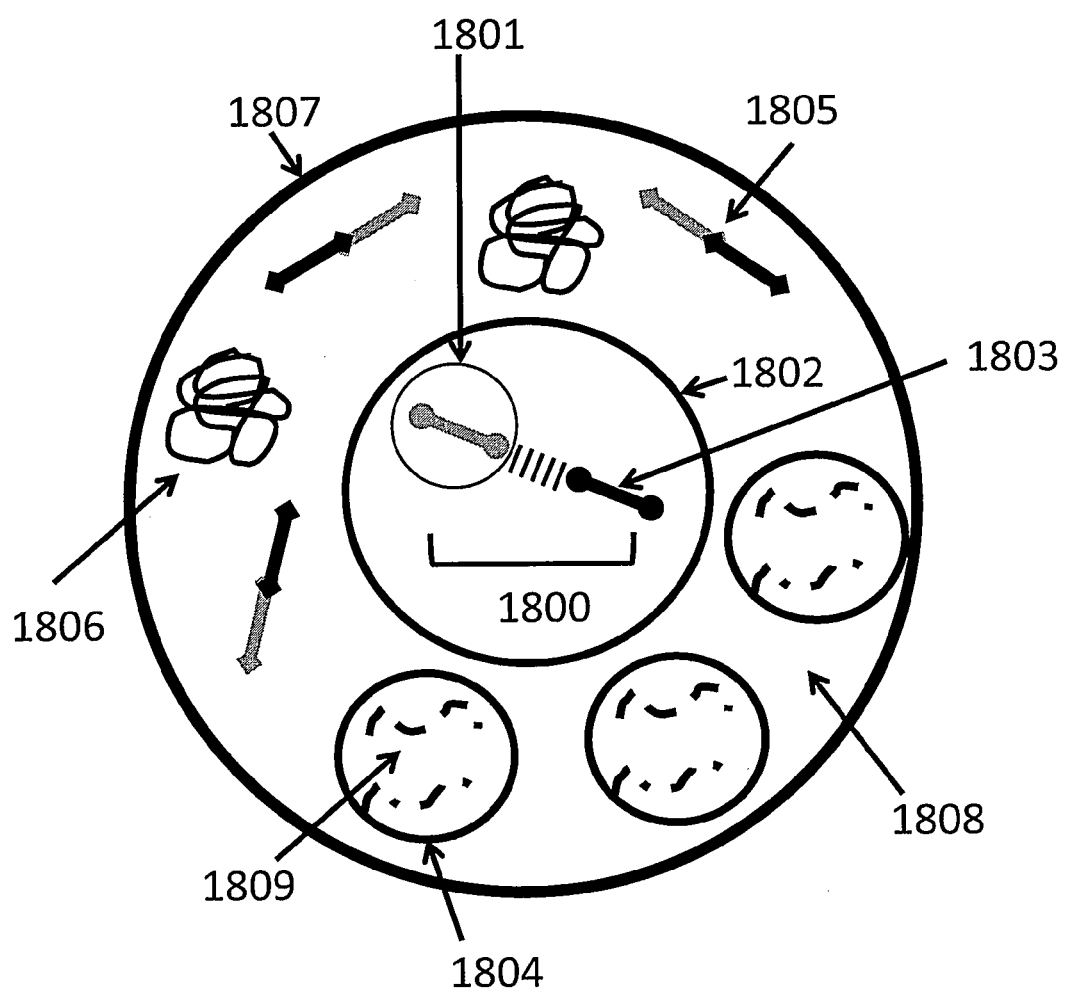
FIG. 18 schematically depicts capsules within a capsule described in Example 12.

As shown in FIG. 18, structure 1800 comprising a magnetic bead (1801)-bound single-stranded adapter-barcode sequence 1802 is produced according to methods described in Example 8, Example 9, or any other method described herein. Interfacial polymerization is performed on the droplet comprising the structure 1800, to generate a capsule 1803 comprising single-stranded adapter-barcode sequence 1802 attached, via a photolabile linker, to a bead 1801. Target polynucleotides (i.e., polynucleotides to be fragmented) are partitioned into capsules 1804. The capsules 1804 comprising the target polynucleotides are configured to withstand ultrasonic stress. The capsules 1804 comprising the target polynucleotides are exposed to ultrasonic stress (e.g., COVARIS Focused-Ultrasonicator) and the target polynucleotide is fragmented, generating fragmented target polynucleotide capsules.

A mixture Z1 is prepared, comprising capsule 1803, the fragmented target polynucleotide capsules 1804, a partially complementary universal sequence 1805, an enzyme mixture (T4 polymerase, Taq polymerase, and a thermostable ligase) 1806, and appropriate buffers. A capsule within capsule is generated according to the method described elsewhere in this disclosure, such as flow focusing.

FIG. 18 illustrates capsules within a capsule produced according to the methods described above. The outer capsule 1807 comprises capsules 1803 and 1804 and medium 1808. The inner capsules 1803 and 1804 include capsules comprising structure 1800 and capsules comprising fragmented target polynucleotide 1809, respectively. Inner capsule 1803 comprises multiple copies of structure 1800, which can be used to generate a free single-stranded barcode adapter 1802 and attach the same barcode adapter to a polynucleotide within a partition, such as the fragmented polynucleotides 1809 contained within inner capsules 1804.

The medium 1808 contains the contents of mixture Z1, described above. More specifically, medium 1808 comprises a partially complementary universal sequence 1805, an enzyme mixture (T4 polymerase, Taq polymerase, and a thermostable ligase) 1806, and appropriate buffers.

Inner capsules 1804 comprising fragmented target polynucleotides 1809 are exposed to a stimulus to rupture them and release their contents into the contents of outer capsule 1807. The T4 polymerase blunts the ends of the fragmented target polynucleotides; the Taq polymerase adds 3'-A overhangs to the fragmented, blunt-ended target polynucleotide. The T4 polymerase and Taq polymerase is then heat-inactivated and a stimulus is applied to release the contents of inner capsule 1803 into outer capsule 1807. The single-stranded adapter-barcode sequence 1802 hybridizes with the partially complementary universal sequence 1805 and the adapter is released from the bead with light forming a forked adapter with a 3'-T overhang that is compatible with the 3'-A overhang on the fragmented target polynucleotide. The thermostable ligase ligates the forked adapter to the fragmented target polynucleotide, generating a barcoded target polynucleotide. The outer capsule 1807 is then ruptured, samples from all outer capsules are pooled, and the target polynucleotides are sequenced.

In some cases Z1 can comprise multiple versions of the partially complementary universal sequence 1807. Furthermore, although this example demonstrates barcoding of a target polynucleotide by utilizing a thermostable ligase, PCR can also be used to accomplish this step.

Example 13

Barcoding with Multiple Annealing and Looping-Based Amplification (MALBAC)

As shown in FIG. 19*a*, a primer comprising SEQ ID NO: 36 is prepared. The primer comprises a barcode region (designated "Barcode"), a primer sequencing region (designated "PrimingSeq"), and a eight-nucleotide variable region (designated as " ") that may comprise any combination of A, T, C, or G. The primer shown in FIG. 19 is combined with a target polynucleotide (indicated by the loop in FIG. 19), along with a polymerase (e.g., Vent, exo+DeepVent, exo−DeepVent) possessing of strand-displacement activity into a partition (e.g., a capsule, droplet of an emulsion, etc.). In some cases, a non strand-displacing polymerase (e.g., Taq, PfuUltra) is used. The partition is then subject to MALBAC amplification. Appropriate MALBAC cycling conditions are known and are, described for example, in Zong et al., *Science,* 338(6114), 1622-1626 (2012), which is incorporated herein by reference, in its entirety.

A looped MALBAC product is produced as shown in FIG. 19*b* as SEQ ID NO: 23. The looped MALBAC product comprises the original primer shown in FIG. 19*a*, the target polynucleotide to be barcoded oriented in a loop, and a region complementary to and hybridized to the original primer sequence. The partition is broken and the contents recovered. In some cases, a plurality of partitions are generated. The partitions are collectively broken, the contents of each recovered, and then pooled.

Next, the generated MALBAC product shown in FIG. 19*b* is treated with a restriction enzyme (e.g., BfuC1 or similar) to generate a 4-basepair overhang (in this case, GATC shown in italics) on the MALBAC product. This structure is represented by SEQ ID NO: 24 and shown in FIG. 19*c*. A forked adapter, shown in FIG. 19*d* as SEQ ID NO: 25 and SEQ ID NO: 37, comprising an overhang (in this case, CTAG shown in bold) complementary to the overhang generated on the MALBAC product. The forked adapter is mixed with the MALBAC product in FIG. 19*c* and the complementary regions hybridize. A thermostable ligase is used to ligate the forked adapter and MALBAC product together to form the desired structure FIG. 19*e* as SEQ ID NO: 26. Additional amplification methods (e.g., PCR) can be used to add additional regions (e.g., immobilization regions, additional barcodes, etc.) to the forked adapter.

In some cases, other basepair overhangs (e.g., 1 basepair overhang-10 basepair overhang) may be desired. Restriction enzymes used to generate these overhangs may be used as an alternative, including those described herein, where desired. In one example, a two basepair overhang is generated on the MALBAC product using Taq$^\alpha$I.

Figure 19F:
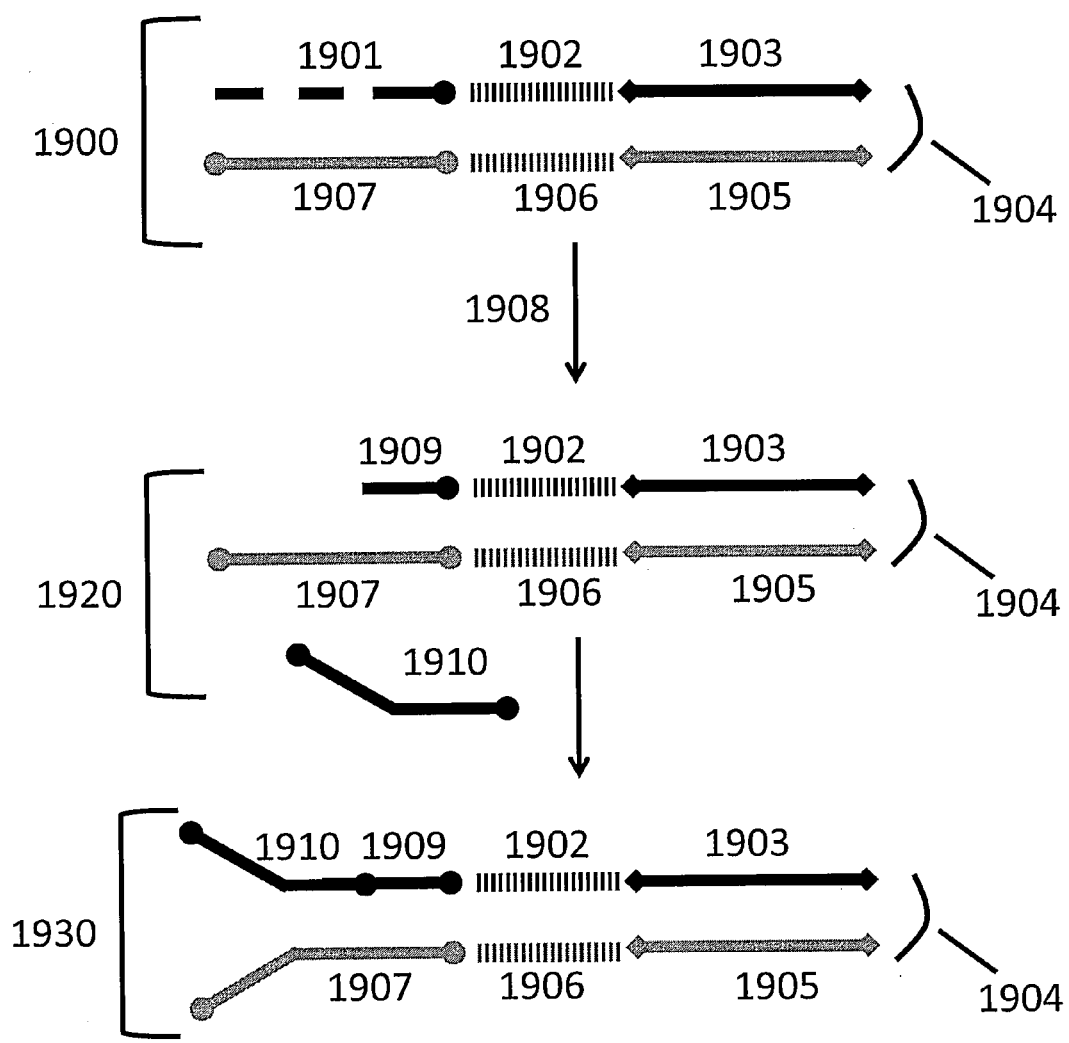
FIG. 19f describes example methods and structures described in Example 13.

As an alternative, the primer shown in FIG. 19*a* can be designed such that an RNA primer sequence is placed 5' of the barcode region, such that an RNAase is used to generate an overhang. As shown in FIG. 19*f*, MALBAC product 1900 comprises an RNA primer sequence 1901 placed 5' of a barcode region 1902. MALBAC product 1900 also comprises a sequencing primer region 1903, the target polynucleotide 1904, a complementary sequencing primer region 1905, a complementary barcode region 1906, and a region 1907 complementary to the RNA primer sequence 1901. MALBAC product 1900 is treated with an RNAse H 1908 and the RNA primer region sequence 1901 is digested to yield a 2-6 basepair overhang 1909 on MALBAC product 1900 to give structure 1920. A universal complementary region 1910 is then added to structure 1910 that comprises a region complementary to the overhang on structure 1910. Universal complementary region 1910 then hybridizes with structure 1920 and a thermostable ligase is used to ligate universal complementary region 1910 to structure 1920.

Example 14

Barcoding with Multiple Annealing and Looping-Based Amplification (MALBAC)

Figure 20:
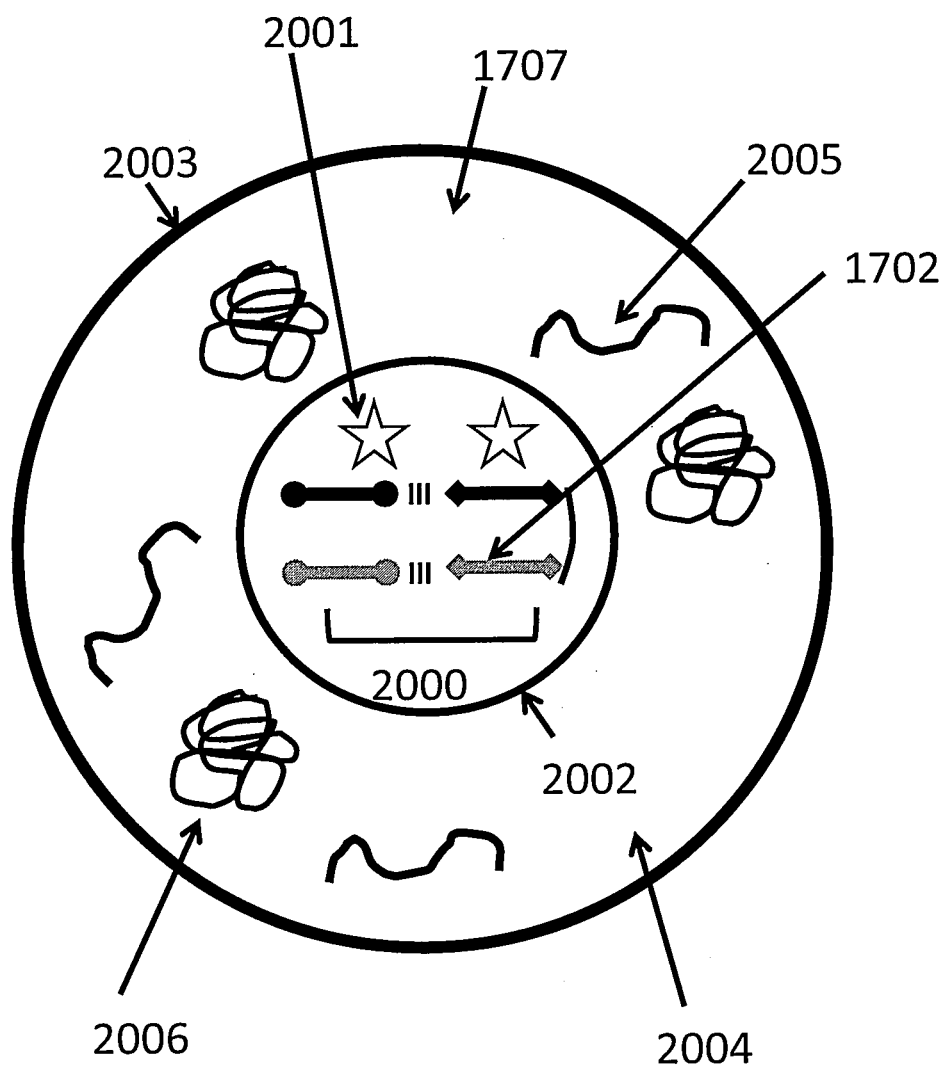
FIG. 20 schematically depicts a capsule within a capsule described in Example 14.

As shown in FIG. 20, a template 2000 comprising a barcode region is combined with agents 2001 necessary for PCR into a capsule 2002, using, for example interfacial polymerization or any other method described herein. PCR is used to generate a MALBAC primer from the template 2000. Next, the capsule 2000 is encapsulated into an outer capsule 2003 that also comprises a mixture 2004 that comprises a target polynucleotide 2005 to be barcoded and reagents 2006 necessary for MALBAC amplification (e.g., DeepVent polymerase, dNTPs, buffer). Capsule 2002 is broken upon proper exposure of capsule 2002 to a stimulus designed to rupture capsule 2002, the contents of capsule 2002 mix with those of mixture 2004. MALBAC amplification of the target polynucleotide 2005 commences to produce a MALBAC product similar to that described as that shown as 1900 in FIG. 19*f*.

The outer capsule 2003 is then broken with the appropriate stimulus and the contents recovered. The MALBAC product is then treated with an appropriate restriction enzyme and coupled to a forked adapter in a matter as described in Example 13. Additional downstream preparation steps (e.g., bulk amplification, size selection, etc.) are then performed as needed.

Example 15

Barcoding with Multiple Annealing and Looping-Based Amplification (MALBAC)

Figure 21A:
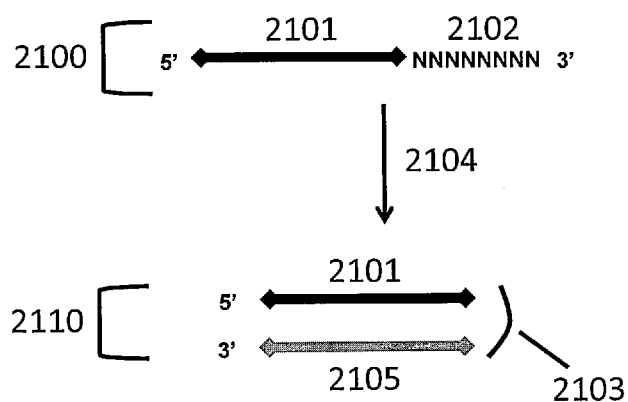
FIGS. 21a-c schematically depict methods and structures described in Example 15.

As shown in FIG. 21*a*, a MALBAC primer 2100 is prepared. MALBAC primer 2100 comprises a sequence priming region 2101 and an 8-nucleotide variable region 1902. Primer 2100 is combined with target polynucleotide 2103, along with a polymerase (e.g., Vent, exo+DeepVent, exo−DeepVent) possessing of strand-displacement activity into a partition (e.g., a capsule, emulsion, etc.). In some cases, a non strand-displacing polymerase (e.g., Taq, PfuUltra) is used. The partition is then subject to MALBAC amplification 2104.

Figure 21B:
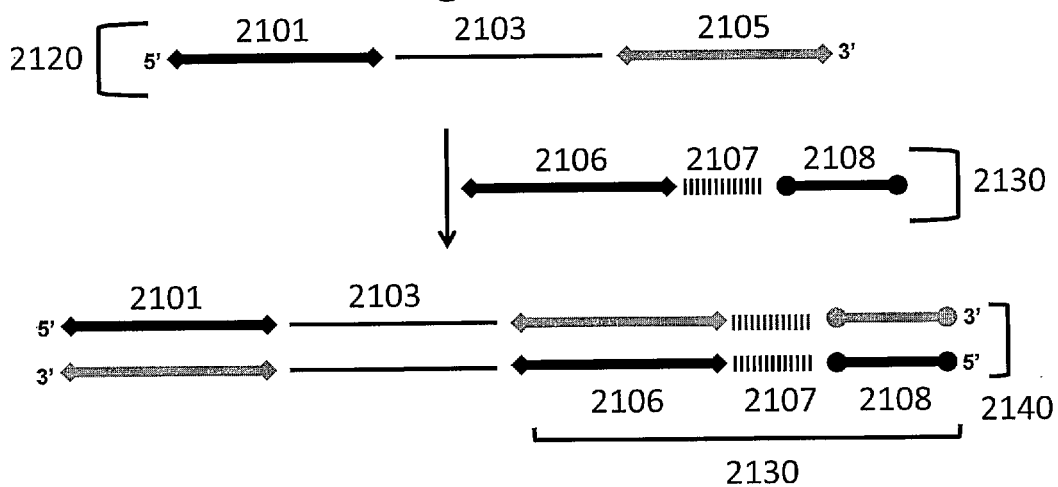

A looped MALBAC product 2110 is produced and comprises sequencing priming region 2101, target polynucleotide 2103, and a complementary sequence priming region 2105. Shown in linear form 2120 in FIG. 21*b*, MALBAC product 2110 is then contacted with another primer 2130 that comprises a sequencing primer region 2106, a barcode region 2107, and an immobilization region 2108. Primer 2130 is produced using asymmetric digital PCR. Using a single cycle of PCR, the primer is used to generate double-stranded product 2140 that comprises primer 2130, and, thus, barcode region 2107.

Figure 21C:
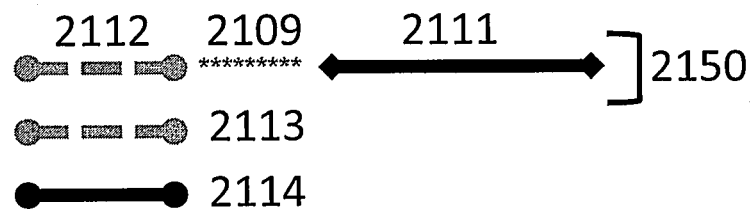

Double-stranded product 2140 may be then denatured and subsequently contacted with another primer 2150 shown in FIG. 21c. Primer 2150 comprises a barcode region 2109, a sequencing primer region 2111, and an immobilization region 2112. In the presence of primers 2113 and 2114, additional rounds of PCR can add the barcode region 2109 to the end of the target polynucleotide that attached to barcode region 2107. Additional downstream preparation steps (e.g., bulk amplification, size selection, etc.) are then performed as needed.

Example 16

Barcoding with Multiple Annealing and Looping-Based Amplification (MALBAC)

Figure 22:
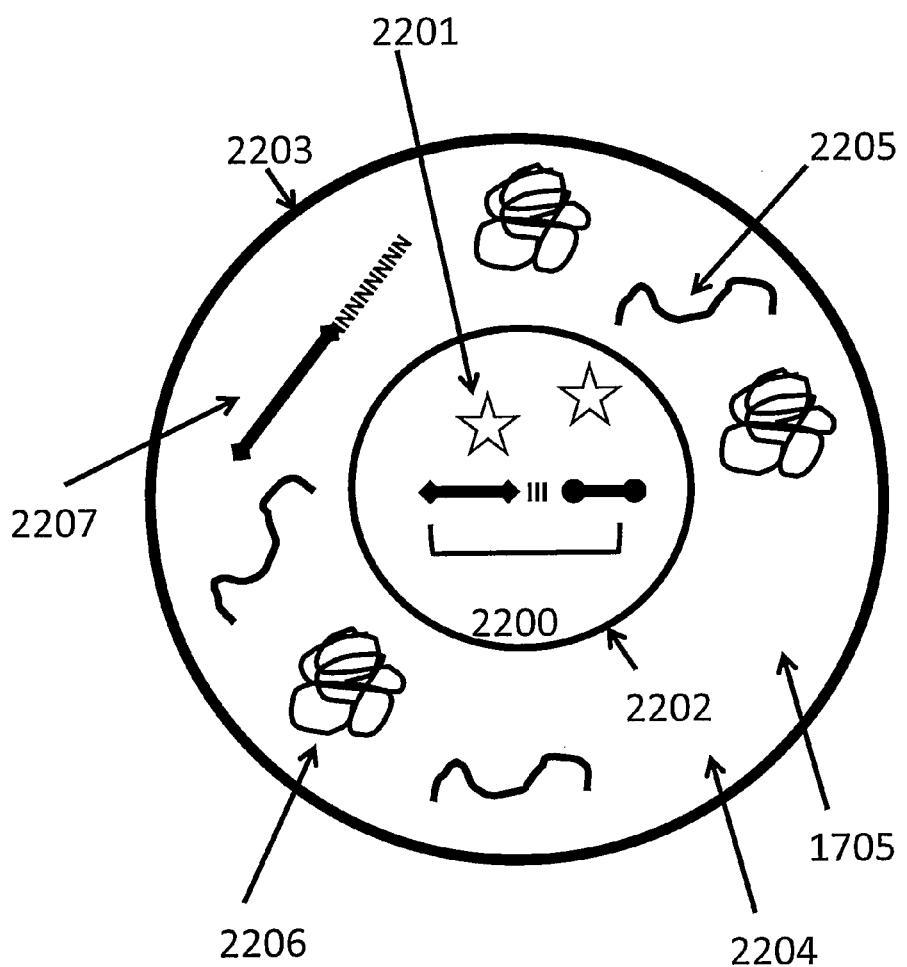
FIG. 22 schematically depicts a capsule within a capsule described in Example 16.

As shown in FIG. 22, a primer template 2200 comprising a barcode region is combined with agents 2201 necessary for PCR into a capsule 2202, using, for example interfacial polymerization or any other method described herein. PCR is then used to generate a primer from template 2200. Next, the capsule 2200 is encapsulated into an outer capsule 2003 that also comprises a mixture 2204 that comprises a target polynucleotide 2205 to be barcoded, reagents 2206 necessary for MALBAC amplification (e.g., DeepVent polymerase, dNTPs, buffer), and a MALBAC primer 2207 that does not comprise a barcode (similar to MALBAC primer 2100 described in Example 15). MALBAC amplification of the target polynucleotide 2205 commences to produce a MALBAC product similar to that described as that shown as 2110 in FIG. 21a. Capsule 2202 is then broken upon proper exposure of capsule 2202 to a stimulus designed to rupture capsule 2202, the contents of capsule 2202 mix with those of mixture 2004. A single cycle of PCR commences using the primer generated from template 2200 to generate a barcoded product, similar to that described in Example 15.

Outer capsule 2203 is then broken with the appropriate stimulus and the contents recovered. Additional downstream preparation steps (e.g., bulk amplification, size selection, addition of additional barcodes, etc.) are then performed as needed.

Example 17

Barcoding with Transposase and Tagmentation

Figure 23:
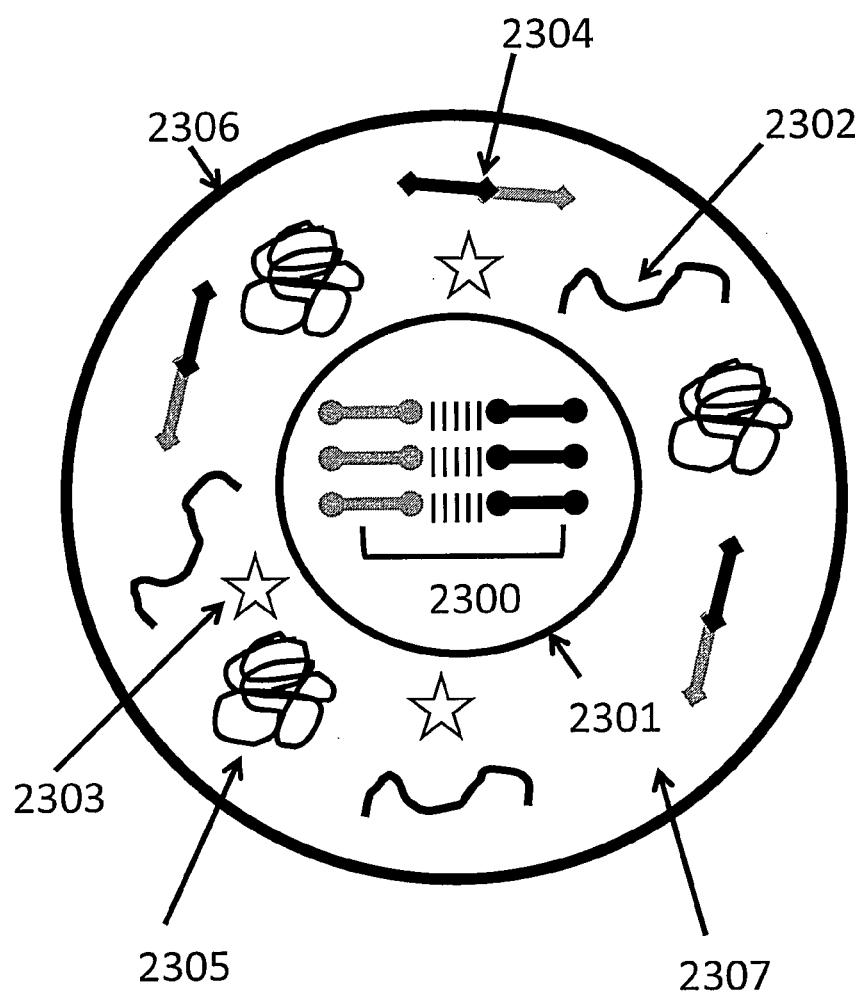
FIG. 23 schematically depicts a capsule within a capsule described in Example 17.

As shown in FIG. 23, a single-stranded adapter-barcode polynucleotide sequence 2300 is synthesized, partitioned, amplified, and sorted as described in Example 1, or by any other method described in this disclosure. Interfacial polymerization is performed on the droplet comprising the single-stranded adapter-barcode polynucleotide sequence, to generate a capsule 2301.

Two mixtures are prepared. Mixture Z1 comprises a target polynucleotide 2302 (i.e., a polynucleotide to be fragmented and barcoded), a transposome 2303, and a partially complementary universal sequence 2304. A second mixture Z2 comprises capsule 2301, generated as described above and reagents 2305 necessary for PCR as described elsewhere herein.

Mixtures Z1 and Z2 are combined and a capsule within a capsule is formed according to methods described elsewhere in this disclosure, such as flow focusing. FIG. 23 illustrates a capsule within a capsule produced according to the method described above. The outer capsule 2306 comprises capsule 2301 and medium 2307. Capsule 2301 is one member of a library of encapsulated single-stranded adapter-barcode polynucleotides. Thus, capsule 2301 comprises multiple copies of a single-stranded adapter-barcode polynucleotide 2300, which can be used to attach the same barcode to a polynucleotide within a partition, such as outer capsule 2306.

The medium 2307 contains the contents of mixtures Z1 and Z2, described above. More specifically, medium 2307 comprises target polynucleotide 2302, the partially complementary universal sequence 2304, and the reagents 2305 necessary for PCR, including a hot start Taq.

Upon generation of the capsule within capsule, and exposure of the capsule within capsule to appropriate conditions, the transposome process the target polynucleotide. More specifically, the transposase fragments the target polynucleotide via tagmentations and tags it with a common priming sequence. The tagged target polynucleotide is then heated to fill in any gap in the target nucleotide generated by the transposase. The transposase is then heat inactivated and a stimulus is used to rupture inner capsule 2301, releasing its contents into outer capsule 2306. The hot start Taq is activated by heating the outer capsule 2306 to 95° C. The reaction proceeds with limited cycle PCR to add single-stranded adapter-barcode polynucleotide sequence 2300 to target polynucleotide 2302. The outer capsule 2306 is then ruptured and the target polynucleotides are sequenced.

It should be understood from the foregoing that, while particular implementations have been illustrated and described, various modifications may be made thereto and are contemplated herein. It is also not intended that the invention be limited by the specific examples provided within the specification. While the invention has been described with reference to the aforementioned specification, the descriptions and illustrations of the preferable embodiments herein are not meant to be construed in a limiting sense. Furthermore, it shall be understood that all aspects of the invention are not limited to the specific depictions, configurations or relative proportions set forth herein which depend upon a variety of conditions and variables. Various modifications in form and detail of the embodiments of the invention will be apparent to a person skilled in the art. It is therefore contemplated that the invention shall also cover any such modifications, variations and equivalents. It is intended that the following claims define the scope of the invention and that methods and structures within the scope of these claims and their equivalents be covered thereby.

What is claimed is:

1. A method of synthesizing a library of polynucleotides comprising barcode sequences, said method comprising:
   synthesizing a plurality of polynucleotides comprising barcode sequences;
   separating said polynucleotides into a plurality of partitions, thereby generating partitioned polynucleotides, wherein each partition comprising a polynucleotide comprises multiple copies of the same polynucleotide comprising a barcode sequence prior to amplifying said partitioned polynucleotides;
   amplifying said partitioned polynucleotides, thereby generating a library of amplified polynucleotides, comprising at least about 100,000 different barcode sequences;
   wherein said amplified polynucleotides are attached to a bead; and
   isolating partitions comprising amplified polynucleotides.

2. The method of claim 1, wherein said synthesizing comprises including a mixture of adenine, thymine, guanine, and cytosine in a coupling reaction.

3. The method of claim 1, wherein said separating comprises performing a limiting dilution, thereby generating diluted polynucleotides.

4. The method of claim 3, wherein said separating further comprises partitioning said diluted polynucleotides.

5. The method of claim 1, wherein said amplifying is performed by a method selected from the group consisting of polymerase chain reaction, asymmetric polymerase chain reaction, emulsion PCR (ePCR), ePCR including the use of a bead, ePCR including the use of a hydrogel, multiple annealing and looping-based amplification cycles (MALBAC), single primer isothermal amplification, and combinations thereof.

6. The method of claim 1, wherein said isolating is performed by flow-assisted sorting.

7. The method of claim 1, wherein a hairpin structure is formed from a polynucleotide selected from the group consisting of said polynucleotides comprising barcode sequences and said amplified polynucleotides.

8. The method of claim 7, further comprising cutting said hairpin structure within an unannealed region.

9. The method of claim 1, further comprising annealing said amplified polynucleotides with a partially complementary sequence.

10. The method of claim 9, wherein said partially complementary sequence comprises a barcode sequence.

11. The method of claim 1, further comprising attaching at least one of said amplified polynucleotides to a target sequence.

12. The method of claim 11, further comprising fragmenting said target sequence prior to said attaching step.

13. The method of claim 12, wherein fragmenting said target sequence is by a method selected from the group consisting of mechanical shear and treatment with an enzyme.

14. The method of claim 13, wherein said mechanical shear is induced by ultrasound.

15. The method of claim 13, wherein said enzyme is selected from the group consisting of a restriction enzyme, a fragmentase, and a transposase.

16. The method of claim 11, wherein said attaching is performed by a method selected from the group consisting of ligation and amplification.

17. The method of claim 16, wherein said amplification is a MALBAC amplification performed with MALBAC primers, thereby generating a MALBAC amplification product.

18. The method of claim 17, wherein said MALBAC primers comprise said amplified polynucleotides.

19. The method of claim 1, wherein following the separating step, the plurality of partitions comprises, on average, about 0.5 polynucleotides comprising barcode sequences per partition.

20. The method of claim 1, wherein following the separating step, the plurality of partitions comprises, on average, about 0.1 polynucleotides comprising barcode sequences per partition.

21. The method of claim 1, wherein said partitions are selected from the group consisting of droplets, capsules, and wells.

22. The method of claim 1, wherein said polynucleotides comprising barcode sequences further comprise a sequence selected from the group consisting of an immobilization sequence, an annealing sequence for a sequencing primer, and a sequence compatible for ligation with a target polynucleotide.

23. The method of claim 1, wherein said library comprises at least about 500,000 different barcode sequences.

24. The method of claim 1, wherein said library comprises at least about 1,000,000 different barcode sequences.

25. The method of claim 1, wherein said library comprises at least about 2,500,000 different barcode sequences.

26. The method of claim 1, wherein said library comprises at least about 5,000,000 different barcode sequences.

27. The method of claim 1, wherein said library comprises at least about 10,000,000 different barcode sequences.

28. The method of claim 1, wherein said library comprises at least about 25,000,000 different barcode sequences.

29. The method of claim 1, wherein said library comprises at least about 50,000,000 different barcode sequences.

30. The method of claim 1, wherein said library comprises at least about 100,000,000 different barcode sequences.

31. A method of synthesizing a library of polynucleotides comprising barcode sequences, said method comprising:
    synthesizing a plurality of polynucleotides comprising barcode sequences;
    separating said polynucleotides into a plurality of partitions, thereby generating partitioned polynucleotides;
    amplifying said partitioned polynucleotides, using an RNA primer thereby generating amplified polynucleotides;
    optionally exposing said amplified polynucleotides to RNase H; and
    isolating partitions comprising amplified polynucleotides.

32. A method of synthesizing a library of polynucleotides comprising barcode sequences, said method comprising:
    synthesizing a plurality of MALBAC primer polynucleotides comprising barcode sequences;
    separating said polynucleotides into a plurality of partitions, thereby generating partitioned polynucleotides;
    amplifying said partitioned polynucleotides, thereby generating amplified polynucleotides; and
    isolating partitions comprising amplified polynucleotides.

33. The method of claim 31, wherein said library comprises at least about 500,000 different barcode sequences.

34. The method of claim 31, wherein said library comprises at least about 1,000,000 different barcode sequences.

35. The method of claim 31, wherein said library comprises at least about 2,500,000 different barcode sequences.

36. The method of claim 31, wherein said library comprises at least about 5,000,000 different barcode sequences.

37. The method of claim 32, wherein said library comprises at least about 500,000 different barcode sequences.

38. The method of claim 32, wherein said library comprises at least about 1,000,000 different barcode sequences.

39. The method of claim 32, wherein said library comprises at least about 2,500,000 different barcode sequences.

40. The method of claim 32, wherein said library comprises at least about 5,000,000 different barcode sequences.

* * * * *